(12) United States Patent
Goedegebuur et al.

(10) Patent No.: US 7,951,570 B2
(45) Date of Patent: *May 31, 2011

(54) CBH1 HOMOLOGS AND VARIANT CBH1 CELLULASES

(75) Inventors: Frits Goedegebuur, Rozenlaan (NL); Peter Gualfetti, San Francisco, CA (US); Colin Mitchinson, Half Moon Bay, CA (US); Paulien Neefe, Zoetermeer (NL)

(73) Assignee: Danisco US Inc., Palo Alto, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/250,227

(22) Filed: Oct. 13, 2008

(65) Prior Publication Data

US 2009/0163397 A1 Jun. 25, 2009

Related U.S. Application Data

(63) Continuation of application No. 10/804,785, filed on Mar. 19, 2004, now Pat. No. 7,452,707.

(60) Provisional application No. 60/456,368, filed on Mar. 21, 2003, provisional application No. 60/458,696, filed on Mar. 27, 2003.

(51) Int. Cl.
*C12N 9/42* (2006.01)
*C12N 1/00* (2006.01)
*C12P 21/06* (2006.01)
*C07H 21/04* (2006.01)

(52) U.S. Cl. ............... 435/209; 435/69.1; 435/252.3; 435/254.4; 435/254.5; 435/254.6; 435/254.7; 435/254.1; 435/254.11; 536/23.2

(58) Field of Classification Search ............ 435/209, 435/69.1, 252.3, 254.4, 254.5, 254.6, 254.7; 536/23.2
See application file for complete search history.

(56) References Cited

U.S. PATENT DOCUMENTS

| | | | |
|---|---|---|---|
| 4,435,307 A | 3/1984 | Barbesgaard et al. | 252/174.12 |
| 4,822,516 A | 4/1989 | Suzuki et al. | 252/174.12 |
| 5,246,853 A | 9/1993 | Clarkson et al. | 435/263 |
| 5,648,263 A | 7/1997 | Schulein et al. | 435/263 |
| 5,691,178 A | 11/1997 | Schulein et al. | 435/209 |
| 5,776,757 A | 7/1998 | Schulein et al. | 435/209 |
| 5,912,157 A | 6/1999 | von der Osten et al. | 435/209 |
| 5,955,270 A | 9/1999 | Radford et al. | 435/6 |
| 6,117,664 A | 9/2000 | Schulein et al. | 435/209 |
| 6,184,019 B1 | 2/2001 | Miettinen-Oinonen et al. | 435/6 |
| 6,255,115 B1 | 7/2001 | Beijersbergen et al. | 435/477 |
| 6,261,828 B1 | 7/2001 | Lund | 435/263 |
| 7,452,707 B2 * | 11/2008 | Goedegebuur et al. | 435/209 |
| 2009/0075336 A1 * | 3/2009 | Goedegebuur et al. | 435/69.1 |

FOREIGN PATENT DOCUMENTS

| | | |
|---|---|---|
| EP | 0 137 280 A1 | 4/1985 |
| GB | 1 368 599 | 10/1974 |
| GB | 2 094 826 A | 9/1982 |
| GB | 2 095 275 A | 9/1982 |
| WO | WO 92/06209 A1 | 4/1992 |
| WO | WO 98/31821 | 7/1998 |
| WO | WO 01/04284 A1 | 1/2001 |
| WO | WO 2004/016760 A2 | 2/2004 |

OTHER PUBLICATIONS

Broun et al., Catalytic plasticity of fatty acid modification enzymes underlying chemical diversity of plant lipids. Science, 1998, vol. 282: 1315-1317.*
Chica et al., Semi-rational approaches to engineering enzyme activity: combining the benefits of directed evolution and rational design. Curr. Opi. Biotechnol., 2005, vol. 16: 378-384.*
Devos et al., Practical limits of function prediction. Proteins: Structure, Function, and Genetics. 2000, vol. 41: 98-107.*
Seffernick et al., Melamine deaminase and Atrazine chlorohydrolase: 98 percent identical but functionally different. J. Bacteriol.,2001, vol. 183 (8): 2405-2410.*
Sen et al., Developments in directed evolution for improving enzyme functions. Appl. Biochem. Biotechnol., 2007, vol. 143: 212-223.*
Whisstock et al., Prediction of protein function from protein sequence. Q. Rev. Biophysics., 2003, vol. 36 (3): 307-340.*
Witkowski et al., Conversion of b-ketoacyl synthase to a Malonyl Decarboxylase by replacement of the active cysteine with glutamine. Biochemistry, 1999, vol. 38: 11643-11650.*
Aleksenko, A., et al., "The plasma replicator AMA1 in *Aspergillus nidulans* is an inverted duplication of a low copy number dispersed genomic repeat." *Molecular Microbiology* 19(3):565-574, 1996.
*Alexopoulos, C. J., *Introductory Mycology*, 2d. ed., New York, Wiley, 1962.
Altschul, S.F., et al., "Basic Local Alignment Search Tool." *J. Mol. Biol.* 215:403-410, 1990.
Altschul, S.F., et al., "Gapped BLAST and PSI-BLAST: a new generation of protein database search programs." *Nucl. Acids Res.*, 25(17): 3389-3402, 1997.
Aro, N., et al., "ACEII, a Novel Transcriptional Activator Involved in Regulation of Cellulase and Xylanase Genes of *Trichoderma reesei*." *J. Biol. Chem.*, 276(26): 24309-24314, 2001.
*Aubert, J.-P., et al., ed., *Biochemistry and genetics of cellulose degradation*, Proceedings of a symposium organized by the Federation of the Microbiological Societies and the French Society for Microbiology on Sep. 7-9, 1987, Academic Press, 1988.

(Continued)

*Primary Examiner* — Ganapathirama Raghu

(57) ABSTRACT

Disclosed are a number of homologs and variants of *Hypocrea jecorina* Cel7A (formerly *Trichoderma reesei* cellobiohydrolase I or CBH1), nucleic acids encoding the same and methods for producing the same. The homologs and variant cellulases have the amino acid sequence of a glycosyl hydrolase of family 7A wherein one or more amino acid residues are substituted and/or deleted.

4 Claims, 10 Drawing Sheets

OTHER PUBLICATIONS

*Ausubel, F. M., et al., (eds.), *Current Protocols in Molecular Biology*, John Wiley & Sons, New York, NY, 1993.

*Ausubel, F.M., et al., (eds.), *Current Protocols in Molecular Biology*, Greene Publishing and Wiley-Interscience, New York, NY, 1987.

Bajar, A., et al., "Identification of a fungal cutinase promoter that is inducible by a plant signal via a phosphorylated transacting factor." *Proc. Natl. Acad. Sci. USA* 88: 8202-8212, 1991.

Baldwin, D., et al., "A comparison of gel-based, nylon filter and microarray techniques to detect differential RNA expression in plants." *Curr. Opin. Plant Biol.* 2(2):96-103, 1999.

Barclay, S. L., et al., "Efficient Transformation of *Dictyostelium discoideum* Amoebae." *Molecular and Cellular Biology* 3(12): 2117-2130, 1983.

Baulcombe, D., "Viruses and gene silencing in plants." Arch. Virol., Supp. 15: 189-201, Springer-Verlag, New York, NY, 1999.

Becker, D., et al., "Engineering of a glycosidase Family 7 cellobiohydrolase to more alkaline pH optimum: The pH behaviour of *Trichoderma reesei* Cel7A and its E223S/A224H/L225V/T226A/D262G mutant." *Biochem. J.* 356(1): 19-30, 2001.

Berges, T., et al., "Isolation of uridine auxotrophs from *Trichoderma reesei* and efficient transformation with the cloned ura3 and ura5 genes." *Curr. Genet.* 19: 359-365, 1991.

Bhikhabhai, R., et al., "Isolation of Cellulolytic Enzymes from *Trichoderma reesei* QM 9414." *J. Appl. Biochem.*, 6:336-345, 1984.

Boel, E., et al., "Two different types of intervening sequences in the glucoamylase gene from *Aspergillus niger.*" *EMBO J.* 3(7): 1581-1585, 1984.

Brigidi, P., et al., "Genetic transformation of intact cells of *Bacillus subtilis* by electroporation." *FEMS Microbiol. Lett.*, 67: 135-138, 1990.

Broun, P., et al. "Catalytic plasticity of fatty acid modification enzymes underlying chemical diversity of plant lipids." *Science*, 282:1315-1317, 1998.

Brumbauer, A., et al., "Fractionation of cellulase and β-glucosidase in a *Trichoderma reesei* culture liquid by use of two-phase partitioning." *Bioseparation* 7: 287-295, 1999.

Burley, S.K., et al.. "Aromatic-Aromatic Interaction: A Mechanism of Protein Structure Stabilization." *Science*, 229: 23-29, 1985.

Campbell, E.I., et al., "Improved transformation efficiency of *Aspergillus niger* using homologous niaD gene for nitrate reductase." *Curr. Genet.* 16: 53-56; 1989.

Carter, P., et al., "Improved oligonucleotide site-directed mutagenesis using M13 vectors." *Nucl. Acids Res.* 13(12): 4431-4443, 1985.

Chen, H., et al., "Purification and characterization of two extracellular β-glucosidases from *Trichoderma reesei.*" *Biochem et Biophysica Acta* 1121: 54-60, 1992.

Cheng, C., et al., "Nucleotide sequence of the cellobiohydrolase gene from *Trichoderma viride.*" *Nucl. Acids Res.* 18(18): 5559, 1990.

*Coligan, J. E. et al., eds., *Current Protocols In Immunology*, Wiley, 1991.

Collen, A., et al., "Genetically engineered peptide fusions for improved protein partitioning in aqueous two-phase systems—Effect of fusion localization on endoglucanase I of *Trichoderma reesei.*" *Journal of Chromatography A*, 910: 275-284, 2001.

Coughlan, M., et al., "Comparative Biochemistry of Fungal and Bacterial Cellulolytic Enzyme Systems." In *Biochemistry and Genetics of Cellulose Degradation*, Aubert, J.P., et al. (eds.), Academic Press, pp. 11-30, 1988.

Covert, S.F., et al., "Structure, Organization and Transcription of a Cellobiohydrolase Gene Cluster from *Phanerochaete chrysosporium.*" *Appl. Environ. Microbiol.*, 58(7): 2168-2175, 1992.

Cummings, C., et al., "Secretion of *Trichoderma reesei* β-glucosidase by *Saccharomyces cerevisiae.*" *Curr. Genet.*, 29: 227-233, 1996.

Database Geneseq. "Sequence encoded by cellobiohydrolase-I (CBHI) gene." Database Accessuib bi, AAP50133, 1991.

Dayhoff, M.O., et al., "A Model of Evolutionary Change in Proteins." In *Atlas of Protein Sequence and Structure*, National Biomedical Research Foundation, Washington, D.C., vol. 5, Supplement 3, Chapter 22, pp. 345-352, 1978.

*Doolittle, R. F., *Of URFS and ORFS—.a Primer on How to Analyze Derived Amino Acid Sequences*, University Science Books, Mill Valley, CA, 1986.

Deutscher, M.P., "Rethinking Your Purification Procedure." *Methods in Enzymology*, 182(57): 779-780, 1990.

Ellouz, S., et al., "Analytical Separation of *Trichoderma reesei* Cellulases by Ion-Exchange Fast Protein Liquid Chromatography." *J. Chromatography*, 396: 307-317, 1987.

Eriksson, A.E., et al., "Response of a Protein Structure to Cavity-Creating Mutations and Its Relation to the Hydrophobic Effect." *Science* 255: 178-183, 1992.

Fields, S., et al., "A novel genetic system to detect protein-protein interactions." *Nature* 340: 245-246, 1989.

Filho, E., "Purification and characterization of a β-glucosidase from solid-state cultures of *Humicola grisea* var. *thermoidea.*" *Can. J. Microbiol.* 42: 1-5, 1996.

Fliess, A. et al., "Characterization of Cellulases by HPLC Separation." *Eur. J. Appl. Microbiol. Biotechnol.* 17: 314-318, 1983.

Freer, S., "Kinetic Characterization of a β-Glucosidase from a Yeast, *Candida wickerhamii.*" *J. Biol. Chem.* 268(13): 9337-9342, 1993.

*Freshney, R.I., ed., *Animal Cell Culture: A Practical Approach*, IRL Press, Oxford, England, 1986.

Gloss, L.M., et al., "Urea and Thermal Equilibrium Denaturation Studies on the Dimerization Domain of *Escherichia coli* Trp Repressor." *Biochemistry* 36: 5612-5623, 1997.

Goedegebuur, F., et al., "Cloning and relational analysis of 15 novel fungal endoglucanases from family 12 glycosyl hydrolase." *Curr. Genet.* 41(2): 89-98, 2002.

Goldman, G.H., et al., "Transformation of *Trichoderma harzianum* by high-voltage electric pulse." *Curr. Genet.*, 17: 169-174, 1990.

Goyal, A., et al., "Characteristics of Fungal Cellulases." *Bioresource Technol.* 36: 37-50, 1991.

Gross, L.S., et al. "Changing the properties of *Hypocrea jecorina* Cel7A (*Trichoderma reesei* CBHI) by single amino acid mutations." *Biophys. J.*, 82 (Pt. 2): 459a, 2002.

Guo, H.H., et al., "Protein tolerance to random amino acid change." *Proc. Natl. Acad. Sci. USA*, 101(25): 9205-9210, 2004.

*Hale & Marham, *The Harper Collins Dictionary of Biology*, Harper Perennial, NY, 1991.

Halldorsdottir, S., et al., "Cloning, sequencing and overexpression of a *Rhodothermus marinus* gene encoding a thermostable cellulase of glycosyl hydrolase family 12." *Appl Microbiol Biotechnol.*, 49(3): 277-284, 1998.

Hemmpel, W.H., "The surface modification of woven and knitted cellulose fibre fabrics by enzymatic degradation." *ITB Dyeing/Printing/Finishing*, 3:5-14, 1991.

Henikoff, S., et al., "Amino acid substitution matrices from protein blocks." *Proc. Natl. Acad. Sci. USA.*, 89: 10915-10919, 1992.

Henrissat, B., et al., "New families in the classification of glycosyl hydrolases based on amino acid sequence similarities." *Biochem. J.*, 293: 781-788, 1993.

Herr, D., et al., "Purification and Properties of an Extracellular β-Glucosidase from *Lenzites trabea.*" *European Appl. Microbiol. Biotechnol.* 5: 29-36, 1978.

Higuchi, R., "Recombinant PCR." In *PCR Protocols: A guide to methods and applications*, M.A. Innis, et al., (eds.), pp. 177-183. Academic Press, San Diego, California, 1990.

Hopwood, D.A., et al., "Regulation of gene expression in antibiotic-producing *Streptomyces.*" In *Regulation of gene expression—25 years on*, I.R. Booth, et al., (eds.) pp. 251-276. 39th Symp. Soc. Gen. Microbiol., Cambridge University Press, Cambridge, England, 1986.

Hu, Q., et al., "Antibodies Specific for the Human Retinoblastoma Protein Identify a Family of Related Polypeptides." *Mol. Cell. Biol.*, 11(11): 5792-5799, 1991.

Hynes, M.J., et al., "Isolation of Genomic Clones Containing the amdS Gene of *Aspergillus nidulans* and Their Use in the Analysis of Structural and Regulatory Mutations." *Mol. Cell Biol.* 3(8): 1430-1439, 1983.

Ilmen, M., et al., "Regulation of Cellulase Gene Expression in the Filamentous Fungus *Trichoderma reesei.*" *Appl. Environ. Microbiol.*, 63(4): 1298-1306, 1997.

Jakobovits, A., et al., "Production of fully human antibodies by transgenic mice." *Curr. Opin. Biotechnol.* 6(5): 561-566, 1995.

Jakobovits, A., et al., "Production of Antigen-Specific Human Antibodies from Mice Engineered with Human Heavy and Light Chain YACs[a]." *Annals New York Academy of Sciences* 764: 525-535, 1995.

Jones, P.T. et al., "Replacing the complementarity—determining regions in a human antibody with those from a mouse." *Nature* 321: 522-525, 1986.

Karlin, S., et al., "Applications and statistics for multiple high-scoring segments in molecular sequences." *Proc. Nat'l. Acad. Sci. USA*, 90: 5873-5787, 1993.

Kawaguchi, T., et al., "Cloning and sequencing of the cDNA encoding β-glucosidase 1 from *Aspergillus aculeatus.*" *Gene* 173(2): 287-288, 1996.

Kellis, J.T., et al., "Contribution of hydrophobic interactions to protein stability." *Nature* 333: 784-786, 1988.

Knowles, J., et al., "Cellulase families and their genes." *TIBTECH*, 5: 255-261, 1987.

Köhler, G., et al., "Continuous cultures of fused cells secreting antibody of predefined specificity." *Nature*, 256: 495-497, 1975.

*Kriegler, M., *Gene Transfer and Expression: A Laboratory Manual*, New York, Stockton Press,1990.

Hari Krishna, S., et al., "Simultaneous saccharification and fermentation of lignocellulosic wastes to ethanol using a thermotolerant yeast." *Bioresource Tech.*, 77: 193-196, 2001.

Kumar, A., et al., "Optimizing the Use of Cellulase Enzymes in Finishing Cellulosic Fabrics." *Textile Chemist and Colorist*, 29: 37-42, 1997.

Kunkel, T.A., et al., "Rapid and efficient site-specific mutagenesis without phenotypic selection." *Proc. Natl. Acad. Sci. USA*, 82: 488-492, 1985.

Lehtio, J., et al., "Directed immobilization of recombinant staphylococci on cotton fibers by functional display of a fungal cellulose-binding domain." *FEMS Microbiology Letters* 195: 197-204, 2001.

Li, X.-L., et al. "Expression of *Aureobasidium pullulans xynA* in, and Secretion of the Xylanase from, *Saccharomyces cerevisiae.*" *Appl. Environ. Microbiol.* 62(1) : 209-213, 1996.

Linder, M., et al., "The roles and function of cellulose-binding domains." *Journal of Biotechnol.* 57: 15-28, 1997.

Lockington, R.A., et al. "Cloning and characterization of the ethanol utilization regulon in *Aspergillus nidulans.*" *Gene* 33, 137-149, 1985.

Lorito, M., et al., "Biolistic transformation of *Trichoderma harzianum* and *Gliocladium virens* using plasmid and genomic DNA." *Curr. Genet.* 24: 349-356, 1993.

Lund, H. et al., Search of Sequence 1, U.S. Appl. No. 09/069,632, Apr. 29, 1998.

Luo, J. et al.,"Detection of a Stable Intermediate in the Thermal Unfolding of a Cysteine-Free Form of Dihydrofolate Reductase from *Escherichia coli.*" *Biochemistry* 34: 10669-10675, 1995.

Matthews, B.W., "Structural and Genetic Analysis of Protein Stability." *Ann. Rev. Biochem.* 62:139-160, 1993.

Matthews, B.W., et al., "Enhanced protein thermostability from site-directed mutations that decrease the entropy of unfolding." *Proc. Natl. Acad. Sci. USA* 84; 6663-6667, 1987.

McKnight, G.L., et al., "Nucleotide Sequence of the Triosephosphate Isomerase Gene from *Aspergillus nidulans*: Implications for a Differential Loss of Introns." *Cell* 46, 143-147, 1986.

Medve, J., et al., "Ion-exchange chromatographic purification and quantitative analysis of *Trichoderma reesei* cellulases cellobiohydrolase I, II and endoglucanase II by fast protein liquid chromatography." *J. Chromatography* A 808: 153-165, 1998.

Miettinen-Oinonen, A, et al., Search of Sequence 33, U.S. Appl. No. 09/329,350, Jun. 10, 1999.

Mitsuishi, Y., et al., "Site-directed mutagenesis of the putative catalytic residues of *Trichoderma reesei* cellobiohydrolase I and endoglucanase I." *FEBS Lett.* 275: 135-138, 1990.

Mullaney, E.J., et al., "Primary structure of the *trpC* gene from *AspergiHus nidulans.*" *Mol. Gen. Genet.* 199, 37-45, 1985.

Needleman, S.B., et al., "A General Method Applicable to the Search for Similarities in the Amino Add Sequence of Two Proteins." *J. Mol. Biol.* 48: 443-453, 1970.

Nevalainen, H., et al., "Molecular Biology of Cellulolytic Fungi." In *The Mycota: A Comprehensive Treatise on Fungi as Experimental Systems, for Basic and Applied Research*, Esser, K., et al., eds., Springer-Verlag, pp. 303-319, Berlin, Heidelberg, Germany, 1995.

Nidetzky, B., et al., "Specific Quantification of *Trichoderma reesei* Cellulases in Reconstituted Mixtures and its Application to Cellulase-Cellulose Binding Studies." *Biotech Bioeng.* 44: 961-966, 1994.

Nunberg, J.H., et al. "Molecular Cloning and Characterization of the Glucoamylase Gene of *Aspergillus awamori*" *Mol. Cell. Biol.* 4(11), 2306-2315, 1984.

Ohmiya, K., et al., "Structure of Cellulases and Their Applications." In *Biotechnology and Genetic Engineering Reviews*, Tombs, M.P., ed., Intercept, Ltd., Andover, Hampshire, U.K., vol. 14, Chptr. 13, pp. 365-414, 1997.

Ooi, T., et al., "Complete nucleotide sequence of a gene coding for *Aspergillus aculeatus* cellulase (FI-CMCase)." *Nucl. Acids Res.* 18(19): 5884, 1990.

Ortega, N. et al., "Kinetics of cellulose saccharification by *Trichoderma reesei* cellulases." *International Biodeterioration & Biodegradation* 47: 7-14, 2001.

Pearson, W.R., et al., "Improved tools for biological sequence comparison." *Proc. Natl. Acad. Sci. USA* 85: 2444-2448, 1988.

Penttila, M., et al., "Efficient secretion of two fungal cellobiohydrolases by *Saccharomyces cerevisiae.*" *Gene*, 63: 103-112, 1988.

Penttila, M., et al., "Expression of Two *Trichoderma reesei* Endoglucanases in the Yeast *Saccharomyces cerevisiae.*" *Yeast* 3: 175-185, 1987.

Penttila, M., et al., "A versatile transformation system for the cellulolytic filamentous fungus *Trichoderma reesei.*" *Gene* 61: 155-164, 1987.

Pere, J., et al., "Use of Purified Enzymes in Mechanical Pulping." In *1996 Tappi Pulping Conference*, pp. 693-696, Nashville, TN, Oct. 27-31, 1996.

Pourquie, J. et al., "Scale Up of Cellulase Production and Utilization." In *Biochemistry and Genetics of Cellulose Degradation*, Aubert, J.P., et al., eds., Academic Press Limited, pp. 71-86, 1988.

Radford, A. et al., Search of Sequence 3, U.S. Appl. No. 08/676,166A, Jul. 15, 1996.

Riechmann, L., et al., "Reshaping human antibodies for therapy." *Nature*, 332: 323-327, 1988.

Rothstein, S.J., et al., "Synthesis and secretion of wheat α-amylase in *Saccharomyces cerevisiae.*" *Gene* 55: 353-356, 1987.

Russell, R.J.M., et al., "Engineering thermostability: lessons from thermophilic proteins." *Current Opinion in Biotechnology* 6: 370-374, 1995.

Saarilahti, H.T., et al., "CelS: a novel endoglucanase identified from *Erwinia carotovora* subsp. *carotovora.*" *Gene* 90: 9-14, 1990.

Sakamoto, S., et al., "Cloning and sequencing of cellulase cDNA from *Aspergillus kawachii* and its expression in *Saccharomyces cerevisiae.*" *Curr. Genet.* 27: 435-439, 1995.

Saloheimo M., et al., "EGIII, a new endoglucanase from *Trichoderma reesei*: the characterization of both gene and enzyme." *Gene*, 63: 11-22, 1988.

Saloheimo, M., et al. "cDNA cloning of a *Trichoderma reesei* cellulase and demonstration of endoglucanase activity by expression in yeast." *Eur. J. Biochem.* 249: 584-591, 1997.

*Sambrook et al., In *Molecular Cloning: A Laboratory Manual* (Second Edition), Cold Spring Harbor Press, Plainview, NY, 1989.

Schulein, M. et al., Search of Sequence 11, U.S. Appl. No. 08/709,974A, Sep. 9, 1996.

Schulein, M., "Cellulases of *Trichoderma reesei.*" In *Methods in Enzymology* vol. 160, No. 25, pp. 234-243, Academic Press Inc., 1988.

Scopes, R.K., et al., "Purification of All Glycolytic Enzymes from One Muscle Extract." In *Methods in Enzymology*, Wood, W.A., ed., vol. 90, Part E, No. 79, pp. 479-490, Academic Press Inc., 1982.

Seffernick, J.L., et al., "Melamine Deaminase and Atrazine Chlorohydrolase: 98 Percent Identical but Functionally Different." *J. Bacteriol.* 183(8): 2405-2410, 2001.

Sheir-Neiss, G., et al., "Characterization of the secreted cellulases of *Trichoderma reesei* wild type and mutants during controlled fermentations."*Appl. Microbiol. Biotechnol.* 20: 46-53, 1984.

Shoemaker S.P., et al., "Enzymic Activities of Endo-1,4-β-D-Glucanases Purified From *Trichoderma viride.*" *Biochim. Biophys. Acta* 523:133-146, 1978.

Shoemaker, S., et al., "Molecular Cloning of Exo-Cellobiohydrolase 1 Derived from *Trichoderma reesei* Strain L27." *Bio/Technology* 1: 691-696, 1983.

*Singleton, P., et al., *Dictionary of Microbiology and Molecular Biology*, 2d Ed., John Wiley and Sons, New York, 1994.

Smith, T.F., et al., "Comparison of Biosequences." *Adv. Appl. Math.* 2: 482-489, 1981.

Spilliaert, R., et al., "Cloning and sequencing of a *Rhodothermus marinus* gene, *bglA*, coding for a thermostable β-glucanase and its expression in *Escherichia coli.*" *Eur. J. Biochem.* 224(3): 923-930, 1994.

Srisodsuk, M., et al., "*Trichoderma reesei* cellobiohydrolase I with an endoglucanase cellulose-binding domain: action on bacterial microcrystalline cellulose." *J. Biotech.* 57: 49-57, 1997.

Stahlberg, J., et al., "A New Model for Enzymatic Hydrolysis of Cellulose Based on the Two-Domain Structure of Cellobiohydrolase I." *Bio/Technol.* 9: 286-290, 1991.

*Strathern, J.N., et al., eds. *The Molecular Biology of the Yeast Saccharomyces: Life Cycle and Inheritance*, Cold Spring Harbor, 1981.

Suurnakki, A., et al., "*Trichoderma reesei* cellulases and their core domains in the hydrolysis and modification of chemical pulp." *Cellulose* 7: 189-209, 2000.

Tanner, J.J., et al., "Determinants of Enzyme Thermostability Observed in the Molecular Structure of *Thermus aquaticus* D-Glyceraldehyde-3-phosphate Dehydrogenase at 2.5 Å Resolution." *Biochemistry* 35: 2597-2609, 1996.

Teeri, T.T., et al., "Homologous domains in *Trichoderma reesei* cellulolytic enzymes: gene sequence and expression of cellobiohydrolase II." *Gene*, 51: 43-52, 1987.

Te'o, V.S.J., et al., "Codon optimization of xylanase gene *xynB* from the thermophilic bacterium *Dictyoglomus thermophilum* for expression in the filamentous fungus *Trichoderma reesei.*" *FEMS Microbiology Letters*, 190:13-19, 2000.

Thompson, J.D., et al., "CLUSTAL W: improving the sensitivity of progressive multiple sequence alignment through sequence weighting, position-specific gap penalties and weight matrix choice." *Nucleic Acid Research* 22(22): 4673-4680, 1994.

Timberlake, W.E., et al., "Organization of a Gene Cluster Expressed Specifically in the Asexual Spores of *A. nidulans.*" *Cell*, 26: 29-37, 1981.

Tomaz, C. et al., "Studies on the chromatographic fractionation of *Trichoderma reesei* cellulases by hydrophobic interaction." *J. Chromatography A* 865: 123-128, 1999.

Tomme, P., et al., "Studies of the cellulolytic system of *Trichoderma reesei* QM 9414." *Eur. J. Biochem.* 170: 575-581, 1988.

Tormo, J., et al., "Crystal structure of a bacterial family-III cellulose-binding domain: a general mechanism for attachment to cellulose." *EMBO J.* 15(21): 5739-5751, 1996.

Tyndall, R.M., "Improving the Softness and Surface Appearance of Cotton Fabrics and Garments by Treatment with Cellulase Enzymes." *Textile Chemist and Colorist* 24(6): 23-26, 1992.

Vallette, F., et al., "Construction of mutant and chimeric genes using the polymerase chain reaction." *Nuc. Acids Res.* 17(2): 723-733, 1989.

Van Den Hondel, C.A.M.J.J., et al., "Heterologous Gene Expression in Filamentous Fungi." In *More Gene Manipulations in Fungi*, Bennett, J.W., et al., (eds.). Academic Press Inc., pp. 396-428, 1991.

Van Hartingsveldt, W., et al., "Development of a homologous transformation system for *Aspergillus niger* based on the *pyrG* gene." *Mol. Gen. Genet.* 206: 71-75, 1986.

Van Rensburg, P., et al., "Engineering Yeast for Efficient Cellulose Degradation." *Yeast* 14: 67-76, 1998.

Van Tilbeurgh, H. et al., "Limited proteolysis of the cellobiohydrolase I from *Trichoderma reesei*: Separation of functional domains." *FEBS Lett.* 204(2): 223-227, 1986.

Van Tilbeurgh, H., et al., "Separation of endo- and exo-type cellulases using a new affinity chromatography method." *FEBS Lett.* 169(2): 215-218, 1984.

Verhoeyen, M., et al., "Reshaping Human Antibodies: Grafting an Antilysozyme Activity." *Science* 239:1534-1536, 1988.

Von Der Osten, C., et al., Search of Sequence 1, U.S. Appl. No. 08/709,979A, Sep. 9, 1996.

Ward, M., et al., "Use of *Aspergillus* overproducing mutants, cured for integrated plasmid, to overproduce heterologous proteins." *Appl. Microbiol. Biotechnol.* 39: 738-743, 1993.

Warrington, J.A., et al. "A Radiation Hybrid Map of 18 Growth Factor, Growth Factor Receptor, Hormone Receptor, or Neurotransmitter Receptor Genes on the Distal Region of the Long Arm of Chromosome 5." *Genomics*, 13 : 803-808, 1992.

Watanabe, K., et al., "Multiple proline substitutions cumulatively thermostabilize *Bacillus cereus* ATCC7064 oligo-1,6-glucosidase: Irrefragable proof supporting the proline rule." *Eur. J. Biochem.* 226: 277-283, 1994.

Wells, J.A. et al., "Importance of hydrogen-bond formation in stabilizing the transition state of subtilisin." *Phil. Trans. R. Soc. London* A. 317: 415-423, 1986.

Wells, J.A., et al., "Cassette mutagenesis: an efficient method for generation of multiple mutations at defined sites." *Gene*, 34: 315-323, 1985.

Witkowski, A., et al., "Conversion of a β-ketoacyl synthase to a malonyl decarboxylase by replacement of the active-site cysteine with glutamine." *Biochemistry* 38(36): 11643-11650, 1999.

Wood, T.M., et al., "Methods for Measuring Cellulase Activities." in *Methods in Enzymology*, vol. 160, No. 9, pp. 87-112, New York, Academic Press, Inc., 1988.

Wood, T.M., "Properties of cellulolytic enzyme systems." In *Biochemical Society Transactions*, London: The Biochemical Society, 611$^{th}$ Meeting, Galway; Moreland, B., 1985 ed., vol. 13, Part 2, pp. 407-410, 1985.

Yamagishi, M., "Reforming of Cellulosic Fiber With Cellulase." In *The Shizuoka Prefectural Hamamatsu Textile Industrial Research Institute Report*, vol. 24: pp. 54-61, 1986.

Yelton, M.M., et al., "Transformation of *Aspergillus nidulans* by using a *trpC* plasmid." *Proc. Natl. Acad. Sci. USA* 81: 1470-1474, 1984.

Zoller, M.J., et al., "Oligonucleotide-directed mutagenesis using M13-derived vectors: an efficient and general procedure for the production of point mutations in any fragment of DNA." *Nucleic Acids Research* 10(20): 6487-6500, 1982.

Zuber, H., "Temperature adaptation of lactate dehydrogenase: Structural, functional and genetic aspects." *Biophys. Chem.* 29: 171-179, 1988.

International Search Report and the Written Opinion of the International Searching Authority for International Application No. PCT/US2004/008520, dated Jun. 29, 2006.

Supplementary European Search Report for European Patent Application No. 04809323.1, dated Sep. 17, 2007.

Supplementary Partial European Search Report for European Patent Application No. 04809323.1, dated Jun. 12, 2007.

* cited by examiner

Amino Acid and Nucleic Acid Sequence of *Hypocrea jecorina* Cel7A

```
     GlnSerAlaCys ThrLeuGln SerGluThr HisProProLeu ThrTrpGln LysCysSer SerGlyGlyThr CysThrGln GlnThrGly SerValValIle.
  1  CAGTCGGCCT GCACTCTCCA ATCGGAGACT CACCCGCCCTC TGACATGGCA GAAATGCTCG TCTGGTGGCA CTTGCACTCA ACAGACAGGC TCCGTGGTCA

.IAspAlaAsn TrpArgTrp ThrHisAlaThr AsnSerSer ThrAsnCys TyrAspGlyAsn ThrTrpSer SerThrLeu CysProAspAsn GluThrCys.
 101 TCGACGCCAA CTGGCGCTGG ACTCACGCTA CGAACAGCAG CACGAACTGC TACGACGGCA ACACTTGGAG CTCGACCCTA TGTCCTGACA ACGAGACCTG

.AlaLysAsn CysCysLeuAsp GlyAlaAla TyrAlaSer ThrTyrGlyVal ThrThrSer GlyAsnSer LeuSerIleGly PheValThr GlnSerAla
 201 CGCGAAGAAC TGCTGTCTGG ACGGTGCCGC CTACGCGTCC ACGTACGGAG TTACCACGAG CGGTAACAGC CTCTCCATTG GCTTTGTCAC CCAGTCTGCG

GlnLysAsnVal GlyAlaArg LeuTyrLeu MetAlaSerAsp ThrThrTyr GlnGluPhe ThrLeuLeuGly AsnGluPhe SerPheAsp ValAspValSer.
 301 CAGAAGAACG TTGGCGCTCG CCTTTACTT ATGGCGAGCG ACACGACCTA CCAGGAATTC ACCCTGCTTG GCAACGAGTT CTCTTTCGAT GTTGATGTTT

.SGlnLeuPro CysGlyLeu AsnGlyAlaLeu TyrPheVal SerMetAsp AlaAspGlyGly ValSerLys TyrProThr AsnThrAlaGly AlaLysTyr.
 401 CGCAGCTGCC GTGCGGCTTG AACGGAGCTC TCTACTTCGT GTCCATGGAC GCGGATGGTG GCGTGAGCAA GTATCCCACC AACACCGCTG GCGCCAAGTA

.GlyThrGly TyrCysAspSer GlnCysPro ArgAspLeu LysPheIleAsn GlyGlnAla AsnValGlu GlyTrpGluPro SerSerAsn AsnAlaAsn
 501 TGGCACGGGG TACTGTGACA GCCAGTGTCC CCGGGATCTG AAGTTCATCA ATGGCCAGGC CAACGTTGAG GGCTGGGAGC CGTCATCCAA CAACGCGAAC

ThrGlyIleGly GlyHisGly SerCysCys SerGluMetAsp IleTrpGlu AlaAsnSer IleSerArgAla LeuThrPro HisProCys ThrThrValGly.
 601 ACGGGCCATTG GAGGACACGG AAGCTGCTGC TCTGAGATGG ATATCTGGGA GGCCAACTCC ATCTCCGAGG CTCTTACCCC CCACCCTTGC ACGACTGTCG

.GGlnGluIle CysGluGly AspGlyCysGly GlyThrTyr SerAspAsn ArgTyrGlyGly ThrCysAsp ProAspGly CysAspTrpAsn ProTyrArg.
 701 GCCAGAGAT CTGCGAGGGT GATGGGTGCG GCGGAACTTA CTCCGATAAC AGATATGGCG GCACTTGCGA TCCCGATGGC TGCGACTGGA ACCCATACCG

.LeuGlyAsn ThrSerPheTyr GlyProGly SerSerPhe ThrLeuAspThr ThrLysLys LeuThrVal ValThrGlnPhe GluThrSer GlyAlaIle
 801 CCTGGGCAAC ACCAGCTTCT ACGGCCCTGG CTCAAGCTTT ACCCTCGATA CCACCAAGAA ATTGACCGTT GTCACCCAGT TCGAGACGTC GGGTGCCATC

AsnArgTyrTyr ValGlnAsn GlyValThr PheGlnGlnPro AsnAlaGlu LeuGlySer TyrSerGlyAsn GluLeuAsn AspAspTyr CysThrAlaGlu.
 901 AACCGATACT ATGTCCAGAA TGGCGTCACT TTCCAGCAGC CCAACGCCGA GCTTGGTAGT TACTCTGGCA ACGAGCTCAA CGATGATTAC TGCACAGCTG

.GGluAlaGlu PheGlyGly SerSerPheSer AspLysGly GlyLeuThr GlnPheLysLys AlaThrSer GlyGlyMet ValLeuValMet SerLeuTrp.
1001 AGGAGGCAGA ATTCGGCCGA TCCTCTTTCT CAGACAAGGG CGGCCTGACT CAGTTCAAGA AGGCTACCTC TGGCGGCATG GTTCTGGTCA TGAGTCTGTG

.AspAspTyr TyrAlaAsnMet LeuTrpLeu AspSerThr TyrProThrAsn GluThrSer SerThrPro GlyAlaValArg GlySerCys SerThrSer
1101 GGATGATTAC TACGCCAACA TGCTCTGGCT GGACTCCACT TACCCGACAA ACGAGACCTC CAGTTCACCC GGTGCCGTGC GCGGAAGCTG CTCCACCAGC

SerGlyValPro AlaGlnVal GluSerGln SerProAsnAla LysValThr PheSerAsn IleLysPheGly ProIleGly SerThrGly AsnProSerGly.
1201 TCCGGTGTCC CTGCTCAGGT CGAAATTCAG AGTCCCAACG CTTCCTCAAC ATCAAGTTCG GACCCATTGG CAGCACCGGC AACCCTAGCG

.GGlyAsnPro ProGlyGly AsnProProGly AsnProArg ThrThrThr ThrArgArgPro AlaThrThr ThrGlySer SerProGly ProThrGlnSer HisTyrGly.
1301 GCGGCAACCC TCCCGGCGGA AACCCGCCTG GCAACCCACGA CCACCACCAC CACCACCACC GCCGCCGCCCA CCTCCCCGGA AGCTCGAAG CTCCCCCAGT CTCACTACGG

.GlnCysGly GlyIleGlyTyr SerGlyPro ThrValCys AlaSerGlyThr ThrCysGln ValLeuAsn ProTyrTyrSer GlnCysLeu
1401 CCAGTGCGGC GGTATTGGCT ACAGCGGCCC CACGGTTGCA GCCAGCGGCA CAACTTGCCA GGTCCTGAAC CCTTACTACT CTCAGTGCCT G
```

FIG._1

Multiple Alignment of the CBH1 Homologous Sequences

```
                          1                                                            50
T reesei mat        (1)   QSACTLQSETHPPLTWQKCSSGGTCTQQTGSVVIDANWRWTHATNSSTNC
H orientalis mat    (1)   QSACTLQTETHPSLTWQKCSSGGTCTQQTGSVVIDANWRWTHATNSSTNC
H schweinitzii mat  (1)   QSACTLQTETHPSLTWQKCSSGGTCTQQTGSVVIDANWRWTHATNSSTNC
T. koninlangbra mat (1)   QSACTIQAETHPPLTWQKCSSGGSCTSQTGSVVIDANWRWTHATNSTTNC
T. pseudokoningii mat (1) QSACTLQTETHPPLTWQKCSSGGTCTQQTGSVVIDANWRWTHATNSSTNC
Consensus           (1)   QSACTLQTETHPPLTWQKCSSGGTCTQQTGSVVIDANWRWTHATNSSTNC 51                                                           100
T reesei mat        (51)  YDGNTWSSTLCPDNETCAKNCCLDGAAYASTYGVTTSGNSLSIGFVTQSA
H orientalis mat    (51)  YDGNTWSSTLCPDNETCAKNCCLDGAAYASTYGVTTSADSLSIGFVTQSA
H schweinitzii mat  (51)  YDGNTWSSELCPDNETCAKNCCLDGAAYASTYGVTTSADSLSIGFVTQSA
T. koninlangbra mat (51)  YDGNTWSSLCPDNESCAKNCCLDGAAYASTYGVTTSADSLSIGFVTQSA
T. pseudokoningii mat (51) YDGNTWSSTLCPDNETCAKNCCLDGAAYASTYGVTTSADSLSIGFVTQSQ
Consensus           (51)  YDGNTWSSTLCPDNETCAKNCCLDGAAYASTYGVTTSADSLSIGFVTQSA 101                                                          150
T reesei mat        (101) QKNVGARLYLMASDTTYQEFTLLGNEFSFDVDVSQLPCGLNGALYFVSMD
H orientalis mat    (101) QKNVGARLYLMASDTTYQEFTLLGNEFSFDVDVSQLPCGLNGALYFVSMD
H schweinitzii mat  (101) QKNVGARLYLMASDTTYQEFTLLGNEFSFDVDVSQLPCGLNGALYFVSMD
T. koninlangbra mat (101) QKNVGARLYLMASDTTYQEFTLLGNEFSFDVDVSQLPCGLNGALYFVSMD
T. pseudokoningii mat (101) QKNVGARLYLMASDTTYQEFTLLGNEFSFDVDVSQLPCGLNGALYFVSMD
Consensus           (101) QKNVGARLYLMASDTTYQEFTLLGNEFSFDVDVSQLPCGLNGALYFVSMD 151                                                          200
T reesei mat        (151) ADGGVSKYPTNTAGAKYGTGYCDSQCPRDLKFINGQANVEGWEPSSNNAN
H orientalis mat    (151) ADGGVSKYPTNTAGAKYGTGYCDSQCPRDLKFINGQANVEGWEPSSNNAN
H schweinitzii mat  (151) ADGGVSKYPTNTAGAKYGTGYCDSQCPRDLKFINGQANVEGWEPSSNNAN
T. koninlangbra mat (151) ADGGVSKYPSNTAGAKYGTGYCDSQCPRDLKFINGEANVEGWEPASNNAN
T. pseudokoningii mat (151) ADGGVSKYPTNTAGAKYGTGYCDSQCPRDLKFINGQANVEGWEPFSNNAN
Consensus           (151) ADGGVSKYPTNTAGAKYGTGYCDSQCPRDLKFINGQANVEGWEPSSNNAN
```

FIG._2A

Multiple Alignment of the CBH1 Homologous Sequences

```
                          201
T reesei mat       (201)  TGIGGHGSCCSEMDIWEANSISEALTPHPCTTVGQEICEGDGCGGTYSDN
H orientalis mat   (201)  TGIGGHGSCCSEMDIWEANSISEALTPHPCTTVGQEICDGDGCGGTYSND
H schweinitzii mat (201)  TGIGGHGSCCSEMDIWEANSISEALTPHPCTNVGQEICDGDGCGGTYSND
T. koninlangbra mat(201)  TGIGGHGSCCSEMDIWEANSISEALTPHPCTTVGQAICDGDGCGGTYSDD
T. pseudokoningii mat(201)TGIGGHGSCCSEMDIWEANSISEALTPHPCTTVGQEICDGDSCGGTYSGD
Consensus          (201)  TGIGGHGSCCSEMDIWEANSISEALTPHPCTTVGQEICDGDGCGGTYSGD 251                                                300
T reesei mat       (251)  RYGGTCDPDGCDWNPYRLGNTSFYGPGSSFTLDTTKKLTVVTQFETSGAI
H orientalis mat   (251)  RYGGTCDPDGCDWNPYRLGNTSFYGPGSSFTLDTTKKLTVVTQFETSGAI
H schweinitzii mat (251)  RYGGTCDPDGCDWNPYRLGNTSFYGPGSSFTLDTTKKLTVVTQFETSGAI
T. koninlangbra mat(251)  RYGGTCDPDGCDWNPYRLGNTSXYGPGSSFTLDTTKKMTVVTQFATSGAI
T. pseudokoningii mat(251)RYGGTCDPDGCDWNPYRLGNTSFYGPGSSFALDTTKKLTVVTQFETSGAI
Consensus          (251)  RYGGTCDPDGCDWNPYRLGNTSFYGPGSSFTLDTTKKLTVVTQFETSGAI 301                                                350
T reesei mat       (301)  NRYYVQNGVTFQQPNAELGSYSGNELNDDYCTAEEAEFGGSSFSDKGGLT
H orientalis mat   (301)  NRYYVQNGVTFQQPNAELGSYSGNELNDDYCTAEEAEFGGSSFSDKGGLT
H schweinitzii mat (301)  NRYYVQNGVTFQQPNAELGSYSGNELNDAYCTAEEAEFGGSSFSDKGGLT
T. koninlangbra mat(301)  NRYYVQNGVTFQQPNAELGSYSGNTLNDAYCAAEEAEFGGSSFSDKGGLT
T. pseudokoningii mat(301)NRYYVQNGVTFQQPNAELGSYSGNSLDDYCAAEAEFGGSSFSDKGGLT
Consensus          (301)  NRYYVQNGVTFQQPNAELGSYSGNELNDDYCTAEEAEFGGSSFSDKGGLT 351                                                400
T reesei mat       (351)  QFKKATSGGMVLVMSLWDDYYANMLWLDSTYPTNETSSTPGAVRGSCSTS
H orientalis mat   (351)  QFKKATSGGMVLVMSLWDDYYANMLWLDSTYPTNETSSTPGAVRGSCSTS
H schweinitzii mat (351)  QFKKATSGGMVLVMSLWDDYYANMLWLDSTYPTNETSSTPGAVRGSCSTS
T. koninlangbra mat(351)  QFKQATSGGMVLVMSLWDDYYANMLWLDSIYPTNETSSTPGAARGSCSTS
T. pseudokoningii mat(351)QFKKATSGGMVLVMSLWDDYYANMLWLDSIYPTNETSSTPGARGSCSTS
Consensus          (351)  QFKKATSGGMVLVMSLWDDYYANMLWLDSTYPTNETSSTPGAVRGSCSTS
```

FIG._2B

Multiple Alignment of the CBH1 Homologous Sequences

```
                         401
T reesei mat       (401) SGVPAQVESQSPNAKVTFSNIKFGPIGSTGNPSGGNPPGG-NPPGTTTTR
H orientalis mat   (401) SGVPAQLESQSPNAKVVYSNIKFGPIGSTGNPSGGNPPGG-NPPGTTTTR
H schweinitzii mat (401) SGVPAQLESQSANAKVVYSNIKFGPIGSTGNPSGGNPPGG-NPPGTTTTR
T. koninlangbra mat(401) SGVPAQLESQSTNAKVVFSNIKFGPIGSTGNSSGGNPPGGGNPPGTTTTR
T. pseudokoningii mat(401) SGVPAQLESQSSNAKVVYSNIKFGPIGSTGNSSGGSPPGGGNPPGTTTTR
Consensus          (401) SGVPAQLESQS NAKVVYSNIKFGPIGSTGNPSGGNPPGG NPPGTTTTR 451                                              499
T reesei mat       (450) RPATTTGSSPGPTQSHYGQCGGIGYSGPTVCASGTTCQ-VLNPYYSQCL
H orientalis mat   (450) RPATTTGSSPGPTQTHYGQCGGIGYSGPTVCASGTTCQ-VLNPYYSQCL
H schweinitzii mat (450) RPATTTGSSPGPTQTHYGQCGGIGYSGPTVCASGTTCQ-QVLNEYYSQCL
T. koninlangbra mat(451) RPATTTGSSPGPTQTHYGQCGGIGYSGPTICASGTTCQ-VLNEYYSQCL
T. pseudokoningii mat(451) RPATSTGSSPGPTQTHYGQCGGIGYSGPTVCASGSTCQ-VLNEYYSQCL
Consensus          (451) RPATTTGSSPGPTQTHYGQCGGIGYSGPTVCASGTTCQ  VLNEYYSQCL
```

*FIG._2C*

H. orientalis Genomic DNA Sequence

```
CGTCATCTCG GCCTTCTTGG CCACGGCCCG TGCTCAGTCG GCCTGCACTC    50
TCCAAACGGA GACTCACCCG TCTCTGACAT GGCAGAAATG CTCGTCTGGC   100
GGCACTTGCA CCCAGCAGAC AGGCTCCGTG GTCATCGACG CCAACTGGCG   150
CTGGACTCAC GCGACTAACA GCAGCACGAA CTGCTACGAC GGCAACACTT   200
GGAGCTCAAC CCTATGCCCT GACAACGAGA CTTGCGCGAA GAATTGCTGC   250
CTGGACGGTG CCGCCTATGC GTCCACGTAC GGAGTCACCA CGAGTGCCGA   300
CAGCCTCTCC ATCGGCTTCG TCACGCAATC TGCACAGAAG AACGTTGGCG   350
CCCGTCTCTA CCTGATGGCG AGTGACACGA CTTACCAGGA GTTCACGCTG   400
CTTGGCAACG AGTTCTCTTT TGACGTTGAT GTTTCGCAGC TGCCGTAAGT   450
GACAACCATT CCCCGCGAGG CCATCTTCTC ATTGGTTCCG AGCTGACCCG   500
CCGATCTAAG ATGTGGCTTG AACGGCGCTC TGTACTTCGT GTCTATGGAT   550
GCGGATGGTG GCGTGAGCAA GTATCCCACC AACACCGCCG GCGCCAAGTA   600
CGGCACGGGC TACTGCGACA GCCAGTGCCC CCGCGATCTC AAGTTCATCA   650
ACGGCCAGGC CAACGTTGAA GGCTGGGAGC CGTCCTCCAA CAACGCCAAC   700
ACGGGTATTG GCGGACACGG AAGCTGCTGC TCTGAGATGG ATATCTGGGA   750
GGCCAACTCC ATCTCCGAGG CTCTGACTCC TCACCCTTGC ACGACTGTTG   800
GCCAGGAGAT CTGCGACGGT GACGGCTGCG GCGGAACCTA CTCCAACGAC   850
CGATATGGTG GTACTTGCGA TCCTGATGGT TGTGATTGGA ATCCATACCG   900
CTTGGGCAAC ACCAGCTTCT ATGGCCCTGG CTCGAGCTTC ACCCTCGATA   950
CCACCAAGAA GTTGACCGTT GTCACCCAGT TCGAGACCTC GGGTGCCATC  1000
AACCGTTACT ATGTCCAGAA CGGCGTCACT TACCAGCAAC CCAACGCCGA  1050
GCTCGGTAGT TACTCTGGTA ATGAGCTCAA CGATGACTAC TGCACAGCTG  1100
AGGAGTCGGA ATTCGGCGGC TCCTCCTTCT CGGACAAGGG CGGCCTTACT  1150
CAGTTCAAGA AGGCCACTTC CGGCGGCATG GTCCTGGTCA TGAGCTTGTG  1200
GGATGACGTG AGTTGATAGA CAGCATTCAC ATTGTCGTTG GAAAGACGGG  1250
CGGCTAACCG AGACATATGA TATCTAACAG TACTACGCCA ACATGCTGTG  1300
GCTGGACTCC ACCTACCCGA CAAACGAGAC CTCCTCCACC CCCGGCGCCG  1350
TGCGCGGAAG CTGCTCCACC AGCTCCGGCG TCCCCGCTCA GCTCGAGTCC  1400
CAGTCCCCCA ACGCCAAGGT CGTCTACTCC AACATCAAGT TCGGGCCCAT  1450
TGGCAGCACC GGCAACCCCA GCGGCGGAAA CCCTCCTGGC GGAAACCCTC  1500
CCGGCACCAC CACCACCCGC CGCCCAGCTA CCACCACTGG AAGCTCTCCC  1550
GGACCTACTC AGACTCACTA CGGCCAGTGC GGCGGCATCG GCTACAGCGG  1600
CCCTACGGTC TGCGCCAGCG GCACGACCTG CCAGG                  1635
```

FIG._3

H. orientalis Amino Acid Signal Sequence

```
MYRKLAVISA FLATARA                                       17
```

FIG._4A

H. orientalis Mature Amino Acid Sequence

```
QSACTLQTET HPSLTWQKCS SGGTCTQQTG SVVIDANWRW THATNSSTNC    50
YDGNTWSSTL CPDNETCAKN CCLDGAAYAS TYGVTTSADS LSIGFVTQSA   100
QKNVGARLYL MASDTTYQEF TLLGNEFSFD VDVSQLPCGL NGALYFVSMD   150
ADGGVSKYPT NTAGAKYGTG YCDSQCPRDL KFINGQANVE GWEPSSNNAN   200
TGIGGHGSCC SEMDIWEANS ISEALTPHPC TTVGQEICDG DCGGTYSND    250
RYGGTCDPDG CDWNPYRLGN TSFYGPSSF TLDTTKKLTV VTQFETSGAI    300
NRYYVQNGVT YQQPNAELGS YSGNELNDDY CTAEESEFGG SSFSDKGGLT   350
QFKKATSGGM VLVMSLWDDY YANMLWLDST YPTNETSSTP GAVRGSCSTS   400
SGVPAQLESQ SPNAKVVYSN IKFGPIGSTG NPSGGNPPGG NPPGTTTTRR   450
PATTTGSSPG PTQTHYGQCG GIGYSGPTVC ASGTTCQVLN PYYSQCL      497
```

FIG._4B

H. schweinitzii Genomic DNA Sequence

```
TCGGCCTGCA CTCTCCAAAC GGAGACTCAC CCGTCTCTGA CATGGCAGAA     50
ATGCTCGTCT GGCGGCACTT GCACCCAGCA GACAGGCTCC GTGGTCATCG    100
ACGCCAACTG GCGCTGGACT CACGCTACTA ACAGCAGCAC GAACTGCTAC    150
GACGGCAACA CTTGGAGCTC AACCCTGTGC CCTGACAATG AGACTTGCGC    200
GAAGAACTGC TGCCTGGACG GTGCCGCCTA TGCGTCCACG TACGGAGTCA    250
CCACGAGTGC CGACAGCCTC TCCATCGGCT TCGTGACACA GTCTGCACAG    300
AAAAACGTTG GCGCCCGTCT CTACCTGATG GCGAGTGACA CGACTTACCA    350
GGAGTTCACG CTGCTTGGCA ACGAGTTCTC ATTCGACGTT GATGTTTCGC    400
AGCTGCCGTA AGTGACAACC ATTCCCCCGA CGCCATCTTC TCATTGGTTC    450
GAAGCTGACC CGCCGATCTA AGATGGCT TGAACGGCGC TCTTTACTTC       500
GTGTCCATGG ACGCAGATGG TGGCGTGAGC AAGTATCCCA CCAACACCGC    550
CGGCGCCAAG TACGGCACGG GCTACTGTGA CAGCCAGTGC CCCCGCGATC    600
TCAAGTTTAT CAACGGCCAG GCCAACGTTG AAGGCTGGGA GCCGTCCTCC    650
AACAACGCCA ACACGGGTAT TGGCGGACAC GGAAGCTGCT GCTCCGAGAT    700
GGATATCTGG GAGGCCAACT CCATCTCCGA GGCTCTTACT CCTCACCCTT    750
GCACGAATGT TGGCCAGGAG ATCTGCGACG GTGACGGCTG CGGCGGAACC    800
TACTCCAACG ACCGATATGG TGGTACTTGC GATCCTGATG GTTGTGATTG    850
GAATCCATAC CGCTTGGGCA ACACCAGCTT CTATGGCCCT GGCTCGAGCT    900
TCACCCTCGA TACCACCAAG AAGTTGACCG TCGTCACCCA GTTCGAGACT    950
TCGGGTGCCA TCAACCGTTA CTATGTCCAG AATGGCGTCA CTTACCAGCA   1000
ACCCAACGCC GAGCTCGGCA GTTACTCTGG TAATGAGCTC AACGATGCCT   1050
ACTGCACAGC TGAAGAGTCG GAATTTGGCG GTTCCTCCTT CTCGGACAAG   1100
GGCGGCCTTA CTCAGTTCAA GAAGGCCACT TCCGGCGGCA TGGTCCTGGT   1150
CATGAGCTTG TGGGATGACG TGAGTCCATA GAACAGCATT CACATTGTCG   1200
TCGGAAAGAC GGCCGGCTAA CCGAGACATT ACAGTACTAC GCCAACATGC   1250
TGTGGCTGGA CTCCACCTAC CCGACAAACG AGACCTCCTC CACCCCCGGT   1300
GCCGTGCGCG GAAGCTGCTC CACCAGCTCC GGCGTCCCAG CTCAGCTCGA   1350
GTCCAGTCC GCCAACGCCA AGGTCGTCTA CTCCAACATC AAGTTCGGAC    1400
CCATTGGCAG CACCGGCAAC CCCAGCGGCG GAAACCCTCC TGGCGGAAAC   1450
CCTCCCGGCA CCACCACCAC CCGCCGCCCA GCTACCACCA CTGGAAGCTC   1500
TCCCGGACCT ACTCAGACTC ACTATGGCCA GTGCGGCGGC ATCGGCTACA   1550
GCGGCCCTAC GATCTGCGCC AGCGGCACGA CCTGCCAGG               1589
```

FIG._5

H. Schweinitzii Signal Peptide

```
MYRKLAVITA FLATARA                                         17
```

FIG._6A

H. Schweinitzii Mature Amino Acid Sequence
497 Residues

```
QSACTLQTET HPSLTWQKCS SGGTCTQQTG SVVIDANWRW THATNSSTNC     50
YDGNTWSSTL CPDNETCAKN CCLDGAAYAS TYGVTTSADS LSIGFVTQSA    100
QKNVGARLYL MASDTTYQEF TLLGNEFSFD VDVSQLPCGL NGALYFVSMD    150
ADGGVSKYPT NTAGAKYGTG YCDSQCPRDL KFINGQANVE GWEPSSNNAN    200
TGIGGHGSCC SEMDIWEANS ISEALTPHPC TNVGQEICDG DGCGGTYSND    250
RYGGTCDPDG CDWNPYRLGN TSFYGPSSF TLDTTKKLTV VTQFETSGAI     300
NRYYVQNGVT YQQPNAELGS YSGNELNDAY CTAEESEFGG SSFSDKGGLT    350
QFKKATSGGM VLVMSLWDDY YANMLWLDST YPTNETSSTP GAVRGSCSTS    400
SGVPAQLESQ SANAKVVYSN IKFGPIGSTG NPSGGNPPGG NPPGTTTTRR    450
PATTTGSSPG PTQTHYGQCG GIGYSGPTIC ASGTTCQVLN PYYSQCL       497
```

FIG._6B

T. konilangbra Genomic DNA

```
TCGGCCTGCA CCATTCAAGC GGAGACTCAC CCGCCTCTGA CATGGCAGAA    50
ATGCTCATCC GGTGGTAGTT GCACCTCGCA AACCGGTTCT GTGGTGATTG   100
ACGCGAACTG GCGATGGACT CACGCGACTA ACAGCACCAC GAACTGCTAC   150
GACGGTAACA CTTGGAGCTC CAGTCTTTGC CCCGACAATG AGAGTTGCGC   200
AAAGAACTGC TGCCTGGACG GTGCAGCCTA CGCATCCACG TACGGAGTCA   250
CCACGAGTGC TGATAGCCTC TCCATTGGCT TCGTCACTCA GTCTCAGCAG   300
AAGAATGTTG GCGCTCGTCT CTACCTGATG GCAAGCGACA CGACCTACCA   350
GGAATTTACC CTGCTTGGCA ACGAGTTCTC TTTCGATGTT GATGTTTCAC   400
AGCTGCCGTA AGTGACTAGC ATTTACCTCC GACGCCATCT CATTGATTCC   450
CAGCTGACGG CCAATTCAAG ATGTGGCTTG AACGGAGCCC TTTACTTCGT   500
GTCCATGGAC GCGGATGGTG GCGTGAGCAA GTATCCCTCC AACACTGCCG   550
GCGCCAAGTA CGGCACGGGC TACTGCGATA GCCAGTGTCC CCGTGATTTG   600
AAGTTCATCA ACGGCGAGGC CAACGTTGAG GGCTGGGAGC CGGCTTCGAA   650
CAACGCCAAC ACGGGTATTG GCGGACACGG AAGCTGCTGC TCTGAGATGG   700
ATATCTGGGA GGCCAACTCC ATCTCTGAGG CCCTTACTCC TCACCCTTGC   750
ACGACTGTCG GCCAGGCCAT TTGCGATGGT GACGGCTGCG GTGGAACCTA   800
CTCCGATGAC CGATATGGTG GTACTTGCGA TCCTGATGGC TGTGACTGGA   850
ACCCATACCG CTTGGGCAAC ACCAGCTTCT ACGGCCCCGG CTCGAGCTTC   900
ACCCTCGACA CCACCAAGAA GATGACCGTC GTCACCCAGT TCGCTACTTC   950
GGGTGCCATC AACCGATACT ATGTCCAGAA TGGCGTCACT TTCCAGCAGC  1000
CCAACGCCGA GCTCGGTAGC TACTCTGGCA ACACGCTCAA CGATGCTTAC  1050
TGCGCAGCTG AAGAGGCGGA ATTCGGCGGA TCATCTTTCT CAGACAAGGG  1100
TGGCCTTACC CAATTCAAGC AGGCTACTTC AGGCGGCATG GTCTTGGTTA  1150
TGAGCCTGTG GGATGACGTG AGTTCATGGA TAGCATTGAC ATTGTCGAGA  1200
GAACCATAGC CGCTGACCGA GACACAACAG TACTACGCCA ACATGCTGTG  1250
GCTGGACTCC ATCTACCCGA CGAACGAGAC CTCCTCTACC CCCGGTGCCG  1300
CGCGCGGAAG CTGCTCTACC AGCTCCGGTG TCCCTGCCCA GCTCGAGTCT  1350
CAGTCTACCA ACGCCAAGGT CGTCTTCTCC AACATCAAGT TCGGACCCAT  1400
TGGCAGCACT GGTAACTCCA GCGGCGGAAA CCCCCCGGGC GGAGGAAACC  1450
CCCCCGGCAC CACCACCACC CGACGCCCAG CTACCACCAC CGGAAGCTCT  1500
CCCGGACCTA CTCAGACACA CTATGGCCAG TGCGGTGGAA TTGGGTACTC  1550
GGGCCCCACG GTCTGCGCCA GCGGCAGCAC ATGCCAGG              1588
```

FIG._7

T. konilangbra Signal Sequence

```
MYRKLAVITA FLATARA                                       17
```

FIG._8A

T. konilangbra Mature Amino Acid Sequence

```
QSACTIQAET HPPLTWQKCS SGGSCTSQTG SVVIDANWRW THATNSTTNC    50
YDGNTWSSSL CPDNESCAKN CCLDGAAYAS TYGVTTSADS LSIGFVTQSQ   100
QKNVGARLYL MASDTTYQEF TLLGNEFSFD VDVSQLPCGL NGALYFVSMD   150
ADGGVSKYPS NTAGAKYGTG YCDSQCPRDL KFINGEANVE GWEPASNNAN   200
TGIGGHGSCC SEMDIWEANS ISEALTPHPC TTVGQAICDG DGCGGTYSDD   250
RYGGTCDPDG CDWNPYRLGN TSXYGPGSSF TLDTTKKMTV VTQFATSGAI   300
NRYYVQNGVT FQQPNAELGS YSGNTLNDAY CAAEEAEFGG SSFSDKGGLT   350
QFKQATSGGM VLVMSLWDDY YANMLWLDSI YPTNETSSTP GAARGSCSTS   400
SGVPAQLESQ STNAKVVFSN IKFGPIGSTG NSSGGNPPGG GNPPGTTTTR   450
RPATTTGSSP GPTQTHYGQC GGIGYSGPTV CASGSTCQVL NPYYSQCL    498
```

FIG._8B

T. pseudokoningii Genomic DNA Sequence.

```
TCGGCCTGCA CCCTCCAGAC GGAAACTCAC CCGCCTCTGA CATGGCAGAA    50
ATGCTCATCT GGTGGCACTT GCACCCAACA GACGGGCTCC GTGGTCATCG   100
ACGCGAACTG GCGCTGGACT CACGCTACGA ACAGCAGCAC GAACTGCTAC   150
GACGGTAACA CTTGGAGCTC AACCTTGTGC CCTGACAATG AGACTTGCGC   200
GAAGAACTGC TGCTTGGATG GTGCCGCCTA CGCGTCGACG TACGGAGTCA   250
CCACGAGCGC TGACAGCCTC TCCATTGGCT TCGTCACTCA GTCTGCGCAG   300
AAGAATGTCG GCGCCCGTCT CTACTTGATG GCGAGTGACA CGACCTACCA   350
AGAATTTACC CTGCTTGGCA ACGAGTTCTC CTTCGATGTT GATGTTTCCC   400
AGCTGCCGTA AGTGGCCAAC TACACCCCTT GACGGTATCC TCTCATTGGT   450
TCCCAGCTGA CTCGCGAAAT TAAGATGTGG CTTGAACGGA GCTCTTTACT   500
TCGTGTCCAT GGACGCGGAT GGTGGCGTGA GCAAGTATCC CACAAACACT   550
GCCGGCGCCA AGTACGGCAC GGGTTACTGT GACAGCCAGT GCCCTCGTGA   600
TCTCAAGTTC ATCAACGGCG AGGCCAACGT TGAGGGCTGG GAGCCGTTCT   650
CCAACAACGC CAACACGGGC ATTGGCGGAC ATGGAAGCTG CTGCTCTGAG   700
ATGGATATCT GGGAGGCCAA CTCCATCTCT GAGGCTCTTA CTCCTCATCC   750
TTGCACGACC GTCGGGCAGG AAATTTGCGA TGGTGACTCC TGCGGCGGAA   800
CCTACTCCGG TGATCGATAT GGCGGTACTT GCGATCCTGA TGGCTGCGAT   850
TGGAACCCAT ACCGCTTGGG CAACACCAGC TTCTACGGGC CCGGCTCAAG   900
CTTCGCTCTT GATACCACCA AGAAGTTGAC CGTTGTCACC CAGTTCGAGA   950
CTTCGGGCGC TATCAACCGG TACTACGTCC AGAATGGCGT CACTTTCCAG  1000
CAGCCCAACG CCGAGCTCGG TAGTTACTCT GGCAACTCGC TCGACGATGA  1050
CTACTGCGCG GCTGAAGAGG CGGAGTTTGG TGGCTCTTCT TTCTCGGACA  1100
AGGGCGGCCT TACTCAATTC AAAAAGGCTA CTTCCGGTGG CATGGTCTTG  1150
GTCATGAGCT TGTGGGATGA TGTGAGTTCA TGAATAGCAT TCAAACAGTC  1200
AACAGAATAA CAGCAGCTGA CTGAGACACA ATAGTACTAC GCCAACATGC  1250
TGTGGCTGGA CTCCACCTAC CCGACGAACG AGACCTCTTC CACCCCCGGT  1300
GCCGTGCGCG GAAGCTGCTC CACCAGCTCC GGTGTCCCTG CTCAGCTTGA  1350
GTCCAGTCT TCCAACGCCA AGGTCGTATA CTCCAACATC AAGTTCGGCC  1400
CTATCGGCAG CACCGGCAAC TCCAGCGGCG GTAGCCCTCC CGGCGGAGGA  1450
AACCCTCCCG GTACCACGAC CACCCGCCGC CCAGCTACCT CCACTGGAAG  1500
CTCTCCCGGC CCTACTCAGA CGCACTATGG CCAGTGCGGT GGTATTGGGT  1550
ACTCGGGCCC CACGGTCTGC GCGAGTGGCA GCACTTGCCA GG          1592S
```

FIG._9

T. pseudokoningii Signal Sequence

```
MYRKLAVITA FLATARA                                        17
```

FIG._10A

T. pseudokoningii Mature Amino Acid Sequence

```
QSACTLQTET HPPLTWQKCS SGGTCTQQTG SVVIDANWRW THATNSSTNC    50
YDGNTWSSTL CPDNETCAKN CCLDGAAYAS TYGVTTSADS LSIGFVTQSA   100
QKNVGARLYL MASDTTYQEF TLLGNEFSFD VDVSQLPCGL NGALYFVSMD   150
ADGGVSKYPT NTAGAKYGTG YCDSQCPRDL KFINGEANVE GWEPFSNNAN   200
TGIGGHGSCC SEMDIWEANS ISEALTPHPC TTVGQEICDG DSCGGTYSGD   250
RYGGTCDPDG CDWNPYRLGN TSFYGPGSSF ALDTTKKLTV VTQFETSGAI   300
NRYYVQNGVT FQQPNAELGS YSGNSLDDDY CAAEEAEFGG SSFSDKGGLT   350
QFKKATSGGM VLVMSLWDDY YANMLWLDST YPTNETSSTP GAVRGSCSTS   400
SGVPAQLESQ SSNAKVVYSN IKFGPIGSTG NSSGGSPPGG GNPPGTTTTR   450
RPATSTGSSP GPTQTHYGQC GGIGYSGPTV CASGSTCQVL NPYYSQCL     498
```

FIG._10B

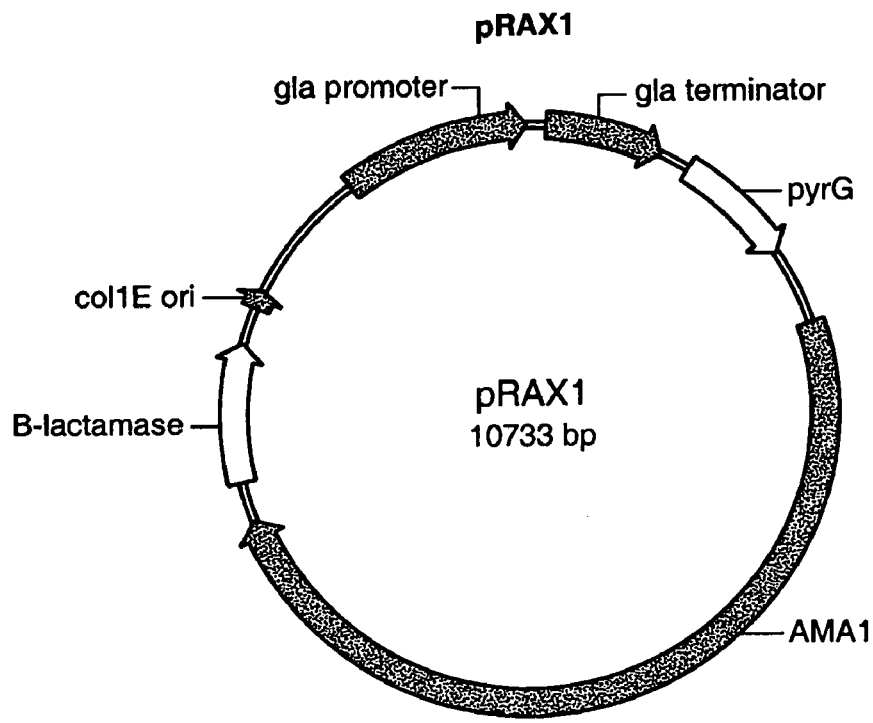
FIG._11
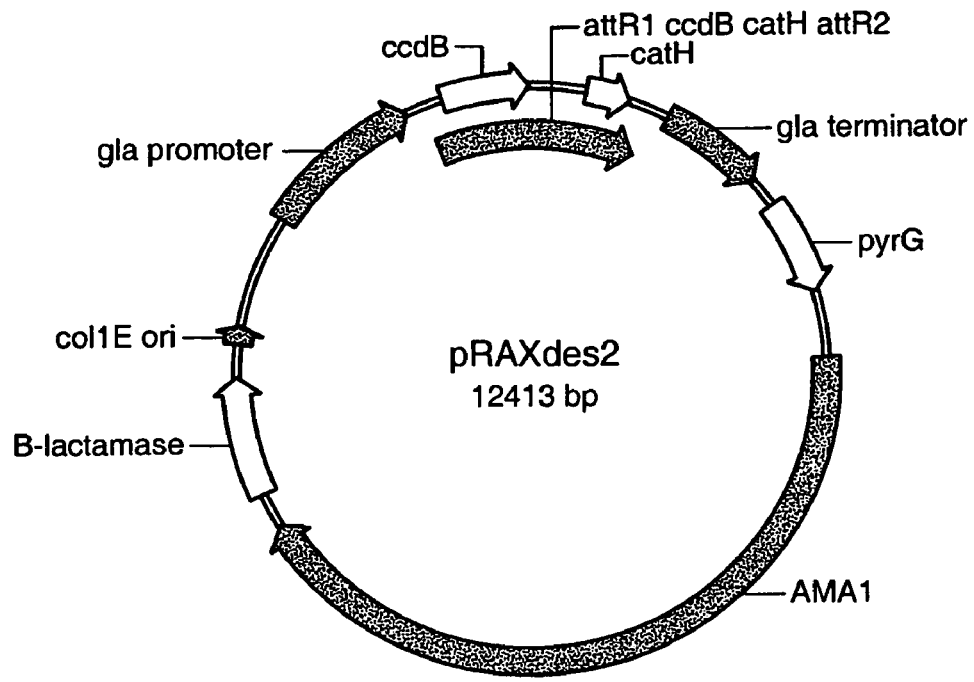
FIG._12

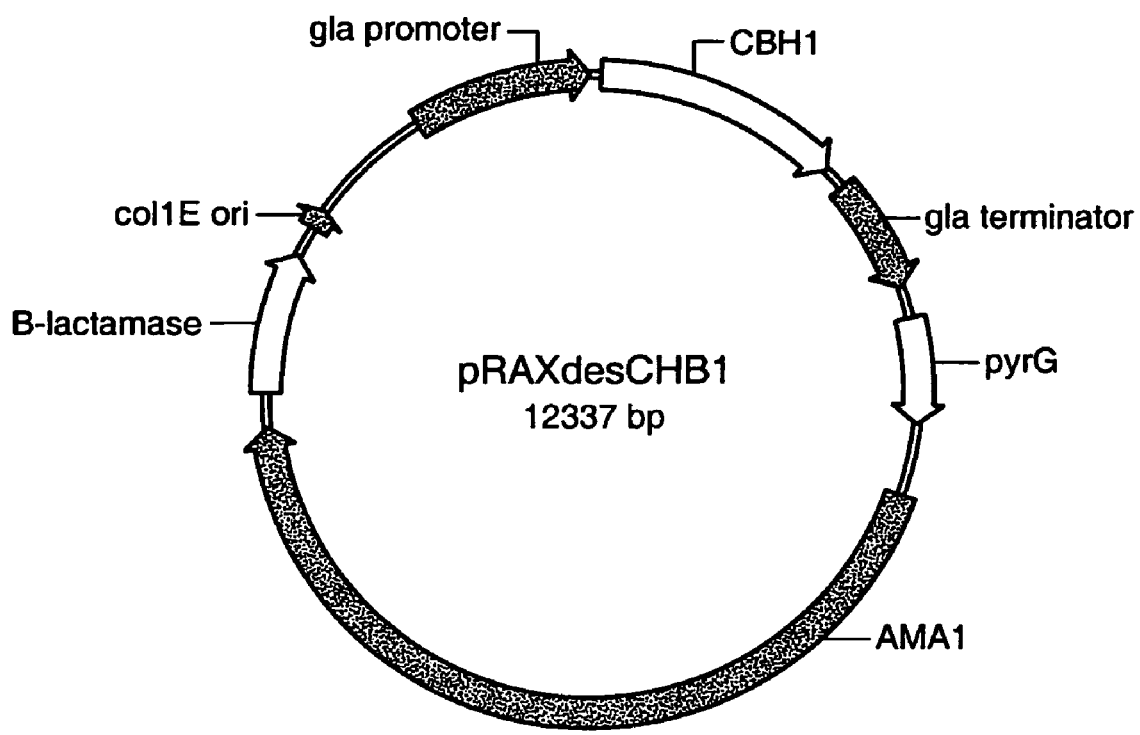
FIG._13

SEQUENCE LISTING

<160> NUMBER OF SEQ ID NOS: 18

<210> SEQ ID NO 1
<211> LENGTH: 1491
<212> TYPE: DNA
<213> ORGANISM: Hyprocrea jecorina

<400> SEQUENCE: 1

```
cagtcggcct gcactctcca atcggagact cacccgcctc tgacatggca gaaatgctcg      60
tctggtggca cttgcactca acagacaggc tccgtggtca tcgacgccaa ctggcgctgg     120
actcacgcta cgaacagcag cacgaactgc tacgatggca acacttggag ctcgacccta     180
tgtcctgaca acgagacctg cgcgaagaac tgctgtctgg acggtgccgc ctacgcgtcc     240
acgtacggag ttaccacgag cggtaacagc ctctccattg gctttgtcac ccagtctgcg     300
cagaagaacg ttggcgctcg cctttacctt atggcgagcg acacgaccta ccaggaattc     360
accctgcttg gcaacgagtt ctctttcgat gttgatgttt cgcagctgcc gtgcggcttg     420
aacggagctc tctacttcgt gtccatggac gcggatggtg gcgtgagcaa gtatcccacc     480
aacaccgctg gcgccaagta cggcacgggg tactgtgaca gccagtgtcc ccgcgatctg     540
aagttcatca atggccaggc caacgttgag ggctgggagc cgtcatccaa caacgcgaac     600
acgggcattg gaggacacgg aagctgctgc tctgagatgg atatctggga ggccaactcc     660
atctccgagg ctcttacccc ccaccccttgc acgactgtcg gccaggagat ctgcgagggt     720
gatgggtgcg gcggaactta ctccgataac agatatggcg gcacttgcga tcccgatggc     780
tgcgactgga acccataccg cctgggcaac accagcttct acggccctgg ctcaagcttt     840
accctcgata ccaccaagaa attgaccgtt gtcacccagt tcgagacgtc gggtgccatc     900
aaccgatact atgtccagaa tggcgtcact ttccagcagc ccaacgccga gcttggtagt     960
tactctggca acgagctcaa cgatgattac tgcacagctg aggaggcaga attcggcgga    1020
```

-continued

```
tcctctttct cagacaaggg cggcctgact cagttcaaga aggctacctc tgcggcatg      1080 gttctggtca tgagtctgtg ggatgattac tacgccaaca tgctgtggct ggactccacc    1140
tacccgacaa acgagacctc ctccacaccc ggtgccgtgc gcggaagctg ctccaccagc    1200
tccggtgtcc ctgctcaggt cgaatctcag tctcccaacg ccaaggtcac cttctccaac    1260
atcaagttcg gacccattgg cagcaccggc aaccctagcg gcggcaaccc tcccggcgga    1320
aacccgcctg caccaccac acccgccgc ccagccacta ccactggaag ctctcccgga     1380
cctacccagt ctcactacgg ccagtgcggc ggtattggct acagcggccc cacggtctgc    1440
gccagcggca caacttgcca ggtcctgaac ccttactact ctcagtgcct g             1491
```

<210> SEQ ID NO 2
<211> LENGTH: 497
<212> TYPE: PRT
<213> ORGANISM: Hyprocrea jecorina

<400> SEQUENCE: 2

```
Gln Ser Ala Cys Thr Leu Gln Ser Glu Thr His Pro Pro Leu Thr Trp
  1               5                  10                  15

Gln Lys Cys Ser Ser Gly Gly Thr Cys Thr Gln Thr Gly Ser Val
             20                  25                  30

Val Ile Asp Ala Asn Trp Arg Trp Thr His Ala Thr Asn Ser Ser Thr
         35                  40                  45

Asn Cys Tyr Asp Gly Asn Thr Trp Ser Ser Thr Leu Cys Pro Asp Asn
     50                  55                  60

Glu Thr Cys Ala Lys Asn Cys Cys Leu Asp Gly Ala Ala Tyr Ala Ser
 65                  70                  75                  80

Thr Tyr Gly Val Thr Thr Ser Gly Asn Ser Leu Ser Ile Gly Phe Val
                 85                  90                  95

Thr Gln Ser Ala Gln Lys Asn Val Gly Ala Arg Leu Tyr Leu Met Ala
            100                 105                 110

Ser Asp Thr Thr Tyr Gln Glu Phe Thr Leu Leu Gly Asn Glu Phe Ser
        115                 120                 125

Phe Asp Val Asp Val Ser Gln Leu Pro Cys Gly Leu Asn Gly Ala Leu
    130                 135                 140

Tyr Phe Val Ser Met Asp Ala Asp Gly Gly Val Ser Lys Tyr Pro Thr
145                 150                 155                 160

Asn Thr Ala Gly Ala Lys Tyr Gly Thr Gly Tyr Cys Asp Ser Gln Cys
                165                 170                 175

Pro Arg Asp Leu Lys Phe Ile Asn Gly Gln Ala Asn Val Glu Gly Trp
            180                 185                 190

Glu Pro Ser Ser Asn Asn Ala Asn Thr Gly Ile Gly Gly His Gly Ser
        195                 200                 205

Cys Cys Ser Glu Met Asp Ile Trp Glu Ala Asn Ser Ile Ser Glu Ala
    210                 215                 220

Leu Thr Pro His Pro Cys Thr Thr Val Gly Gln Glu Ile Cys Glu Gly
225                 230                 235                 240

Asp Gly Cys Gly Gly Thr Tyr Ser Asp Asn Arg Tyr Gly Gly Thr Cys
                245                 250                 255

Asp Pro Asp Gly Cys Asp Trp Asn Pro Tyr Arg Leu Gly Asn Thr Ser
            260                 265                 270

Phe Tyr Gly Pro Gly Ser Ser Phe Thr Leu Asp Thr Thr Lys Lys Leu
        275                 280                 285

Thr Val Val Thr Gln Phe Glu Ser Gly Ala Ile Asn Arg Tyr Tyr
    290                 295                 300
```

```
Val Gln Asn Gly Val Thr Phe Gln Gln Pro Asn Ala Glu Leu Gly Ser
305                 310                 315                 320

Tyr Ser Gly Asn Glu Leu Asn Asp Asp Tyr Cys Thr Ala Glu Glu Ala
            325                 330                 335

Glu Phe Gly Gly Ser Ser Phe Ser Asp Lys Gly Leu Thr Gln Phe
        340                 345                 350

Lys Lys Ala Thr Ser Gly Gly Met Val Leu Val Met Ser Leu Trp Asp
        355                 360                 365

Asp Tyr Tyr Ala Asn Met Leu Trp Leu Asp Ser Thr Tyr Pro Thr Asn
        370                 375                 380

Glu Thr Ser Ser Thr Pro Gly Ala Val Arg Gly Ser Cys Ser Thr Ser
385                 390                 395                 400

Ser Gly Val Pro Ala Gln Val Glu Ser Gln Ser Pro Asn Ala Lys Val
                405                 410                 415

Thr Phe Ser Asn Ile Lys Phe Gly Pro Ile Gly Ser Thr Gly Asn Pro
                420                 425                 430

Ser Gly Gly Asn Pro Pro Gly Gly Asn Pro Pro Gly Thr Thr Thr
            435                 440                 445

Arg Arg Pro Ala Thr Thr Thr Gly Ser Ser Pro Gly Pro Thr Gln Ser
    450                 455                 460

His Tyr Gly Gln Cys Gly Gly Ile Gly Tyr Ser Gly Pro Thr Val Cys
465                 470                 475                 480

Ala Ser Gly Thr Thr Cys Gln Val Leu Asn Pro Tyr Tyr Ser Gln Cys
                485                 490                 495

Leu
```

<210> SEQ ID NO 3
<211> LENGTH: 1635
<212> TYPE: DNA
<213> ORGANISM: Hyprocrea orientalis

<400> SEQUENCE: 3

```
cgtcatctcg gccttcttgg ccacggcccg tgctcagtcg gcctgcactc tccaaacgga      60
gactcacccg tctctgacat ggcagaaatg ctcgtctggc ggcacttgca cccagcagac     120
aggctccgtg gtcatcgacg ccaactggcg ctggactcac gcgactaaca gcagcacgaa     180
ctgctacgac ggcaacactt ggagctcaac cctatgccct gacaacgaga cttgcgcgaa     240
gaattgctgc ctggacggtg ccgcctatgc gtccacgtac ggagtcacca cgagtgccga     300
cagcctctcc atcggcttcg tcacgcaatc tgcacagaag aacgttggcg cccgtctcta     360
cctgatggcg agtgacacga cttaccagga gttcacgctg cttggcaacg agttctcttt     420
tgacgttgat gtttcgcagc tgccgtaagt gacaaccatt ccccgcgagg ccatcttctc     480
attggttccg agctgacccg ccgatctaag atgtggcttg aacggcgctc tgtacttcgt     540
gtctatggat gcggatggtg gcgtgagcaa gtatcccacc aacaccgccg cgccaagta     600
cggcacgggc tactgcgaca gccagtgccc ccgcgatctc aagttcatca acggccaggc     660
caacgttgaa ggctgggagc cgtcctccaa caacgccaac acgggtattg gcggacacgg     720
aagctgctgc tctgagatgg atatctggga ggccaactcc atctccgagg ctctgactcc     780
tcacccttgc acgactgttg ccaggagat ctgcacggt gacggctgcg gcggaaccta     840
ctccaacgac cgatatggtg gtacttgcga tcctgatggt tgtgattgga atccataccg     900
cttgggcaac accagcttct atggccctgg ctcgagcttc acctcgata ccaccaagaa     960
gttgaccgtt gtcacccagt tcgagacctc gggtgccatc aaccgttact atgtccagaa    1020
```

-continued

```
cggcgtcact taccagcaac ccaacgccga gctcggtagt tactctggta atgagctcaa      1080
cgatgactac tgcacagctg aggagtcgga attcggcggc tcctccttct cggacaaggg      1140
cggccttact cagttcaaga aggccacttc cggcggcatg gtcctggtca tgagcttgtg      1200
ggatgacgtg agttgataga cagcattcac attgtcgttg aaagacgggc ggctaaccg       1260 agacatatga tatctaacag tactacgcca acatgctgtg gctggactcc acctacccga      1320
caaacgagac ctcctccacc cccggcgccg tgcgcggaag ctgctccacc agctccggcg      1380
tccccgctca gctcgagtcc cagtccccca acgccaaggt cgtctactcc aacatcaagt      1440
tcgggcccat tggcagcacc ggcaacccca gcggcggaaa ccctcctggc ggaaaccctc      1500
ccggcaccac caccacccgc cgcccagcta ccaccactgg aagctctccc ggacctactc      1560
agactcacta cggccagtgc ggcggcatcg gctacagcgg ccctacggtc tgcgccagcg      1620
gcacgacctg ccagg                                                      1635

<210> SEQ ID NO 4
<211> LENGTH: 17
<212> TYPE: PRT
<213> ORGANISM: Hyprocrea orientalis

<400> SEQUENCE: 4

Met Tyr Arg Lys Leu Ala Val Ile Ser Ala Phe Leu Ala Thr Ala Arg
 1               5                   10                  15

Ala

<210> SEQ ID NO 5
<211> LENGTH: 497
<212> TYPE: PRT
<213> ORGANISM: Hyprocrea orientalis

<400> SEQUENCE: 5

Gln Ser Ala Cys Thr Leu Gln Thr Glu Thr His Pro Ser Leu Thr Trp
 1               5                   10                  15

Gln Lys Cys Ser Ser Gly Gly Thr Cys Thr Gln Thr Gly Ser Val
                20                  25                  30

Val Ile Asp Ala Asn Trp Arg Trp Thr His Ala Thr Asn Ser Ser Thr
             35                  40                  45

Asn Cys Tyr Asp Gly Asn Thr Trp Ser Ser Thr Leu Cys Pro Asp Asn
 50                  55                  60

Glu Thr Cys Ala Lys Asn Cys Cys Leu Asp Gly Ala Ala Tyr Ala Ser
 65                  70                  75                  80

Thr Tyr Gly Val Thr Thr Ser Ala Asp Ser Leu Ser Ile Gly Phe Val
                 85                  90                  95

Thr Gln Ser Ala Gln Lys Asn Val Gly Ala Arg Leu Tyr Leu Met Ala
            100                 105                 110

Ser Asp Thr Thr Tyr Gln Glu Phe Thr Leu Leu Gly Asn Glu Phe Ser
            115                 120                 125

Phe Asp Val Asp Val Ser Gln Leu Pro Cys Gly Leu Asn Gly Ala Leu
        130                 135                 140

Tyr Phe Val Ser Met Asp Ala Asp Gly Gly Val Ser Lys Tyr Pro Thr
145                 150                 155                 160

Asn Thr Ala Gly Ala Lys Tyr Gly Thr Gly Tyr Cys Asp Ser Gln Cys
                165                 170                 175

Pro Arg Asp Leu Lys Phe Ile Asn Gly Gln Ala Asn Val Glu Gly Trp
            180                 185                 190
```

```
Glu Pro Ser Ser Asn Asn Ala Asn Thr Gly Ile Gly Gly His Gly Ser
        195                 200                 205
Cys Cys Ser Glu Met Asp Ile Trp Glu Ala Asn Ser Ile Ser Glu Ala
    210                 215                 220
Leu Thr Pro His Pro Cys Thr Thr Val Gly Gln Glu Ile Cys Asp Gly
225                 230                 235                 240
Asp Gly Cys Gly Gly Thr Tyr Ser Asn Asp Arg Tyr Gly Gly Thr Cys
                245                 250                 255
Asp Pro Asp Gly Cys Asp Trp Asn Pro Tyr Arg Leu Gly Asn Thr Ser
            260                 265                 270
Phe Tyr Gly Pro Gly Ser Ser Phe Thr Leu Asp Thr Thr Lys Lys Leu
        275                 280                 285
Thr Val Val Thr Gln Phe Glu Thr Ser Gly Ala Ile Asn Arg Tyr Tyr
290                 295                 300
Val Gln Asn Gly Val Thr Tyr Gln Gln Pro Asn Ala Glu Leu Gly Ser
305                 310                 315                 320
Tyr Ser Gly Asn Glu Leu Asn Asp Asp Tyr Cys Thr Ala Glu Glu Ser
                325                 330                 335
Glu Phe Gly Gly Ser Ser Phe Ser Asp Lys Gly Gly Leu Thr Gln Phe
            340                 345                 350
Lys Lys Ala Thr Ser Gly Gly Met Val Leu Val Met Ser Leu Trp Asp
        355                 360                 365
Asp Tyr Tyr Ala Asn Met Leu Trp Leu Asp Ser Thr Tyr Pro Thr Asn
    370                 375                 380
Glu Thr Ser Ser Thr Pro Gly Ala Val Arg Gly Ser Cys Ser Thr Ser
385                 390                 395                 400
Ser Gly Val Pro Ala Gln Leu Glu Ser Gln Ser Pro Asn Ala Lys Val
                405                 410                 415
Val Tyr Ser Asn Ile Lys Phe Gly Pro Ile Gly Ser Thr Gly Asn Pro
            420                 425                 430
Ser Gly Gly Asn Pro Pro Gly Gly Asn Pro Pro Gly Thr Thr Thr Thr
        435                 440                 445
Arg Arg Pro Ala Thr Thr Thr Gly Ser Ser Pro Gly Pro Thr Gln Thr
450                 455                 460
His Tyr Gly Gln Cys Gly Gly Ile Gly Tyr Ser Gly Pro Thr Val Cys
465                 470                 475                 480
Ala Ser Gly Thr Thr Cys Gln Val Leu Asn Pro Tyr Tyr Ser Gln Cys
                485                 490                 495
Leu

<210> SEQ ID NO 6
<211> LENGTH: 1589
<212> TYPE: DNA
<213> ORGANISM: Hyprocrea schweintzii

<400> SEQUENCE: 6
tcggcctgca ctctccaaac ggagactcac ccgtctctga catggcagaa atgctcgtct      60
ggcggcactt gcacccagca gacaggctcc gtggtcatcg acgccaactg cgctggact      120 cacgctacta acagcagcac gaactgctac gacggcaaca cttggagctc aaccctgtgc      180
cctgacaatg agacttgcgc gaagaactgc tgcctggacg tgccgcccta tcgtccacg      240 tacggagtca ccacgagtgc cgacagcctc tccatcggct tcgtgacaca gtctgcacag      300
aaaaacgttg cgcccgtctc tacctgatg gcgagtgaca cgacttacca ggagttcacg      360
ctgcttggca acgagttctc attcgacgtt gatgtttcgc agctgccgta agtgacaacc      420
```

```
attcccccga cgccatcttc tcattggttc gaagctgacc cgccgatcta agatgtggct    480
tgaacggcgc tctttacttc gtgtccatgg acgcagatgg tggcgtgagc aagtatccca    540
ccaacaccgc cggcgccaag tacggcacgg gctactgtga cagccagtgc ccccgcgatc    600
tcaagtttat caacggccag gccaacgttg aaggctggga gccgtcctcc aacaacgcca    660
acacgggtat tggcggacac ggaagctgct gctccgagat ggatatctgg gaggccaact    720
ccatctccga ggctcttact cctcacccct tgcacgaatg tggccaggag atctgcgacg    780
gtgacggctg cggcggaacc tactccaacg accgatatgg tggtacttgc gatcctgatg    840
gttgtgattg gaatccatac cgcttgggca acaccagctt ctatggccct ggctcgagct    900
tcaccctcga taccaccaag aagttgaccg tcgtcaccca gttcgagact cgggtgcca     960 tcaaccgtta ctatgtccag aatggcgtca cttaccagca acccaacgcc gagctcggca    1020
gttactctgg taatgagctc aacgatgcct actgcacagc tgaagagtcg gaatttggcg    1080
gttcctcctt ctcggacaag gcggccttat ctcagttcaa gaaggccact tccggcggca    1140
tggtcctggt catgagcttg tgggatgacg tgagtccata aacagcatt cacattgtcg     1200 tcggaaagac ggccggctaa ccgagacatt acagtactac gccaacatgc tgtggctgga    1260
ctccacctac ccgacaaacg agacctcctc cacccccggt gccgtgcgcg aagctgctc    1320 caccagctcc ggcgtccag ctcagctcga gtcccagtcc gccaacgcca aggtcgtcta     1380
ctccaacatc aagttcggac ccattggcag caccggcaac cccagcggcg aaaaccctcc    1440
tggcggaaac cctcccggca ccaccaccac ccgccgccca gctaccacca ctggaagctc    1500
tcccggacct actcagactc actatggcca gtgcggcggc atcggctaca gcggccctac    1560
gatctgcgcc agcggcacga cctgccagg                                      1589
```

<210> SEQ ID NO 7
<211> LENGTH: 17
<212> TYPE: PRT
<213> ORGANISM: Hyprocrea schweintzii

<400> SEQUENCE: 7

```
Met Tyr Arg Lys Leu Ala Val Ile Thr Ala Phe Leu Ala Thr Ala Arg
 1               5                  10                  15

Ala
```

<210> SEQ ID NO 8
<211> LENGTH: 497
<212> TYPE: PRT
<213> ORGANISM: Hyprocrea schweintzii

<400> SEQUENCE: 8

```
Gln Ser Ala Cys Thr Leu Gln Thr Glu Thr His Pro Ser Leu Thr Trp
 1               5                  10                  15

Gln Lys Cys Ser Ser Gly Gly Thr Cys Thr Gln Thr Gly Ser Val
                20                  25                  30

Val Ile Asp Ala Asn Trp Arg Trp Thr His Ala Thr Asn Ser Ser Thr
         35                  40                  45

Asn Cys Tyr Asp Gly Asn Thr Trp Ser Ser Thr Leu Cys Pro Asp Asn
     50                  55                  60

Glu Thr Cys Ala Lys Asn Cys Cys Leu Asp Gly Ala Ala Tyr Ala Ser
 65                  70                  75                  80

Thr Tyr Gly Val Thr Thr Ser Ala Asp Ser Leu Ser Ile Gly Phe Val
                 85                  90                  95
```

```
Thr Gln Ser Ala Gln Lys Asn Val Gly Ala Arg Leu Tyr Leu Met Ala
            100                 105                 110
Ser Asp Thr Thr Tyr Gln Glu Phe Thr Leu Leu Gly Asn Glu Phe Ser
        115                 120                 125
Phe Asp Val Asp Val Ser Gln Leu Pro Cys Gly Leu Asn Gly Ala Leu
130                 135                 140
Tyr Phe Val Ser Met Asp Ala Asp Gly Gly Val Ser Lys Tyr Pro Thr
145                 150                 155                 160
Asn Thr Ala Gly Ala Lys Tyr Gly Thr Gly Tyr Cys Asp Ser Gln Cys
                165                 170                 175
Pro Arg Asp Leu Lys Phe Ile Asn Gly Gln Ala Asn Val Glu Gly Trp
            180                 185                 190
Glu Pro Ser Ser Asn Asn Ala Asn Thr Gly Ile Gly Gly His Gly Ser
        195                 200                 205
Cys Cys Ser Glu Met Asp Ile Trp Glu Ala Asn Ser Ile Ser Glu Ala
210                 215                 220
Leu Thr Pro His Pro Cys Thr Asn Val Gly Gln Glu Ile Cys Asp Gly
225                 230                 235                 240
Asp Gly Cys Gly Gly Thr Tyr Ser Asn Asp Arg Tyr Gly Gly Thr Cys
                245                 250                 255
Asp Pro Asp Gly Cys Asp Trp Asn Pro Tyr Arg Leu Gly Asn Thr Ser
            260                 265                 270
Phe Tyr Gly Pro Gly Ser Ser Phe Thr Leu Asp Thr Lys Lys Leu
        275                 280                 285
Thr Val Val Thr Gln Phe Glu Thr Ser Gly Ala Ile Asn Arg Tyr Tyr
290                 295                 300
Val Gln Asn Gly Val Thr Tyr Gln Gln Pro Asn Ala Glu Leu Gly Ser
305                 310                 315                 320
Tyr Ser Gly Asn Glu Leu Asn Asp Ala Tyr Cys Thr Ala Glu Glu Ser
                325                 330                 335
Glu Phe Gly Gly Ser Ser Phe Ser Asp Lys Gly Gly Leu Thr Gln Phe
            340                 345                 350
Lys Lys Ala Thr Ser Gly Gly Met Val Leu Val Met Ser Leu Trp Asp
        355                 360                 365
Asp Tyr Tyr Ala Asn Met Leu Trp Leu Asp Ser Thr Tyr Pro Thr Asn
370                 375                 380
Glu Thr Ser Ser Thr Pro Gly Ala Val Arg Gly Ser Cys Ser Thr Ser
385                 390                 395                 400
Ser Gly Val Pro Ala Gln Leu Glu Ser Gln Ser Ala Asn Ala Lys Val
                405                 410                 415
Val Tyr Ser Asn Ile Lys Phe Gly Pro Ile Gly Ser Thr Gly Asn Pro
            420                 425                 430
Ser Gly Gly Asn Pro Pro Gly Gly Asn Pro Pro Gly Thr Thr Thr Thr
        435                 440                 445
Arg Arg Pro Ala Thr Thr Thr Gly Ser Ser Pro Gly Pro Thr Gln Thr
450                 455                 460
His Tyr Gly Gln Cys Gly Gly Ile Gly Tyr Ser Gly Pro Thr Ile Cys
465                 470                 475                 480
Ala Ser Gly Thr Thr Cys Gln Val Leu Asn Pro Tyr Tyr Ser Gln Cys
                485                 490                 495
Leu

<210> SEQ ID NO 9
<211> LENGTH: 1588
```

```
<212> TYPE: DNA
<213> ORGANISM: Trichoderma konilangbra

<400> SEQUENCE: 9
tcggcctgca ccattcaagc ggagactcac ccgcctctga catggcagaa atgctcatcc      60
ggtggtagtt gcacctcgca aaccggttct gtggtgattg acgcgaactg gcgatggact     120
cacgcgacta acagcaccac gaactgctac gacggtaaca cttggagctc cagtctttgc     180
cccgacaatg agagttgcgc aaagaactgc tgcctggacg gtgcagccta cgcatccacg     240
tacggagtca ccacgagtgc tgatagcctc tccattggct tcgtcactca gtctcagcag     300
aagaatgttg gcgctcgtct ctacctgatg gcaagcgaca cgacctacca ggaatttacc     360
ctgcttggca acgagttctc tttcgatgtt gatgtttcac agctgccgta agtgactagc     420
atttacctcc gacgccatct cattgattcc cagctgacgg ccaattcaag atgtggcttg     480
aacggagccc tttacttcgt gtccatggac gcggatggtg gcgtgagcaa gtatccctcc     540
aacactgccg gcgccaagta cggcacgggc tactgcgata gccagtgtcc ccgtgatttg     600
aagttcatca acggcgaggc caacgttgag ggctgggagc cggcttcgaa caacgccaac     660
acgggtattg gcggacacgg aagctgctgc tctgagatgg atatctggga ggccaactcc     720
atctctgagg cccttactcc tcaccttgc acgactgtcg gccaggccat ttgcgatggt     780
gacggctgcg gtggaaccta ctccgatgac cgatatggtg gtacttgcga tcctgatggc     840
tgtgactgga acccataccg cttgggcaac accagcttct acggccccgg ctcgagcttc     900
accctcgaca ccaccaagaa gatgaccgtc gtcacccagt cgctacttc gggtgccatc     960
aaccgatact atgtccagaa tggcgtcact ttccagcagc caacgccga gctcggtagc    1020
tactctggca acacgctcaa cgatgcttac tgcgcagctg aagaggcgga attcggcgga    1080
tcatctttct cagacaaggg tggccttacc caattcaagc aggctacttc aggcggcatg    1140
gtcttggtta tgagcctgtg ggatgacgtg agttcatgga tagcattgac attgtcgaga    1200
gaaccatagc cgctgaccga gacacaacag tactacgcca acatgctgtg gctggactcc    1260
atctacccga cgaacgagac ctcctctacc cccggtgccg cgcgcggaag ctgctctacc    1320
agctccggtg tccctgccca gctcgagtct cagtctacca acgccaaggt cgtcttctcc    1380
aacatcaagt tcggacccat tggcagcact ggtaactcca gcggcggaaa accccccggc    1440
ggaggaaacc cccccggcac caccaccacc cgacgcccag ctaccaccac cggaagctct    1500
cccggaccta ctcagacaca ctatggccag tgcggtggaa ttgggtactc gggccccacg    1560
gtctgcgcca gcggcagcac atgccagg                                       1588

<210> SEQ ID NO 10
<211> LENGTH: 17
<212> TYPE: PRT
<213> ORGANISM: Trichoderma konilangbra

<400> SEQUENCE: 10

Met Tyr Arg Lys Leu Ala Val Ile Thr Ala Phe Leu Ala Thr Ala Arg
 1               5                  10                  15

Ala

<210> SEQ ID NO 11
<211> LENGTH: 498
<212> TYPE: PRT
<213> ORGANISM: Trichoderma konilangbra
<220> FEATURE:
<221> NAME/KEY: VARIANT
<222> LOCATION: 273
```

<223> OTHER INFORMATION: Xaa = Any Amino Acid

<400> SEQUENCE: 11

```
Gln Ser Ala Cys Thr Ile Gln Ala Glu Thr His Pro Pro Leu Thr Trp
 1               5                  10                  15
Gln Lys Cys Ser Ser Gly Gly Ser Cys Thr Ser Gln Thr Gly Ser Val
             20                  25                  30
Val Ile Asp Ala Asn Trp Arg Trp Thr His Ala Thr Asn Ser Thr Thr
         35                  40                  45
Asn Cys Tyr Asp Gly Asn Thr Trp Ser Ser Leu Cys Pro Asp Asn
 50                  55                  60
Glu Ser Cys Ala Lys Asn Cys Cys Leu Asp Gly Ala Ala Tyr Ala Ser
 65                  70                  75                  80
Thr Tyr Gly Val Thr Thr Ser Ala Asp Ser Leu Ser Ile Gly Phe Val
                 85                  90                  95
Thr Gln Ser Gln Gln Lys Asn Val Gly Ala Arg Leu Tyr Leu Met Ala
            100                 105                 110
Ser Asp Thr Thr Tyr Gln Glu Phe Thr Leu Leu Gly Asn Glu Phe Ser
            115                 120                 125
Phe Asp Val Asp Val Ser Gln Leu Pro Cys Gly Leu Asn Gly Ala Leu
130                 135                 140
Tyr Phe Val Ser Met Asp Ala Asp Gly Gly Val Ser Lys Tyr Pro Ser
145                 150                 155                 160
Asn Thr Ala Gly Ala Lys Tyr Gly Thr Gly Tyr Cys Asp Ser Gln Cys
                165                 170                 175
Pro Arg Asp Leu Lys Phe Ile Asn Gly Glu Ala Asn Val Glu Gly Trp
                180                 185                 190
Glu Pro Ala Ser Asn Asn Ala Asn Thr Gly Ile Gly Gly His Gly Ser
                195                 200                 205
Cys Cys Ser Glu Met Asp Ile Trp Glu Ala Asn Ser Ile Ser Glu Ala
210                 215                 220
Leu Thr Pro His Pro Cys Thr Thr Val Gly Gln Ala Ile Cys Asp Gly
225                 230                 235                 240
Asp Gly Cys Gly Gly Thr Tyr Ser Asp Asp Arg Tyr Gly Gly Thr Cys
                245                 250                 255
Asp Pro Asp Gly Cys Asp Trp Asn Pro Tyr Arg Leu Gly Asn Thr Ser
                260                 265                 270
Xaa Tyr Gly Pro Gly Ser Ser Phe Thr Leu Asp Thr Thr Lys Lys Met
                275                 280                 285
Thr Val Val Thr Gln Phe Ala Thr Ser Gly Ala Ile Asn Arg Tyr Tyr
290                 295                 300
Val Gln Asn Gly Val Thr Phe Gln Gln Pro Asn Ala Glu Leu Gly Ser
305                 310                 315                 320
Tyr Ser Gly Asn Thr Leu Asn Asp Ala Tyr Cys Ala Ala Glu Glu Ala
                325                 330                 335
Glu Phe Gly Gly Ser Ser Phe Ser Asp Lys Gly Gly Leu Thr Gln Phe
                340                 345                 350
Lys Gln Ala Thr Ser Gly Gly Met Val Leu Val Met Ser Leu Trp Asp
                355                 360                 365
Asp Tyr Tyr Ala Asn Met Leu Trp Leu Asp Ser Ile Tyr Pro Thr Asn
370                 375                 380
Glu Thr Ser Ser Thr Pro Gly Ala Ala Arg Gly Ser Cys Ser Thr Ser
385                 390                 395                 400
Ser Gly Val Pro Ala Gln Leu Glu Ser Gln Ser Thr Asn Ala Lys Val
```

|   |   |   | 405 |   |   |   | 410 |   |   |   | 415 |   |
|---|---|---|---|---|---|---|---|---|---|---|---|---|
| Val | Phe | Ser | Asn | Ile | Lys | Phe | Gly | Pro | Ile | Gly | Ser | Thr | Gly | Asn | Ser |
|   |   |   | 420 |   |   |   | 425 |   |   |   | 430 |   |

Ser Gly Gly Asn Pro Pro Gly Gly Gly Asn Pro Pro Gly Thr Thr Thr
                435                  440                  445

Thr Arg Arg Pro Ala Thr Thr Thr Gly Ser Ser Pro Gly Pro Thr Gln
    450                  455                  460

Thr His Tyr Gly Gln Cys Gly Gly Ile Gly Tyr Ser Gly Pro Thr Val
465                  470                  475                  480

Cys Ala Ser Gly Ser Thr Cys Gln Val Leu Asn Pro Tyr Tyr Ser Gln
                485                  490                  495

Cys Leu

<210> SEQ ID NO 12
<211> LENGTH: 1592
<212> TYPE: DNA
<213> ORGANISM: Trichoderma pseudokoningii

<400> SEQUENCE: 12

| | |
|---|---|
| tcggcctgca ccctccagac ggaaactcac ccgcctctga catggcagaa atgctcatct | 60 |
| ggtggcactt gcacccaaca gacgggctcc gtggtcatcg acgcgaactg gcgctggact | 120 |
| cacgctacga acagcagcac gaactgctac gacggtaaca cttggagctc aaccttgtgc | 180 |
| cctgacaatg agacttgcgc gaagaactgc tgcttggatg gtgccgccta cgcgtcgacg | 240 |
| tacggagtca ccacgagcgc tgacagcctc tccattggct tcgtcactca gtctgcgcag | 300 |
| aagaatgtcg gcgcccgtct ctacttgatg gcgagtgaca cgacctacca agaatttacc | 360 |
| ctgcttggca acgagttctc cttcgatgtt gatgtttccc agctgccgta agtggccaac | 420 |
| tacacccctt gacggtatcc tctcattggt tcccagctga ctcgcgaaat taagatgtgg | 480 |
| cttgaacgga gctctttact tcgtgtccat ggacgcggat ggtggcgtga gcaagtatcc | 540 |
| cacaaacact gccggcgcca gtacggcac gggttactgt gacagccagt gccctcgtga | 600 |
| tctcaagttc atcaacggcg aggccaacgt tgagggctgg gagccgttct ccaacaacgc | 660 |
| caacacgggc attggcggac atggaagctg ctgctctgag atggatatct gggaggccaa | 720 |
| ctccatctct gaggctctta ctcctcatcc ttgcacgacc gtcgggcagg aaatttgcga | 780 |
| tggtgactcc tgcggcggaa cctactccgg tgatcgatat ggcggtactt gcgatcctga | 840 |
| tggctgcgat tggaacccat accgcttggg caacaccagc ttctacgggc ccggctcaag | 900 |
| cttcgctctt gataccacca gaagttgac cgttgtcacc cagttcgaga cttcgggcgc | 960 |
| tatcaaccgg tactacgtcc agaatggcgt cactttccag cagcccaacg ccgagctcgg | 1020 |
| tagttactct ggcaactcgc tcgacgatga ctactgcgcg gctgaagagg cggagtttgg | 1080 |
| tggctcttct ttctcggaca agggcggcct tactcaattc aaaaaggcta cttccggtgg | 1140 |
| catggtcttg gtcatgagct tgtgggatga tgtgagttca tgaatagcat tcaaacagtc | 1200 |
| aacagaataa cagcagctga ctgagacaca atagtactac gccaacatgc tgtggctgga | 1260 |
| ctccacctac ccgacgaacg agacctcttc cacccccggt gccgtgcgcg aagctgctc | 1320 |
| caccagctcc ggtgtccctg ctcagcttga gtcccagtct ccaacgcca aggtcgtata | 1380 |
| ctccaacatc aagttcggcc ctatcggcag caccggcaac tccagcggcg gtagccctcc | 1440 |
| cggcggagga aaccctcccg gtaccacgac caccgccgc ccagctacct ccactggaag | 1500 |
| ctctcccggc cctactcaga cgcactatgg ccagtgcggg ggtattgggt actcgggccc | 1560 |
| cacggtctgc gcgagtggca gcacttgcca gg | 1592 |

<210> SEQ ID NO 13
<211> LENGTH: 17
<212> TYPE: PRT
<213> ORGANISM: Trichoderma pseudokoningii

<400> SEQUENCE: 13

Met Tyr Arg Lys Leu Ala Val Ile Thr Ala Phe Leu Ala Thr Ala Arg
 1               5                  10                  15

Ala

<210> SEQ ID NO 14
<211> LENGTH: 498
<212> TYPE: PRT
<213> ORGANISM: Trichoderma pseudokoningii

<400> SEQUENCE: 14

Gln Ser Ala Cys Thr Leu Gln Thr Glu Thr His Pro Pro Leu Thr Trp
 1               5                  10                  15

Gln Lys Cys Ser Ser Gly Gly Thr Cys Thr Gln Gln Thr Gly Ser Val
            20                  25                  30

Val Ile Asp Ala Asn Trp Arg Trp Thr His Ala Thr Asn Ser Ser Thr
        35                  40                  45

Asn Cys Tyr Asp Gly Asn Thr Trp Ser Ser Thr Leu Cys Pro Asp Asn
50                  55                  60

Glu Thr Cys Ala Lys Asn Cys Cys Leu Asp Gly Ala Ala Tyr Ala Ser
65                  70                  75                  80

Thr Tyr Gly Val Thr Thr Ser Ala Asp Ser Leu Ser Ile Gly Phe Val
                85                  90                  95

Thr Gln Ser Ala Gln Lys Asn Val Gly Ala Arg Leu Tyr Leu Met Ala
            100                 105                 110

Ser Asp Thr Thr Tyr Gln Glu Phe Thr Leu Leu Gly Asn Glu Phe Ser
        115                 120                 125

Phe Asp Val Asp Val Ser Gln Leu Pro Cys Gly Leu Asn Gly Ala Leu
    130                 135                 140

Tyr Phe Val Ser Met Asp Ala Asp Gly Gly Val Ser Lys Tyr Pro Thr
145                 150                 155                 160

Asn Thr Ala Gly Ala Lys Tyr Gly Thr Gly Tyr Cys Asp Ser Gln Cys
                165                 170                 175

Pro Arg Asp Leu Lys Phe Ile Asn Gly Glu Ala Asn Val Glu Gly Trp
            180                 185                 190

Glu Pro Phe Ser Asn Asn Ala Asn Thr Gly Ile Gly Gly His Gly Ser
        195                 200                 205

Cys Cys Ser Glu Met Asp Ile Trp Glu Ala Asn Ser Ile Ser Glu Ala
    210                 215                 220

Leu Thr Pro His Pro Cys Thr Thr Val Gly Gln Glu Ile Cys Asp Gly
225                 230                 235                 240

Asp Ser Cys Gly Gly Thr Tyr Ser Gly Asp Arg Tyr Gly Gly Thr Cys
                245                 250                 255

Asp Pro Asp Gly Cys Asp Trp Asn Pro Tyr Arg Leu Gly Asn Thr Ser
            260                 265                 270

Phe Tyr Gly Pro Gly Ser Ser Phe Ala Leu Asp Thr Thr Lys Lys Leu
        275                 280                 285

Thr Val Val Thr Gln Phe Glu Thr Ser Gly Ala Ile Asn Arg Tyr Tyr
    290                 295                 300

Val Gln Asn Gly Val Thr Phe Gln Gln Pro Asn Ala Glu Leu Gly Ser

```
            305                 310                 315                 320
Tyr Ser Gly Asn Ser Leu Asp Asp Tyr Cys Ala Ala Glu Glu Ala
                325                 330                 335

Glu Phe Gly Gly Ser Ser Phe Ser Asp Lys Gly Gly Leu Thr Gln Phe
                340                 345                 350

Lys Lys Ala Thr Ser Gly Gly Met Val Leu Val Met Ser Leu Trp Asp
                355                 360                 365

Asp Tyr Tyr Ala Asn Met Leu Trp Leu Asp Ser Thr Tyr Pro Thr Asn
        370                 375                 380

Glu Thr Ser Ser Thr Pro Gly Ala Val Arg Gly Ser Cys Ser Thr Ser
385                 390                 395                 400

Ser Gly Val Pro Ala Gln Leu Glu Ser Gln Ser Ser Asn Ala Lys Val
                405                 410                 415

Val Tyr Ser Asn Ile Lys Phe Gly Pro Ile Gly Ser Thr Gly Asn Ser
                420                 425                 430

Ser Gly Gly Ser Pro Pro Gly Gly Asn Pro Pro Gly Thr Thr Thr
                435                 440                 445

Thr Arg Arg Pro Ala Thr Ser Thr Gly Ser Ser Pro Gly Pro Thr Gln
        450                 455                 460

Thr His Tyr Gly Gln Cys Gly Gly Ile Gly Tyr Ser Gly Pro Thr Val
465                 470                 475                 480

Cys Ala Ser Gly Ser Thr Cys Gln Val Leu Asn Pro Tyr Tyr Ser Gln
                485                 490                 495

Cys Leu
```

<210> SEQ ID NO 15
<211> LENGTH: 497
<212> TYPE: PRT
<213> ORGANISM: Trichoderma reesei

<400> SEQUENCE: 15

```
Gln Ser Ala Cys Thr Leu Gln Ser Glu Thr His Pro Pro Leu Thr Trp
1               5                   10                  15

Gln Lys Cys Ser Ser Gly Gly Thr Cys Thr Gln Thr Gly Ser Val
                20                  25                  30

Val Ile Asp Ala Asn Trp Arg Trp Thr His Ala Thr Asn Ser Ser Thr
            35                  40                  45

Asn Cys Tyr Asp Gly Asn Thr Trp Ser Ser Thr Leu Cys Pro Asp Asn
        50                  55                  60

Glu Thr Cys Ala Lys Asn Cys Cys Leu Asp Gly Ala Ala Tyr Ala Ser
65                  70                  75                  80

Thr Tyr Gly Val Thr Thr Ser Gly Asn Ser Leu Ser Ile Gly Phe Val
                85                  90                  95

Thr Gln Ser Ala Gln Lys Asn Val Gly Ala Arg Leu Tyr Leu Met Ala
                100                 105                 110

Ser Asp Thr Thr Tyr Gln Glu Phe Thr Leu Leu Gly Asn Glu Phe Ser
            115                 120                 125

Phe Asp Val Asp Val Ser Gln Leu Pro Cys Gly Leu Asn Gly Ala Leu
        130                 135                 140

Tyr Phe Val Ser Met Asp Ala Asp Gly Gly Val Ser Lys Tyr Pro Thr
145                 150                 155                 160

Asn Thr Ala Gly Ala Lys Tyr Gly Thr Gly Tyr Cys Asp Ser Gln Cys
                165                 170                 175

Pro Arg Asp Leu Lys Phe Ile Asn Gly Gln Ala Asn Val Glu Gly Trp
            180                 185                 190
```

```
Glu Pro Ser Ser Asn Asn Ala Asn Thr Gly Ile Gly Gly His Gly Ser
            195                 200                 205
Cys Cys Ser Glu Met Asp Ile Trp Glu Ala Asn Ser Ile Ser Glu Ala
            210                 215                 220
Leu Thr Pro His Pro Cys Thr Val Gly Gln Glu Ile Cys Glu Gly
225                 230                 235                 240
Asp Gly Cys Gly Gly Thr Tyr Ser Asp Asn Arg Tyr Gly Gly Thr Cys
            245                 250                 255
Asp Pro Asp Gly Cys Asp Trp Asn Pro Tyr Arg Leu Gly Asn Thr Ser
            260                 265                 270
Phe Tyr Gly Pro Gly Ser Ser Phe Thr Leu Asp Thr Lys Lys Leu
            275                 280                 285
Thr Val Val Thr Gln Phe Glu Thr Ser Gly Ala Ile Asn Arg Tyr Tyr
            290                 295                 300
Val Gln Asn Gly Val Thr Phe Gln Gln Pro Asn Ala Glu Leu Gly Ser
305                 310                 315                 320
Tyr Ser Gly Asn Glu Leu Asn Asp Asp Tyr Cys Thr Ala Glu Glu Ala
            325                 330                 335
Glu Phe Gly Gly Ser Ser Phe Ser Asp Lys Gly Gly Leu Thr Gln Phe
            340                 345                 350
Lys Lys Ala Thr Ser Gly Gly Met Val Leu Val Met Ser Leu Trp Asp
            355                 360                 365
Asp Tyr Tyr Ala Asn Met Leu Trp Leu Asp Ser Thr Tyr Pro Thr Asn
            370                 375                 380
Glu Thr Ser Ser Thr Pro Gly Ala Val Arg Gly Ser Cys Ser Thr Ser
385                 390                 395                 400
Ser Gly Val Pro Ala Gln Val Glu Ser Gln Ser Pro Asn Ala Lys Val
            405                 410                 415
Thr Phe Ser Asn Ile Lys Phe Gly Pro Ile Gly Ser Thr Gly Asn Pro
            420                 425                 430
Ser Gly Gly Asn Pro Pro Gly Gly Asn Pro Pro Gly Thr Thr Thr Thr
            435                 440                 445
Arg Arg Pro Ala Thr Thr Thr Gly Ser Ser Pro Gly Pro Thr Gln Ser
            450                 455                 460
His Tyr Gly Gln Cys Gly Gly Ile Gly Tyr Ser Gly Pro Thr Val Cys
465                 470                 475                 480
Ala Ser Gly Thr Thr Cys Gln Val Leu Asn Pro Tyr Tyr Ser Gln Cys
            485                 490                 495
Leu

<210> SEQ ID NO 16
<211> LENGTH: 495
<212> TYPE: PRT
<213> ORGANISM: Artificial Sequence
<220> FEATURE:
<223> OTHER INFORMATION: consensus sequence

<400> SEQUENCE: 16

Gln Ser Ala Cys Thr Leu Gln Thr Glu Thr His Pro Pro Leu Thr Trp
1               5                   10                  15
Gln Lys Cys Ser Ser Gly Gly Thr Cys Thr Gln Thr Gly Ser Val
            20                  25                  30
Val Ile Asp Ala Asn Trp Arg Trp Thr His Ala Thr Asn Ser Ser Thr
            35                  40                  45
Asn Cys Tyr Asp Gly Asn Thr Trp Ser Ser Thr Leu Cys Pro Asp Asn
```

-continued

```
                50                  55                  60
Glu Thr Cys Ala Lys Asn Cys Cys Leu Asp Gly Ala Ala Tyr Ala Ser
65                  70                  75                  80

Thr Tyr Gly Val Thr Thr Ser Ala Asp Ser Leu Ser Ile Gly Phe Val
                85                  90                  95

Thr Gln Ser Ala Gln Lys Asn Val Gly Ala Arg Leu Tyr Leu Met Ala
                    100                 105                 110

Ser Asp Thr Thr Tyr Gln Glu Phe Thr Leu Leu Gly Asn Glu Phe Ser
                115                 120                 125

Phe Asp Val Asp Val Ser Gln Leu Pro Cys Gly Leu Asn Gly Ala Leu
130                 135                 140

Tyr Phe Val Ser Met Asp Ala Asp Gly Gly Val Ser Lys Tyr Pro Thr
145                 150                 155                 160

Asn Thr Ala Gly Ala Lys Tyr Gly Thr Gly Tyr Cys Asp Ser Gln Cys
                    165                 170                 175

Pro Arg Asp Leu Lys Phe Ile Asn Gly Gln Ala Asn Val Glu Gly Trp
                180                 185                 190

Glu Pro Ser Ser Asn Asn Ala Asn Thr Gly Ile Gly Gly His Gly Ser
                195                 200                 205

Cys Cys Ser Glu Met Asp Ile Trp Glu Ala Asn Ser Ile Ser Glu Ala
210                 215                 220

Leu Thr Pro His Pro Cys Thr Thr Val Gly Gln Glu Ile Cys Asp Gly
225                 230                 235                 240

Asp Gly Cys Gly Gly Thr Tyr Ser Asp Arg Tyr Gly Gly Thr Cys Asp
                    245                 250                 255

Pro Asp Gly Cys Asp Trp Asn Pro Tyr Arg Leu Gly Asn Thr Ser Phe
                260                 265                 270

Tyr Gly Pro Gly Ser Ser Phe Thr Leu Asp Thr Thr Lys Lys Leu Thr
                275                 280                 285

Val Val Thr Gln Phe Glu Thr Ser Gly Ala Ile Asn Arg Tyr Tyr Val
290                 295                 300

Gln Asn Gly Val Thr Phe Gln Gln Pro Asn Ala Glu Leu Gly Ser Tyr
305                 310                 315                 320

Ser Gly Asn Glu Leu Asn Asp Asp Tyr Cys Thr Ala Glu Glu Ala Glu
                    325                 330                 335

Phe Gly Gly Ser Ser Phe Ser Asp Lys Gly Gly Leu Thr Gln Phe Lys
                340                 345                 350

Lys Ala Thr Ser Gly Gly Met Val Leu Val Met Ser Leu Trp Asp Asp
                355                 360                 365

Tyr Tyr Ala Asn Met Leu Trp Leu Asp Ser Thr Tyr Pro Thr Asn Glu
370                 375                 380

Thr Ser Ser Thr Pro Gly Ala Val Arg Gly Ser Cys Ser Thr Ser Ser
385                 390                 395                 400

Gly Val Pro Ala Gln Leu Glu Ser Gln Ser Asn Ala Lys Val Val Tyr
                    405                 410                 415

Ser Asn Ile Lys Phe Gly Pro Ile Gly Ser Thr Gly Asn Pro Ser Gly
                420                 425                 430

Gly Asn Pro Pro Gly Gly Asn Pro Pro Gly Thr Thr Thr Thr Arg Arg
                435                 440                 445

Pro Ala Thr Thr Thr Gly Ser Ser Pro Gly Pro Thr Gln Thr His Tyr
450                 455                 460

Gly Gln Cys Gly Gly Ile Gly Tyr Ser Gly Pro Thr Val Cys Ala Ser
465                 470                 475                 480
```

```
Gly Thr Thr Cys Gln Val Leu Asn Glu Tyr Tyr Ser Gln Cys Leu
            485                 490                 495

<210> SEQ ID NO 17
<211> LENGTH: 19
<212> TYPE: DNA
<213> ORGANISM: Artificial Sequence
<220> FEATURE:
<223> OTHER INFORMATION: primer

<400> SEQUENCE: 17
atgtatcgga agttggccg                                               19

<210> SEQ ID NO 18
<211> LENGTH: 19
<212> TYPE: DNA
<213> ORGANISM: Artificial Sequence
<220> FEATURE:
<223> OTHER INFORMATION: primer

<400> SEQUENCE: 18
ttacaggcac tgagagtag                                               19
```

CBH1 HOMOLOGS AND VARIANT CBH1 CELLULASES

CROSS-REFERENCE TO RELATED APPLICATIONS

This application is a continuation of U.S. patent application Ser. No. 10/804,785, filed Mar. 19, 2004, now U.S. Pat. No. 7,452,707 which claims priority to U.S. Provisional Application No. 60/456,368 filed Mar. 21, 2003 and to U.S. Provisional Application No. 60/458,696 filed Mar. 27, 2003, all herein incorporated by reference.

STATEMENT AS TO RIGHTS TO INVENTIONS MADE UNDER FEDERALLY SPONSORED RESEARCH AND DEVELOPMENT

Portions of this work were funded by Subcontract No. ZCO-0-30017-01 with the National Renewable Energy Laboratory under Prime Contract No. DE-AC36-99GO10337 with the U.S. Department of Energy. Accordingly, the United States Government may have certain rights in this invention.

FIELD OF THE INVENTION

This invention relates to homologs and variants of *Hypocrea jecorina* (*Trichoderma reesei*) CBH1. The present invention relates to isolated nucleic acid sequences which encode polypeptides having cellobiohydrolase activity. The invention also relates to nucleic acid constructs, vectors, and host cells comprising the nucleic acid sequences as well as methods for producing recombinant variant CBH polypeptides and novel homologs of *H. jecorina* CBH1.

REFERENCES

Altschul, S. F., et al., J. Mol. Biol. 215:403-410, 1990.
Altschul, S. F., et al., Nucleic Acids Res. 25:3389-3402, 1997.
Aro, N., et al., J. Biol. Chem., 10.1074/M003624200, Apr. 13, 2001.
Aubert, J. P. et al., Ed., Biochemistry and genetics of cellulose degradation; Proceedings of a symposium organized by the Federation of the Microbiological Societies and the French Society for Microbiology on September 7-9 1987, Academic Press, 1988.
Ausubel G. M., et al. CURRENT PROTOCOLS IN MOLECULAR BIOLOGY, John Wiley & Sons, New York, N.Y., 1993.
Baldwin, D., et al., Curr. Opin. Plant Biol. 2(2):96-103, 1999.
Baulcombe, D., Arch. Virol. Suppl. 15:189-201, 1999.
Bhikhabhai, R. et al., J. Appl. Biochem. 6:336, 1984.
Brumbauer, A. et al, Bioseparation 7:287-295, 1999.
Carter et al., Nucl. Acids Res. 13:4331, 1986.
Chen et al., Biochem. Biophys. Acta. 1121:54-60, 1992.
Coligan, J. E. et al., eds., CURRENT PROTOCOLS IN IMMUNOLOGY, 1991.
Colhen, A., et al., Journal of Chromatography A 910:275-284, 2001.
Coughlan, et al., BIOCHEMISTRY AND GENETICS OF CELLULOSE DEGRADATION.
Cummings and Fowler, Curr. Genet. 29:227-233, 1996.
Dayhoff et al. in Alas of Protein Sequence and Structure, Volume 5, Supplement 3, Chapter 22, pp. 345-352, 1978.
Deutscher, M. P., Methods Enzymol. 182:779-80, 1990.
Doolittle, R. F., OF URFS AND ORFS a Primer on How to Analyze Derived Amino Acid Sequences, University Science Books, Mill Valley, Calif., 1986.
Ellouz, S. et al., J. Chromatography 396:307, 1987.
Fields and Song, Nature 340:245-246, 1989.
Filho, et al. Can. J. Microbiol. 42:1-5, 1996.
Fliess, A., et al., Eur. J. Appl. Microbiol. Biotechnol. 17:314, 1983.
Freer, et al. J. Biol. Chem. 268:9337-9342, 1993.
Freshney, R. I., ed., ANIMAL CELL CULTURE: A PRACTICAL APPROACH, 19867.
Goyal, A. et al. Bioresource Technol. 36:37, 1991.
Halldorsdottir, S et al., Appl Microbiol Biotechnol. 49(3): 277-84, 1998.
Hu et al., Mol Cell Biol. 11:5792-9, 1991.
Hemmpel, W. H. ITB Dyeing/Printing/Finishing 3:5-14, 1991.
Herr et al., Appl. Microbiol. Biotechnol. 5:29-36, 1978.
Jakobovits, A, et al., Ann N Y Acad Sci 764:525-35, 1995.
Jakobovits, A, Curr Opin Biotechnol 6(5):561-6, 1995.
Jones et al., Nature 321:522-525, 1986.
Kawaguchi, T et al., Gene 173(2):287-8, 1996.
Knowles, J. et al., TIBTECH 5, 255-261, 1987.
Kohler and Milstein, Nature 256:495, 1975.
Krishna, S. et al., Bioresource Tech. 77:193-196, 2001.
Kumar, A., et al., Textile Chemist and Colorist 29:3742, 1997.
Lehtio, J. et al., FEMS Microbiology Letters 195:197-204, 2000
Li and Ljungdahl Appl. Environ. Microbiol. 62:209-213, 1996.
Linder, M. and Teeri, T. T., Biotechnol. 57:15-28, 1997.
Medve, J. et al., J. Chromatography A 808:153, 1998.
Ohmiya et al., Biotechnol. Gen. Engineer. Rev. 14:365-414, 1997.
Ooi et al., Nucleic Acids Res. 18(19):5884, 1990.
Ortega et al., International Biodeterioration and Biodegradation 47:7-14, 2001.
Penttila et al., Yeast 3:175-185, 1987.
Penttila et al., Gene 63: 103-112, 1988.
Pere, J., et al., In Proc. Tappi Pulping Conf., Nashville, Tenn., 27-31, pp. 693-696, 1996.
Riechmann et al., Nature 332:323-327, 1988.
Rothstein et al., Gene 55:353-356, 1987.
Saarilahti et al., Gene 90:9-14, 1990.
Sakamoto et al., Curr. Genet. 27:435-439, 1995.
Saloheimo M, et al., Gene 63:11-22, 1988.
Sambrook et al., MOLECULAR CLONING: A LABORATORY MANUAL (Second Edition), Cold Spring Harbor Press, Plainview, N.Y., 1989.
Schulein, Methods Enzymol., 160, 25, pages 234 et seq, 1988.
Scopes, Methods Enzymol. 90 Pt E:479-90, 1982.
Spilliaert R, et al., Eur J. Biochem. 224(3):923-30, 1994.
Stahlberg, J. et al., BiTechnol. 9:286-290, 1991.
Strathern et al., eds. (1981) The Molecular Biology of the Yeast *Saccharomyces*.
Suumakki, A. et al., Cellulose 7:189-209, 2000.
Te'o, J. et al., FEMS Microbiology Letters 190:13-19, 2000.
Van Tilbeurgh, H. et al., FEBS Lett. 169:215-218, 1984.
Timberlake et al., Cell 26:29-37, 1981.
Tomaz, C. and Queiroz, J., J. Chromatography A 865:123-128, 1999.
Tomme, P. et al., Eur. J. Biochem. 170:575-581, 1988.
Torno, J. et al., EMBO J. 15:5739-5751, 1996.
Tyndall, R. M., Textile Chemist and Colorist 24:23-26, 1992.
Van Rensburg et al., Yeast 14:67-76, 1998.
Van Tilbeurgh, H. et al., FEBS Lett. 204:223-227, 1986.
Verhoeyen et al., Science 239:1534-1536, 1988.
Warrington, et al., *Genomics* 13:803-808, 1992.
Wells et al., Gene 34:315, 1985.

Wells et al., Philos. Trans. R. Soc. London SerA 317:415, 1986.
Wood, Biochem. Soc. Trans., 13, pp. 407-410, 1985.
Wood et al., METHODS IN ENZYMOLOGY, 160, 25, p. 87 et seq., Academic Press, New York, 1988.
Zoller et al., Nucl. Acids Res. 10:6487, 1987.

BACKGROUND OF THE INVENTION

Cellulose and hemicellulose are the most abundant plant materials produced by photosynthesis. They can be degraded and used as an energy source by numerous microorganisms, including bacteria, yeast and fungi, that produce extracellular enzymes capable of hydrolysis of the polymeric substrates to monomeric sugars (Aro et al., 2001). As the limits of non-renewable resources approach, the potential of cellulose to become a major renewable energy resource is enormous (Krishna et al., 2001). The effective utilization of cellulose through biological processes is one approach to overcoming the shortage of foods, feeds, and fuels (Ohmiya et al., 1997).

Cellulases are enzymes that hydrolyze cellulose (beta-1,4-glucan or beta D-glucosidic linkages) resulting in the formation of glucose, cellobiose, cellooligosaccharides, and the like. Cellulases have been traditionally divided into three major classes: endoglucanases (EC 3.2.1.4) ("EG"), exoglucanases or cellobiohydrolases (EC 3.2.1.91) ("CBH") and beta-glucosidases ([beta]-D-glucoside glucohydrolase; EC 3.2.1.21) ("BG"). (Knowles et al., 1987; Shulein, 1988). Endoglucanases act mainly on the amorphous parts of the cellulose fibre, whereas cellobiohydrolases are also able to degrade crystalline cellulose (Nevalainen and Penttila, 1995). Thus, the presence of a cellobiohydrolase in a cellulase system is required for efficient solubilization of crystalline cellulose (Suumakki, et al. 2000). Beta-glucosidase acts to liberate D-glucose units from cellobiose, cello-oligosaccharides, and other glucosides (Freer, 1993).

Cellulases are known to be produced by a large number of bacteria, yeast and fungi. Certain fungi produce a complete cellulase system capable of degrading crystalline forms of cellulose, such that the cellulases are readily produced in large quantities via fermentation. Filamentous fungi play a special role since many yeast, such as *Saccharomyces cerevisiae*, lack the ability to hydrolyze cellulose. See, e.g., Aro et al., 2001; Aubert et al., 1988; Wood et al., 1988, and Coughlan, et al.

The fungal cellulase classifications of CBH, EG and BG can be further expanded to include multiple components within each classification. For example, multiple CBHs, EGs and BGs have been isolated from a variety of fungal sources including *Trichoderma reesei* which contains known genes for 2 CBHs, i.e., CBH1 and CBH II, at least 8 EGs, i.e., EG I, EG II, EG III, EGIV, EGV, EGVI, EGVII and EGVIII, and at least 5 BGs, i.e., BG1, BG2, BG3, BG4 and BG5.

In order to efficiently convert crystalline cellulose to glucose the complete cellulase system comprising components from each of the CBH, EG and BG classifications is required, with isolated components less effective in hydrolyzing crystalline cellulose (Filho et al., 1996). A synergistic relationship has been observed between cellulase components from different classifications. In particular, the EG-type cellulases and CBH-type cellulases synergistically interact to more efficiently degrade cellulose. See, e.g., Wood, 1985.

Cellulases are known in the art to be useful in the treatment of textiles for the purposes of enhancing the cleaning ability of detergent compositions, for use as a softening agent, for improving the feel and appearance of cotton fabrics, and the like (Kumar et al., 1997).

Cellulase-containing detergent compositions with improved cleaning performance (U.S. Pat. No. 4,435,307; GB App. Nos. 2,095,275 and 2,094,826) and for use in the treatment of fabric to improve the feel and appearance of the textile (U.S. Pat. Nos. 5,648,263, 5,691,178, and 5,776,757; GB App. No. 1,368,599; M. Yamagishi, "*Reforming of Cellulosic Fiber with Cellulase*," The Shizuoka Prefectural Hammamatsu Textile Industrial Research Institute Report, Vol. 24, pp. 54-61, 1986), have been described.

Hence, cellulases produced in fungi and bacteria have received significant attention. In particular, fermentation of *Trichoderma* spp. (e.g., *Trichoderma longibrachiatum* or *Trichoderma reesei*) has been shown to produce a complete cellulase system capable of degrading crystalline forms of cellulose.

Although cellulase compositions have been previously described, there remains a need for new and improved cellulase compositions for use in household detergents, stonewashing compositions or laundry detergents, etc. Cellulases that exhibit improved performance are of particular interest.

BRIEF SUMMARY OF THE INVENTION

The invention provides an isolated cellulase protein, identified herein as a desired cellulase, and nucleic acids which encode the desired cellulase. The desired cellulase may be selected from the group consisting of a variant CBH1 from *Hypocrea jecorina* and a novel CBH1 from *Hypocrea schweinitzii, Hypocrea odientalis, Trichoderma pseudokoningii* or *Trichoderma konilangbra*.

A variant CBH1 cellulase is provided, wherein the variant comprises a substitution or deletion at a position corresponding to one or more of residues L6, S8, P13, Q17, G22, T24, Q27, T41, S47, N49, T59, T66, A68, C71, A77, G88, N89, A100, N103, A112, S113, L125, T160, Y171, Q186, E193, S195, C210, M213, L225, T226, P227, T232, E236, E239, G242, T246, D249, N250, R251, Y252, D257, D259, S278, T281, L288, E295, T296, S297, A299, N301, F311, L318, E325, N327, D329, T332, A336, S341, S342, F352, K354, T356, G359, D368, Y371, N373, T380, Y381, N384, V393, R394, V407, P412, T417, F418 G430, N436, G440, P443, T445, Y466, T478, A481 and/or N490 in CBH1 from *Hypocrea jecorina*.

In a second aspect, the variant CBH1 comprises a substitution at a position corresponding to one or more of residues Q186(E), S195(A/F), E239S, G242(H/Y/N/S/T/D/A), D249 (K/L/Y/C/I/V/W/T/N/M), E325(S/T), T332(A/H/Y/L/K), and P412(T/S/A).

In a second embodiment the invention provides a *Hypocrea orientalis* CBH1.

In a third embodiment the invention provides a *Hypocrea schweinitzii* CBH1.

In a fourth embodiment, there is provided a *Trichoderma konilangbra* CBH1.

In a fifth embodiment, there is provided a *Trichoderma pseudokoningii* CBH1.

In another embodiment of the invention, a nucleic acid that encodes an inventive desired cellulase is provided. In another embodiment, the DNA is in a vector. In a further embodiment, the vector is used to transform a host cell.

In another embodiment of this invention, a method for producing an inventive desired cellulase is provided. The method comprises the steps of culturing a host cell transformed with a nucleic acid encoding a desired cellulase in a suitable culture medium under suitable conditions to produce the desired cellulase and obtaining the desired cellulase so produced.

In yet another embodiment of the invention, a detergent comprising a surfactant and a desired cellulase is provided. In one aspect of this invention, the detergent is a laundry or a dish detergent. In second aspect of this invention, the desired CBH1 cellulase is used in the treatment of a cellulose containing textile, in particular. In the stonewashing or indigo dyed denim. Alternatively, the cellulase of this invention can be used as a feed additive, in the treatment of wood pulp, and in the reduction of biomass to glucose.

BRIEF DESCRIPTION OF THE DRAWINGS

FIG. 1 shows the nucleic acid (lower line) (SEQ ID NO:1) and amino acid (upper line) (SEQ ID NO:2) sequence of the wild type Cel7A (CBH1) from *H. jecorina*.

FIGS. 2A and 2C show the amino acid alignment of the Cel7A family members *H. jecorina* (also referred to as *T. reesei*) (SEQ ID NO:2), *H. odientalis* (SEQ ID NO:5), *H. schweinitzii* (SEQ ID NO:8), *T. konilangbra* (SEQ ID NO:11) and *T. pseudokoningii* (SEQ ID NO:14). The consensus sequence is also shown.

FIG. 3 is the genomic DNA sequence for *H. orientalis* CBH1 (SEQ ID NO:3). Introns are in bold and underlined.

FIG. 4 is the signal sequence (A) (SEQ ID NO:4) and mature amino acid sequence (B) (SEQ ID NO:5) for *H. orientalis* CBH1.

FIG. 5 is the genomic DNA sequence for *H. schweinitzii* CBH1 (SEQ ID NO:6). Introns are in bold and underlined.

FIG. 6 is the signal sequence (A) (SEQ ID NO:7) and mature amino acid sequence (B) (SEQ ID NO:8) for *H. schweinitzii* CBH1.

FIG. 7 is the genomic DNA sequence for *T. konilangbra* CBH1 (SEQ ID NO:9). Introns are in bold and underlined.

FIG. 8 is the signal sequence (A) (SEQ ID NO:10) and mature amino acid sequence (B) (SEQ ID NO:11) for *T. konilangbra* CBH1.

FIG. 9 is the genomic DNA sequence for *T. pseudokoningii* CBH1 (SEQ ID NO:12). Introns are in bold and underlined.

FIG. 10 is the signal sequence (A) (SEQ ID NO:13) and mature amino acid sequence (B) (SEQ ID NO:14) for *T. pseudokoningii* CBH1.

FIG. 11 is the pRAX1 vector. This vector is based on the plasmid pGAPT2 except a 5259 bp HindIII fragment of *Aspergillus nidulans* genomic DNA fragment AMA1 sequence (Molecular Microbiology 1996 19:565-574) was inserted. Base 1 to 1134 contains *Aspergillus niger* glucoamylase gene promoter. Base 3098 to 3356 and 4950 to 4971 contains *Aspergillus niger* glucoamylase terminator. *Aspergillus nidulans* pyrG gene was inserted from 3357 to 4949 as a marker for fungal transformation. There is a multiple cloning site (MCS) into which genes may be inserted.

FIG. 12 is the pRAXdes2 vector backbone. This vector is based on the plasmid vector pRAX1. A Gateway cassette has been inserted into pRAX1 vector (indicated by the arrow on the interior of the circular plasmid). This cassette contains recombination sequence attR1 and attR2 and the selection marker catH and ccdB. The vector has been made according to the manual given in Gateway™ Cloning Technology: version 1 page 3438 and can only replicate in *E. coli* DB3.1 from Invitrogen; in other *E. coli* hosts the crdB gene is lethal. First a PCR fragment is made with primers containing attB1/2 recombination sequences. This fragment is recombined with pDONR201 (commercially available from Invitrogen); this vector contains attP1/2 recombination sequences with catH and ccdB in between the recombination sites. The BP clonase enzymes from Invitrogen are used to recombine the PCR fragment in this so-called ENTRY vector, clones with the PCR fragment inserted can be selected at 50 µg/ml kanamycin because clones expressing ccdB do not survive. Now the aft sequences are altered and called attL1 and attL2. The second step is to recombine this clone with the pRAXdes2 vector (containing attR1 and attR2 catH and ccdB in between the recombination sites). The LR clonase enzymes from Invitrogen are used to recombine the insert from the ENTRY vector in the destination vector. Only pRAXCBH1 vectors are selected using 100 µg/ml ampicillin because ccdB is lethal and the ENTRY vector is sensitive to ampicillin. By this method the expression vector is now prepared and can be used to transform *A. niger*.

FIG. 13 provides an illustration of the pRAXdes2cbh1 vector which was used for expression of the nucleic acids encoding the CBH1 homologs or variants in *Aspergillus*. A nucleic acid encoding a CBH1 enzyme homolog or variant was cloned into the vector by homologous recombination of the att sequences.

DETAILED DESCRIPTION

The invention will now be described in detail by way of reference only using the following definitions and examples. All patents and publications, including all sequences disclosed within such patents and publications, referred to herein are expressly incorporated by reference.

Unless defined otherwise herein, all technical and scientific terms used herein have the same meaning as commonly understood by one of ordinary skill in the art to which this invention belongs. Singleton, et al., DICTIONARY OF MICROBIOLOGY AND MOLECULAR BIOLOGY, 2D ED., John Wiley and Sons, New York (1994), and Hale & Marham, THE HARPER COLLINS DICTIONARY OF BIOLOGY, Harper Perennial, NY (1991) provide one of skill with a general dictionary of many of the terms used in this invention. Although any methods and materials similar or equivalent to those described herein can be used in the practice or testing of the present invention, the preferred methods and materials are described. Numeric ranges are inclusive of the numbers defining the range. Unless otherwise indicated, nucleic acids are written left to right in 6 to 3' orientation; amino acid sequences are written left to right in amino to carboxy orientation, respectively. Practitioners are particularly directed to Sambrook et al., 1989, and Ausubel F M et al., 1993, for definitions and terms of the art. It is to be understood that this invention is not limited to the particular methodology, protocols, and reagents described, as these may vary.

The headings provided herein are not limitations of the various aspects or embodiments of the invention which can be had by reference to the specification as a whole. Accordingly, the terms defined immediately below are more fully defined by reference to the specification as a whole.

All publications cited herein are expressly incorporated herein by reference for the purpose of describing and disclosing compositions and methodologies which might be used in connection with the invention.

I. DEFINITIONS

"Cellulase," "cellulolytic enzymes" or "cellulase enzymes" means bacterial, or fungal exoglucanases or exo-cellobiohydrolases, and/or endoglucanases, and/or β-glucosidases. These three different types of cellulase enzymes act synergistically to convert cellulose and its derivatives to glucose.

Many microbes make enzymes that hydrolyze cellulose, including the wood rotting fungus *Trichoderma*, the compost bacteria *Themomonospora, Bacillus,* and *Cellulomonas; Streptomyces*; and the fungi *Humicola, Aspergillus* and *Fusarium*. The enzymes made by these microbes are mixtures of proteins with three types of actions useful in the conversion of cellulose to glucose: endoglucanases (EG), cellobiohydrolases (CBH), and beta-glucosidase.

A "desired cellulase" as used herein means any one of the following:
 a) a variant CBH1 from *Hyprocrea jecorina* according to the present invention;
 b) a CBH1 homolog from *H. orientalis;*
 c) a CBH1 homolog from *H. schweinitzii,*
 d) a CBH1 homolog from *T. konilangbra;*
 e) a CBH1 homolog from *T. pseudokoningii* and
 f) a polypeptide encoded by a nucleic acid that hybridizes with the nucleic acid that encodes any one of a-e under stringent conditions.

A "desired cellulase-encoding nucleic acid" as used herein means any one of the following:
 a) a nucleic acid encoding a variant CBH1 from *Hyprocrea jecorina* according to the present invention;
 b) a nucleic acid encoding a CBH1 homolog from *H. orientalis* having the sequence shown in FIG. 3;
 c) a nucleic acid encoding a CBH1 homolog from *H. schweinitzii* having the sequence shown in FIG. 5;
 d) a nucleic acid encoding a CBH1 homolog from *T. konilangbra* having the sequence shown in FIG. 7;
 e) a nucleic acid encoding a CBH1 homolog from *T. pseudokoningii* having the sequence shown in FIG. 9 and
 f) a nucleic acid that hybridizes with any one of the nucleic acids provided for by a-e, above, under stringent conditions "Variant" means a protein which is derived from a precursor protein (e.g., the native protein) by substitution of one or more amino acids at one or a number of different sites in the amino acid sequence. The preparation of an enzyme variant is preferably achieved by modifying a DNA sequence which encodes for the native protein, transformation of that DNA sequence into a suitable host, and expression of the modified DNA sequence to form the derivative enzyme or enzyme variant. The variant CBH1 enzyme of the invention includes peptides comprising altered amino acid sequences in comparison with a precursor enzyme amino add sequence wherein the variant CBH enzyme retains the characteristic cellulolytic nature of the precursor enzyme but which may have altered properties in some specific aspect. For example, a variant CBH enzyme may have an increased pH optimum or increased temperature or oxidative stability but will retain its characteristic cellulolytic activity.

As used herein, the term "gene" means the segment of DNA involved in producing a polypeptide chain, that may or may not include regions preceding and following the coding region, e.g. 5' untranslated (5' UTR) or "leader" sequences and 3' UTR or "trailer" sequences, as well as intervening sequences (introns) between individual coding segments (exons).

The "filamentous fungi" of the present invention are eukaryotic microorganisms and include all filamentous forms of the subdivision Eumycotina (see Alexopoulos, C. J. (1962), Introductory Mycology, New York: Wiley). These fungi are characterized by a vegetative mycelium with a cell wall composed of chitin, cellulose, and other complex polysaccharides. The filamentous fungi of the present invention are morphologically, physiologically, and genetically distinct from yeasts. Vegetative growth by filamentous fungi is by hyphal elongation and carbon catabolism is obligately aerobic. In contrast, vegetative growth by yeasts such as *S. cerevisiae* is by budding of a unicellular thallus, and carbon catabolism may be fermentative. *S. cerevisiae* has a prominent, very stable diploid phase, whereas diploids exist only briefly prior to melosis in filamentous fungi, e.g., *Aspergilli* and *Neurospora*. Although pseudohyphal growth may be exhibited by yeast under certain conditions it is to be understood that this does not bring the yeast within the definition of filamentous fungi. *S. cervisiae* has 17 chromosomes as opposed to 8 and 7 for *A. nidulans* and *N. crassa* respectively. Further illustrations of differences between *S. cerevisiae* and filamentous fungi include the inability of *S. cerevisiae* to process *Aspergillus* and *Trichoderma* introns and the inability to recognize many transcriptional regulators of filamentous fungi (Innis, M. A. et al. (1985) Science, 228, 21-26).

The term "heterologous" when used with reference to portions of a nucleic acid indicates that the nucleic add comprises two or more subsequences that are not normally found in the same relationship to each other in nature. For instance, the nucleic acid is typically recombinantly produced, having two or more sequences, e.g., from unrelated genes arranged to make a new functional nucleic acid, e.g., a promoter from one source and a coding region from another source. Similarly, a heterologous protein will often refer to two or more subsequences that are not found in the same relationship to each other in nature (e.g., a fusion protein).

A "heterologous" nucleic add construct or sequence has a portion of the sequence which is not native to the cell in which it is expressed. Heterologous, with respect to a control sequence refers to a control sequence (i.e. promoter or enhancer) that does not function in nature to regulate the same gene the expression of which it is currently regulating. Generally, heterologous nucleic acid sequences are not endogenous to the cell or part of the genome in which they are present, and have been added to the cell, by infection, transfection, transformation, microinjecton, electroporation, or the like. A "heterologous" nucleic acid construct may contain a control sequence/DNA coding sequence combination that is the same as, or different from a control sequence/DNA coding sequence combination found in the native cell.

The terms "isolated" or "purified" as used herein refer to a nucleic acid or amino acid that is removed from at least one component with which it is naturally associated.

As used herein, the terms "promoter" refers to a nucleic acid sequence that functions to direct transcription of a downstream gene. The promoter will generally be appropriate to the host cell in which the target gene is being expressed. The promoter together with other transcriptional and translational regulatory nucleic acid sequences (also termed "control sequences") are necessary to express a given gene. In general, the transcriptional and translational regulatory sequences include, but are not limited to, promoter sequences, ribosomal binding sites, transcriptional start and stop sequences, translational start and stop sequences, and enhancer or activator sequences.

Generally, a "promoter sequence" is a DNA sequence which is recognized by the particular filamentous fungus for expression purposes. A "constitutive" promoter is a promoter that is active under most environmental and developmental conditions. An "inducible" promoter is a promoter that is active under environmental or developmental regulation. An example of an inducible promoter useful in the present invention is the *T. reesei* (*H. jecorina*) cbh1 promoter which is deposited in GenBank under Accession Number D86235. In another aspect the promoter is a cbh II or xylanase promoter from *H. jecorina*.

Exemplary promoters include the promoter from the *A. awamori* or *A. niger* glucoamylase genes (Nunberg, J. H. et al. (1984) Mol. Cell. Biol. 4, 2306-2315; Boel, E. et al. (1984) EMBO J. 3, 1581-1585), the Mucor miehei carboxyl protease gene, the Hypocrea jecorina cellobiohydrolase I gene (Shoemaker, S. P. et al. (1984) European Patent Application No. EP00137280A1), the *A. nidulans* trpC gene (Yelton, M. et al. (1984) Proc. Natl. Acad. Sci. USA 81, 1470-1474; Mullaney, E. J. et al. (1985) Mol. Gen. Genet. 199, 37-45) the *A. nidulans* alcA gene (Lockington, R. A. et al. (1985) Gene 33, 137-149), the *A. nidulans* tpiA gene (McKnight, G. L. et al. (1986) Cell 46, 143-147), the *A. nidulans* amdS gene (Hynes, M. J. et al. (1983) Mol. Cell Biol. 3, 1430-1439), the *H. jecorina* xln1 gene, the *H. jecorina* cbh2 gene, the *H. jecorina* eg1 gene, the *H. jecorina* eg2 gene, the *H. jecorina* eg3 gene, and higher eukaryotic promoters such as the SV40 early promoter (Barclay, S. L. and E. Meller (1983) Molecular and Cellular Biology 3, 2117-2130).

A nucleic acid is "operably linked" when it is placed into a functional relationship with another nucleic acid sequence. For example, DNA encoding a secretory leader, i.e., a signal peptide, is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are contiguous, and, in the case of a secretory leader, contiguous and in reading phase. However, enhancers do not have to be contiguous. Linking is accomplished by ligation at convenient restriction sites. If such sites do not exist, the synthetic oligonucleotide adaptors or linkers are used in accordance with conventional practice. Thus, the term "operably linked" refers to a functional linkage between a nucleic add expression control sequence (such as a promoter, or array of transcription factor binding sites) and a second nucleic acid sequence, wherein the expression control sequence directs transcription of the nucleic acid corresponding to the second sequence.

"Chimeric gene" or "heterologous nucleic acid construct", as defined herein refers to a non-native gene (i.e., one that has been introduced into a host) that may be composed of parts of different genes, including regulatory elements. A chimeric gene construct for transformation of a host cell is typically composed of a transcriptional regulatory region (promoter) operably linked to a heterologous protein coding sequence, or, in a selectable marker chimeric gene, to a selectable marker gene encoding a protein conferring antibiotic resistance to transformed cells. A typical chimeric gene of the present invention, for transformation into a host cell, includes a transcriptional regulatory region that is constitutive or inducible, a protein coding sequence, and a terminator sequence. A chimeric gene construct may also include a second DNA sequence encoding a signal peptide if secretion of the target protein is desired.

The term "recombinant" when used with reference, e.g., to a cell, or nucleic acid, protein, or vector, indicates that the cell, nucleic acid, protein or vector, has been modified by the introduction of a heterologous nucleic acid or protein or the alteration of a native nucleic acid or protein, or that the cell is derived from a cell so modified. Thus, for example, recombinant cells express genes that are not found within the native (non-recombinant) form of the cell or express native genes that are otherwise abnormally expressed, under expressed or not expressed at all.

The term "secretory signal sequence" denotes a DNA sequence that encodes a polypeptide (a "secretory peptide") that, as a component of a larger polypeptide, directs the larger polypeptide through a secretory pathway of a cell in which it is synthesized. The larger peptide is commonly cleaved to remove the secretory peptide during transit through the secretory pathway.

As used herein, the phrases "whole cellulase preparation" and "whole cellulase composition" are used interchangeably and refer to both naturally occurring and non-naturally occurring compositions. A "naturally occurring" composition is one produced by a naturally occurring source and which comprises one or more cellobiohydrolase-type, one or more endoglucanase-type, and one or more β-glucosidase components wherein each of these components is found at the ratio produced by the source. A naturally occurring composition is one that is produced by an organism unmodified with respect to the cellulolytic enzymes such that the ratio of the component enzymes is unaltered from that produced by the native organism.

A "non-naturally occurring" composition encompasses those compositions produced by: (1) combining component cellulolytic enzymes either in a naturally occurring ratio or non-naturally occurring, i.e., altered, ratio; or (2) modifying an organism to overexpress or underexpress one or more cellulolytic enzyme; or (3) modifying an organism such that at least one cellulolytic enzyme is deleted.

"Equivalent residues" may also be defined by determining homology at the level of tertiary structure for a precursor cellulase whose tertiary structure has been determined by x-ray crystallography. Equivalent residues are defined as those for which the atomic coordinates of two or more of the main chain atoms of a particular amino acid residue of a cellulase and *Hypocrea jecorina* CBH (N on N, CA on CA, C on C and O on O) are within 0.13 nm and preferably 0.1 nm after alignment. Alignment is achieved after the best model has been oriented and positioned to give the maximum overlap of atomic coordinates of non-hydrogen protein atoms of the cellulase in question to the *H. jecorina* CBH1. The best model is the crystallographic model giving the lowest R factor for experimental diffraction data at the highest resolution available.

$$Rfactor = \frac{\Sigma_h |Fo(h)| - |Fc(h)|}{\Sigma_h |Fo(h)|}$$

Equivalent residues which are functionally analogous to a specific residue of *H. jecorina* CBH 1 are defined as those amino adds of a cellulase which may adopt a conformation such that they either alter, modify or contribute to protein structure, substrate binding or catalysis in a manner defined and attributed to a specific residue of the *H. jecorina* CBH1. Further, they are those residues of the cellulase (for which a tertiary structure has been obtained by x-ray crystallography) which occupy an analogous position to the extent that, although the main chain atoms of the given residue may not satisfy the criteria of equivalence on the basis of occupying a homologous position, the atomic coordinates of at least two of the side chain atoms of the residue lie with 0.13 nm of the corresponding side chain atoms of *H. jecorina* CBH.

The term "nucleic acid molecule" includes RNA, DNA and cDNA molecules. It will be understood that, as a result of the degeneracy of the genetic code, a multitude of nucleotide sequences encoding a given protein such as CBH1 may be produced. The present invention contemplates every possible variant nucleotide sequence, encoding CBH1, all of which are possible given the degeneracy of the genetic code.

As used herein, the term "vector" refers to a nucleic acid construct designed for transfer between different host cells. An "expression vector" refers to a vector that has the ability to incorporate and express heterologous DNA fragments in a foreign cell. Many prokaryotic and eukaryotic expression vectors are commercially available. Selection of appropriate expression vectors is within the knowledge of those having skill in the art.

Accordingly, an "expression cassette" or "expression vector" is a nucleic acid construct generated recombinantly or synthetically, with a series of specified nucleic acid elements that permit transcription of a particular nucleic acid in a target cell. The recombinant expression cassette can be incorporated into a plasmid, chromosome, mitochondrial DNA, plastid DNA, virus, or nucleic acid fragment. Typically, the recombinant expression cassette portion of an expression vector includes, among other sequences, a nucleic acid sequence to be transcribed and a promoter.

As used herein, the term "plasmid" refers to a circular double-stranded (ds) DNA construct used as a cloning vector, and which forms an extrachromosomal self-replicating genetic element in many bacteria and some eukaryotes.

As used herein, the term "selectable marker-encoding nucleotide sequence" refers to a nucleotide sequence which is capable of expression in cells and where expression of the selectable marker confers to cells containing the expressed gene the ability to grow in the presence of a corresponding selective agent, or under corresponding selective growth conditions.

In general, nucleic acid molecules which encode the variant CBH1 will hybridize, under moderate to high stringency conditions to the wild type sequence provided herein as SEQ ID NO: 1 (native *H. jecorina* CBH1). However, in some cases a CBH1-encoding nucleotide sequence is employed that possesses a substantially different codon usage, while the protein encoded by the CBH1-encoding nucleotide sequence has the same or substantially the same amino acid sequence as the native protein. For example, the coding sequence may be modified to facilitate faster expression of CBH1 in a particular prokaryotic or eukaryotic expression system, in accordance with the frequency with which a particular codon is utilized by the host. Te'o, et al. (2000), for example, describes the optimization of genes for expression in filamentous fungi.

A nucleic acid sequence is considered to be "selectively hybridizable" to a reference nucleic acid sequence if the two sequences specifically hybridize to one another under moderate to high stringency hybridization and wash conditions. Hybridization conditions are based on the melting temperature (Tm) of the nucleic acid binding complex or probe. For example, "maximum stringency" typically occurs at about Tm-5° C. (5° below the Tm of the probe); "high stringency" at about 5-10° below the Tm; "moderate" or "intermediate stringency" at about 10-20° below the Tm of the probe; and "low stringency" at about 20-25° below the Tm. Functionally, maximum stringency conditions may be used to Identify sequences having strict identity or near-strict identity with the hybridization probe; while high stringency conditions are used to identify sequences having about 80% or more sequence identity with the probe.

Moderate and high stringency hybridization conditions are well known in the art (see, for example, Sambrook, et al, 1989, Chapters 9 and 11, and in Ausubel, F. M., et al., 1993, expressly incorporated by reference herein). An example of high stringency conditions includes hybridization at about 42° C. in 50% formamide, 5×SSC, 5×Denhardt's solution, 0.5% SDS and 100 µg/ml denatured carrier DNA followed by washing two times in 2×SSC and 0.5% SDS at room temperature and two additional times in 0.1×SSC and 0.5% SDS at 42° C.

As used herein, the terms "transformed", "stably transformed" or "transgenic" with reference to a cell means the cell has a non-native (heterologous) nucleic acid sequence integrated into its genome or as an episomal plasmid that is maintained through multiple generations.

As used herein, the term "expression" refers to the process by which a polypeptide is produced based on the nucleic acid sequence of a gene. The process includes both transcription and translation.

The term "introduced" in the context of inserting a nucleic acid sequence into a cell, means "transfection", or "transformation" or "transduction" and includes reference to the incorporation of a nucleic acid sequence into a eukaryotic or prokaryotic cell where the nucleic acid sequence may be incorporated into the genome of the cell (for example, chromosome, plasmid, plastid, or mitochondrial DNA), converted into an autonomous replicon, or transiently expressed (for example, transfected mRNA).

It follows that the term "desired cellulase expression" refers to transcription and translation of the desired cellulase gene, the products of which include precursor RNA, mRNA, polypeptide, post-translationally processed polypeptides. By way of example, assays for CBH1 expression include Western blot for CBH1 protein, Northern blot analysis and reverse transcriptase polymerase chain reaction (RT-PCR) assays for CBH1 mRNA, and endoglucanase activity assays as described in Shoemaker S. P. and Brown R. D. Jr. (Biochim. Biophys. Acta, 1978, 523:133-146) and Schulein (1988).

The term "alternative splicing" refers to the process whereby multiple polypeptide isoforms are generated from a single gene, and involves the splicing together of nonconsecutive exons during the processing of some, but not all, transcripts of the gene. Thus a particular exon may be connected to any one of several alternative exons to form messenger RNAs. The alternatively-spliced mRNAs produce polypeptides ("splice variants") in which some parts are common while other parts are different.

By the term "host-cell" is meant a cell that contains a vector and supports the replication, and/or transcription or transcription and translation (expression) of the expression construct. Host cells for use in the present invention can be prokaryotic cells, such as *E. coli*, or eukaryotic cells such as yeast, plant, insect, amphibian, or mammalian cells. In general, host cells are filamentous fungi.

The term "cellulase" refers to a category of enzymes capable of hydrolyzing cellulose polymers to shorter cello-oligosaccharide oligomers, cellobiose and/or glucose. Numerous examples of cellulases, such as exoglucanases, exocellobiohydrolases, endoglucanases, and glucosidases have been obtained from cellulolytic organisms, particularly including fungi, plants and bacteria.

CBH1 from *Hypocrea jecorina* is a member of the Glycosyl Hydrolase Family 7 (hence Cel7) and, specifically, was the first member of that family identified in *Hypocrea jecorina* (hence Cel7A). The Glycosyl Hydrolase Family 7 contains both Endoglucanases and Cellobiohydrolases/exoglucanases, and that CBH1 is the latter. Thus, the phrases CBH1, CBH1-type protein and Cel7 cellobiohydrolases may be used interchangeably herein.

The term "cellulose binding domain" as used herein refers to portion of the amino acid sequence of a cellulase or a region of the enzyme that is involved in the cellulose binding activity of a cellulase or derivative thereof. Cellulose binding domains or modules generally function by non-covalently binding the cellulase to cellulose, a cellulose derivative or other polysaccharide equivalent thereof. Cellulose binding domains permit or facilitate hydrolysis of cellulose fibers by the structurally distinct catalytic core region, and typically function independent of the catalytic core. Thus, a cellulose binding domain will not possess the significant hydrolytic activity attributable to a catalytic core. In other words, a cellulose binding domain is a structural element of the cellulase enzyme protein tertiary structure that is distinct from the structural element which possesses catalytic activity.

As used herein, the term "surfactant" refers to any compound generally recognized in the art as having surface active qualities. Thus, for example, surfactants comprise anionic, cationic and nonionic surfactants such as those commonly found in detergents. Anionic surfactants include linear or branched alkylbenzenesulfonates; alkyl or alkenyl ether sulfates having linear or branched alkyl groups or alkenyl groups; alkyl or alkenyl sulfates; olefinsulfonates; and alkanesulfonates. Ampholytic surfactants include quaternary ammonium salt sulfonates, and betaine-type ampholytic surfactants. Such ampholytic surfactants have both the positive and negative charged groups in the same molecule. Nonionic surfactants may comprise polyoxyalkylene ethers, as well as higher fatty acid alkanolamides or alkylene oxide adduct thereof, fatty add glycerine monoesters, and the like.

As used herein, the term "cellulose containing fabric" refers to any sewn or unsewn fabrics, yarns or fibers made of cotton or non-cotton containing cellulose or cotton or non-cotton containing cellulose blends including natural cellulosics and manmade cellulosics (such as jute, flax, ramie, rayon, and lyocell).

As used herein, the term "cotton-containing fabric" refers to sewn or unsewn fabrics, yarns or fibers made of pure cotton or cotton blends including cotton woven fabrics, cotton knits, cotton denims, cotton yarns, raw cotton and the like.

As used herein, the term "stonewashing composition" refers to a formulation for use in stonewashing cellulose containing fabrics. Stonewashing compositions are used to modify cellulose containing fabrics prior to sale, i.e., during the manufacturing process. In contrast, detergent compositions are intended for the cleaning of soiled garments and are not used during the manufacturing process.

As used herein, the term "detergent composition" refers to a mixture which is intended for use in a wash medium for the laundering of soiled cellulose containing fabrics. In the context of the present invention, such compositions may include, in addition to cellulases and surfactants, additional hydrolytic enzymes, builders, bleaching agents, bleach activators, bluing agents and fluorescent dyes, caking inhibitors, masking agents, cellulase activators, antioxidants, and solubilizers.

As used herein, the term "decrease or elimination in expression of the cbh1 gene" means that either that the cbh1 gene has been deleted from the genome and therefore cannot be expressed by the recombinant host microorganism; or that the cbh1 gene has been modified such that a functional CBH1 enzyme is not produced by the host microorganism.

The term "variant cbh1 gene" or "variant CBH1" means, respectively, that the nucleic acid sequence of the cbh1 gene from *H. jecorina* has been altered by removing, adding, and/or manipulating the coding sequence or the amino acid sequence of the expressed protein has been modified consistent with the invention described herein.

As used herein, the terms "active" and "biologically active" refer to a biological activity associated with a particular protein and are used interchangeably herein. For example, the enzymatic activity associated with a protease is proteolysis and, thus, an active protease has proteolytic activity. It follows that the biological activity of a given protein refers to any biological activity typically attributed to that protein by those of skill in the art.

When employed in enzymatic solutions, the homolog or variant CBH1 component is generally added in an amount sufficient to allow the highest rate of release of soluble sugars from the biomass. The amount of homolog or variant CBH1 component added depends upon the type of biomass to be saccharified which can be readily determined by the skilled artisan. However, when employed, the weight percent of the homolog or variant CBH1 component relative to any EG type components present in the cellulase composition is from preferably about 1, preferably about 5, preferably about 10, preferably about 15, or preferably about 20 weight percent to preferably about 25, preferably about 30, preferably about 35, preferably about 40, preferably about 45 or preferably about 50 weight percent. Furthermore, preferred ranges may be about 0.5 to about 15 weight percent, about 0.5 to about 20 weight percent, from about 1 to about 10 weight percent, from about 1 to about 15 weight percent, from about 1 to about 20 weight percent, from about 1 to about 25 weight percent, from about 5 to about 20 weight percent, from about 5 to about 25 weight percent, from about 5 to about 30 weight percent, from about 5 to about 35 weight percent, from about 5 to about 40 weight percent, from about 5 to about 45 weight percent, from about 5 to about 50 weight percent, from about 10 to about 20 weight percent, from about 10 to about 25 weight percent, from about 10 to about 30 weight percent, from about 10 to about 35 weight percent, from about 10 to about 40 weight percent, from about 10 to about 45 weight percent, from about 10 to about 50 weight percent, from about 15 to about 20 weight percent, from about 15 to about 25 weight percent, from about 15 to about 30 weight percent, from about 15 to about 35 weight percent, from about 15 to about 30 weight percent, from about 15 to about 45 weight percent, from about 15 to about 50 weight percent.

II. HOST ORGANISMS

Filamentous fungi include all filamentous forms of the subdivision Eumycota and Oomycota. The filamentous fungi are characterized by vegetative mycelium having a cell wall composed of chitin, glucan, chitosan, mannan, and other complex polysaccharides, with vegetative growth by hyphal elongation and carbon catabolism that is obligately aerobic.

In the present invention, the filamentous fungal parent cell may be a cell of a species of, but not limited to, *Trichoderma*, e.g., *Trichoderma longibrachiatum, Trichoderma viride, Trichoderma koningii, Trichoderma harianum; Penicillium* sp.; *Humicola* sp., including *Humicola insolens* and *Humicola grisea; Chrysosporium* sp., including *C. lucknowense; Gliocladium* sp.; *Aspergillus* sp.; *Fusatium* sp., *Neurospora* sp., *Hypocrea* sp., and *Emericella* sp. As used herein, the term "*Trichoderma*" or "*Trichoderma* sp." refers to any fungal strains which have previously been classified as *Trichoderma* or are currently classified as *Trichoderma*.

In one preferred embodiment, the filamentous fungal parent cell is an *Aspergillus niger, Aspergillus awamori, Aspergillus aculeatus,* or *Aspergillus nidulans* cell.

In another preferred embodiment, the filamentous fungal parent cell is a *Trichoderma reesei* cell.

III. CELLULASES

Cellulases are known in the art as enzymes that hydrolyze cellulose (beta-1,4-glucan or beta D-glucosidic linkages)

resulting in the formation of glucose, cellobiose, cellooligosaccharides, and the like. As set forth above, cellulases have been traditionally divided into three major classes: endoglucanases (EC 3.2.1.4) ("EG"), exoglucanases or cellobiohydrolases (EC 3.2.1.91) ("CBH") and beta-glucosidases (EC 3.2.1.21) ("BG"). (Knowles, et al., 1987; Schulein, 1988).

Certain fungi produce complete cellulase systems which include exo-cellobiohydrolases or CBH-type cellulases, endoglucanases or EG-type cellulases and beta-glucosidases or BG-type cellulases (Schulein, 1988). However, sometimes these systems lack CBH-type cellulases and bacterial cellulases also typically include little or no CBH-type cellulases. In addition, it has been shown that the EG components and CBH components synergistically interact to more efficiently degrade cellulose. See, e.g., Wood, 1985. The different components, i.e., the various endoglucanases and exocellobiohydrolases in a multi-component or complete cellulase system, generally have different properties, such as isoelectric point, molecular weight, degree of glycosylation, substrate specificity and enzymatic action patterns.

Cellulase compositions have also been shown to degrade cotton-containing fabrics, resulting in reduced strength loss in the fabric (U.S. Pat. No. 4,822,516), contributing to reluctance to use cellulase compositions in commercial detergent applications. Cellulase compositions comprising endoglucanase components have been suggested to exhibit reduced strength loss for cotton-containing fabrics as compared to compositions comprising a complete cellulase system.

Cellulases have also been shown to be useful in degradation of cellulase biomass to ethanol (wherein the cellulase degrades cellulose to glucose and yeast or other microbes further ferment the glucose into ethanol), in the treatment of mechanical pulp (Pere et al., 1996), for use as a feed additive (WO 91/04673) and in grain wet milling.

Most CBHs and EGs have a multidomain structure consisting of a core domain separated from a cellulose binding domain (CBD) by a linker peptide (Suumakki et al., 2000). The core domain contains the active site whereas the CBD interacts with cellulose by binding the enzyme to it (van Tilbeurgh et al., 1986; Tomme et al., 1988). The CBDs are particularly important in the hydrolysis of crystalline cellulose. It has been shown that the ability of cellobiohydrolases to degrade crystalline cellulose clearly decreases when the CBD is absent (Linder and Teeri, 1997). However, the exact role and action mechanism of CBDs is still a matter of speculation. It has been suggested that the CBD enhances the enzymatic activity merely by increasing the effective enzyme concentration at the surface of cellulose (Stahlberg et al., 1991), and/or by loosening single cellulose chains from the cellulose surface (Tormo et al., 1996). Most studies concerning the effects of cellulase domains on different substrates have been carried out with core proteins of cellobiohydrolases, as their core proteins can easily be produced by limited proteolysis with papain (Tomme et al., 1988). Numerous cellulases have been described in the scientific literature, examples of which include: from *Trichoderma reesei* Shoemaker, S. et al., Bio/Technology, 1:691-696, 1983, which discloses CBHI; Teeri, T. et al., Gene, 51:43-52, 1987, which discloses CBHII. Cellulases from species other than *Trichoderma* have also been described e.g., Ooi et al., 1990, which discloses the cDNA sequence coding for endoglucanase F1-CMC produced by *Aspergillus aculeatus*; Kawaguchi T et al., 1996, which discloses the cloning and sequencing of the cDNA encoding beta-glucosidase 1 from *Aspergillus aculeatus*; Sakamoto et al., 1995, which discloses the cDNA sequence encoding the endoglucanase CMCase-1 from *Aspergillus kawachii* IFO 4308; Saarilahti et al, 1990 which discloses an endoglucanase from *Erwinia carotovara*; Spilliaert R, et al., 1994, which discloses the cloning and sequencing of bglA, coding for a thermostable beta-glucanase from *Rhodothermus marinus*; and Haldorsdottir S et al., 1998, which discloses the cloning, sequencing and overexpression of a *Rhodothermus marinus* gene encoding a thermostable cellulase of glycosyl hydrolase family 12. However, there remains a need for identification and characterization of novel cellulases, with improved properties, such as improved performance under conditions of thermal stress or in the presence of surfactants, increased specific activity, altered substrate cleavage pattern, and/or high level expression in vitro.

The development of new and improved cellulase compositions that comprise varying amounts CBH-type cellulase is of interest for use: (1) in detergent compositions that exhibit enhanced cleaning ability, function as a softening agent and/or improve the feel of cotton fabrics (e.g., "stone washing" or "biopolishing"); (2) in compositions for degrading wood pulp or other biomass into sugars (e.g., for bio-ethanol production); and/or (3) in feed compositions.

IV. MOLECULAR BIOLOGY

In one embodiment this invention provides for the expression of desired cellulase genes under control of a promoter functional in a filamentous fungus. Therefore, this invention relies on routine techniques in the field of recombinant genetics. Basic texts disclosing the general methods of use in this invention include Sambrook et al., *Molecular Cloning, A Laboratory Manual* (2nd ed. 1989); Kriegler, *Gene Transfer and Expression: A Laboratory Manual* (1990); and Ausubel et al., eds., *Current Protocols in Molecular Biology* (1994)).

A. Methods for Identifying Homologous CBH1 Genes

The nucleic acid sequence for the wild type *H. jecorina* CBH1 is shown in FIG. 1. The invention, in one aspect, encompasses a nucleic acid molecule encoding a CBH I homolog described herein. The nucleic acid may be a DNA molecule.

Techniques that can be used to isolate homologous CBH1-encoding DNA sequences are well known in the art and include, but are not limited to, cDNA and/or genomic library screening with a homologous DNA probes and expression screening with activity assays or antibodies against CBH1. Any of these methods can be found in Sambrook, et al. or in CURRENT PROTOCOLS IN MOLECULAR BIOLOGY, F. Ausubel, et al., ed. Greene Publishing and Wiley-Interscience, New York (1987) ("Ausubel").

B. Methods of Mutating CBH Nucleic Acid Sequences

Any method known in the art that can introduce mutations is contemplated by the present invention.

The present invention relates to the expression, purification and/or isolation and use of variant CBH1. These enzymes are preferably prepared by recombinant methods utilizing the cbh gene from *H. jecorina*.

After the isolation and cloning of the cbh1 gene from *H. jecorina*, other methods known in the art, such as site directed mutagenesis, are used to make the substitutions, additions or deletions that correspond to substituted amino acids in the expressed CBH1 variant. Again, site directed mutagenesis and other methods of incorporating amino acid changes in expressed proteins at the DNA level can be found in Sambrook, et al. and Ausubel, et al.

DNA encoding an amino acid sequence variant of the *H. jecorina* CBH1 is prepared by a variety of methods known in the art. These methods include, but are not limited to, preparation by site-directed (or oligonucleotide-mediated) mutagenesis, PCR mutagenesis, and cassette mutagenesis of an earlier prepared DNA encoding the *H. jecorina* CBH1.

Site-directed mutagenesis is a preferred method for preparing substitution variants. This technique is well known in the art (see, e.g., Carter et al. Nucleic Acids Res. 13:4431-4443 (1985) and Kunkel et al., Proc. Natl. Acad. Sci. USA 82:488 (1985) (1987)). Briefly, in carrying out site-directed mutagenesis of DNA, the starting DNA is altered by first hybridizing an oligonucleotide encoding the desired mutation to a single strand of such starting DNA. After hybridization, a DNA polymerase is used to synthesize an entire second strand, using the hybridized oligonucleotide as a primer, and using the single strand of the starting DNA as a template. Thus, the oligonucleotide encoding the desired mutation is incorporated in the resulting double-stranded DNA.

PCR mutagenesis is also suitable for making amino acid sequence variants of the starting polypeptide, i.e., *H. jecorina* CBH1. See Higuchi, in PCR Protocols, pp. 177-183 (Academic Press, 1990); and Vallette et al., Nuc. Acids Res. 17:723-733 (1989). Briefly, when small amounts of template DNA are used as starting material in a PCR, primers that differ slightly in sequence from the corresponding region in a template DNA can be used to generate relatively large quantities of a specific DNA fragment that differs from the template sequence only at the positions where the primers differ from the template.

Another method for preparing variants, cassette mutagenesis, is based on the technique described by Wells et al., Gene 34:315-323 (1985). The starting material is the plasmid (or other vector) comprising the starting polypeptide DNA to be mutated. The codon(s) in the starting DNA to be mutated are identified. There must be a unique restriction endonuclease site on each side of the identified mutation site(s). If no such restriction sites exist, they may be generated using the above-described oligonucleotide-mediated mutagenesis method to introduce them at appropriate locations in the starting polypeptide DNA. The plasmid DNA is cut at these sites to linearize it. A double-stranded oligonucleotide encoding the sequence of the DNA between the restriction sites but containing the desired mutation(s) is synthesized using standard procedures, wherein the two strands of the oligonucleotide are synthesized separately and then hybridized together using standard techniques. This double-stranded oligonucleotide is referred to as the cassette. This cassette is designed to have 5' and 3' ends that are compatible with the ends of the linearized plasmid, such that it can be directly ligated to the plasmid. This plasmid now contains the mutated DNA sequence.

Alternatively, or additionally, the desired amino acid sequence encoding a desired cellulase can be determined, and a nucleic acid sequence encoding such amino acid sequence variant can be generated synthetically.

The desired cellulase(s) so prepared may be subjected to further modifications, oftentimes depending on the intended use of the cellulase. Such modifications may involve further alteration of the amino acid sequence, fusion to heterologous polypeptide(s) and/or covalent modifications.

V. cbh1 NUCLEIC ACIDS AND CBH1 POLYPEPTIDES

A. Variant cbh-Type Nucleic Acids

After DNA sequences that encode the CBH1 variants have been cloned into DNA constructs, the DNA is used to transform microorganisms. The microorganism to be transformed for the purpose of expressing a variant CBH1 according to the present invention may advantageously comprise a strain derived from *Trichoderma* sp. Thus, a preferred mode for preparing variant CBH1 cellulases according to the present invention comprises transforming a *Trichoderma* sp. host cell with a DNA construct comprising at least a fragment of DNA encoding a portion or all of the variant CBH1. The DNA construct will generally be functionally attached to a promoter. The transformed host cell is then grown under conditions so as to express the desired protein. Subsequently, the desired protein product is purified to substantial homogeneity.

However, it may in fact be that the best expression vehicle for a given DNA encoding a variant CBH1 may differ from *H. jecorina*. Thus, it may be that it will be most advantageous to express a protein in a transformation host that bears phylogenetic similarity to the source organism for the variant CBH1. In an alternative embodiment, *Aspergillus niger* can be used as an expression vehicle. For a description of transformation techniques with *A. niger*, see WO 98/31821, the disclosure of which is incorporated by reference in its entirety.

Accordingly, the present description of a *Trichoderma* spp. expression system is provided for illustrative purposes only and as one option for expressing the variant CBH1 of the invention. One of skill in the art, however, may be inclined to express the DNA encoding variant CBH1 in a different host cell if appropriate and it should be understood that the source of the variant CBH1 should be considered in determining the optimal expression host. Additionally, the skilled worker in the field will be capable of selecting the best expression system for a particular gene through routine techniques utilizing the tools available in the art.

B. Variant CBH1 Polypeptides

The amino acid sequence for the wild type *H. jecorina* CBH1 is shown in FIG. 1. The variant CBH1 polypeptides comprise a substitution or deletion at a position corresponding to one or more of residues L6, S8, P13, Q17, G22, T24, Q27, T41, S47, N49, T59, T66, A68, C71, A77, G88, N89, A100, N103, A112, S113, L125, T160, Y171, Q186, E193, S195, C210, M213, L225, T226, P227, T232, E236, E239, G242, T246, D249, N250, R251, Y252, D257, D259, S278, T281, L288, E295, T296, S297, A299, N301, F311, L318, E325, N327, D329, T332, A336, S341, S342, F352, K354, T356, G359, D368, Y371, N373, T380, Y381, N384, V393, R394, V407, P412, T417, F418 G430, N436, G440, P443, T445, Y466, T478, A481 and/or N490 in CBH1 from *Hypocrea jecorina*.

The variant CBH1's of this invention have amino acid sequences that are derived from the amino acid sequence of a precursor *H. jecorina* CBH1. The amino acid sequence of the CBH1 variant differs from the precursor CBH1 amino acid sequence by the substitution, deletion or insertion of one or more amino acids of the precursor amino acid sequence. The mature amino acid sequence of *H. jecorina* CBH1 is shown in FIG. 1. Thus, this invention is directed to CBH1 variants which contain amino acid residues at positions which are equivalent to the particular identified residue in *H. jecorina* CBH1. A residue (amino acid) of an CBH1 variant is equivalent to a residue of *Hypocrea jecorina* CBH1 if it is either homologous (i.e., corresponding in position in either primary or tertiary structure) or is functionally analogous to a specific residue or portion of that residue in *Hypocrea jecorina* CBH1 (i.e., having the same or similar functional capacity to combine, react, or interact chemically or structurally). As used herein, numbering is intended to correspond to that of the mature CBH1 amino acid sequence as illustrated in FIG. 1. In addition to locations within the precursor CBH1, specific residues in the precursor CBH1 corresponding to the amino acid positions that are responsible for instability when the precursor CBH1 is under thermal stress are identified herein for substitution or deletion. The amino acid position number (e.g., +51) refers to the number assigned to the mature *Hypocrea jecorina* CBH1 sequence presented in FIG. 1.

Alignment of amino acid sequences to determine homology is preferably determined by using a "sequence comparison algorithm." Optimal alignment of sequences for comparison can be conducted, e.g., by the local homology algorithm of Smith & Waterman, *Adv. Appl. Math.* 2:482 (1981), by the homology alignment algorithm of Needleman & Wunsch, *J. Mol. Biol.* 48:443 (1970), by the search for similarity method of Pearson & Lipman, *Proc. Nat'l Acad. Sci. USA* 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), by visual inspection or MOE by Chemical Computing Group, Montreal Canada.

An example of an algorithm that is suitable for determining sequence similarity is the BLAST algorithm, which is described in Altschul, et al., *J. Mol. Biol.* 215:403-410 (1990). Software for performing BLAST analyses is publicly available through the National Center for Biotechnology Information. This algorithm involves first identifying high scoring sequence pairs (HSPs) by identifying short words of length W in the query sequence that either match or satisfy some positive-valued threshold score T when aligned with a word of the same length in a database sequence. These initial neighborhood word hits act as starting points to find longer HSPs containing them. The word hits are expanded in both directions along each of the two sequences being compared for as far as the cumulative alignment score can be increased. Extension of the word hits is stopped when: the cumulative alignment score falls off by the quantity X from a maximum achieved value; the cumulative score goes to zero or below; or the end of either sequence is reached. The BLAST algorithm parameters W, T, and X determine the sensitivity and speed of the alignment. The BLAST program uses as defaults a word length (W) of 11, the BLOSUM62 scoring matrix (see Henikoff & Henikoff, Proc. Natl. Acad. Sci. USA 89:10915-10919, (1992)) alignments (B) of 50, expectation (E) of 10, M'5, N'-4, and a comparison of both strands.

The BLAST algorithm then performs a statistical analysis of the similarity between two sequences (see, e.g., Kadin & Altschul, *Proc. Nat'l. Acad. Sci. USA* 90:5873-5787 (1993)). One measure of similarity provided by the BLAST algorithm is the smallest sum probability (P(N)), which provides an indication of the probability by which a match between two nucleotide or amino acid sequences would occur by chance. For example, an amino acid sequence is considered similar to a protease if the smallest sum probability in a comparison of the test amino acid sequence to a protease amino acid sequence is less than about 0.1, more preferably less than about 0.01, and most preferably less than about 0.001.

Additional specific strategies for modifying stability of CBH1 cellulases are provided below:

(1) Decreasing the entropy of main-chain unfolding may introduce stability to the enzyme. For example, the introduction of proline residues may significantly stabilize the protein by decreasing the entropy of the unfolding (see, e.g., Watanabe, et al., Eur. J. Biochem. 226:277-283 (1994)). Similarly, glycine residues have no β-carbon, and thus have considerably greater backbone conformational freedom than many other residues. Replacement of glycines, preferably with alanines, may reduce the entropy of unfolding and improve stability (see, e.g., Matthews, et al., Proc. Natl. Acad. Sci. USA 84; 6663-6667 (1987)). Additionally, by shortening external loops it may be possible to improve stability. It has been observed that hyperthermophile produced proteins have shorter external loops than their mesophilic homologues (see, e.g., Russell, et al., Current Opinions in Biotechnology 6:370-374 (1995)). The introduction of disulfide bonds may also be effective to stabilize distinct tertiary structures in relation to each other. Thus, the introduction of cysteines at residues accessible to existing cysteines or the introduction of pairs of cysteines that could form disulfide bonds would alter the stability of a CBH1 variant.

(2) Decreasing internal cavities by increasing side-chain hydrophobicity may alter the stability of an enzyme. Reducing the number and volume of internal cavities increases the stability of enzyme by maximizing hydrophobic interactions and reducing packing defects (see, e.g., Matthews, Ann. Rev. Biochem. 62:139-160 (1993); Burley, et al., Science 229:23-29 (1985); Zuber, Biophys. Chem. 29:171-179 (1988); Kellis, et al., Nature 333:784-786 (1988)). It is known that multimeric proteins from thermophiles often have more hydrophobic sub-unit interfaces with greater surface complementarity than their mesophilic counterparts (Russell, et al., supra). This principle is believed to be applicable to domain interfaces of monomeric proteins. Specific substitutions that may improve stability by increasing hydrophobicity include lysine to arginine, serine to alanine and threonine to alanine (Russell, et al., supra). Modification by substitution to alanine or proline may increase side-chain size with resultant reduction in cavities, better packing and increased hydrophobicity. Substitutions to reduce the size of the cavity, increase hydrophobicity and improve the complementarity the interfaces between the domains of CBH1 may improve stability of the enzyme. Specifically, modification of the specific residue at these positions with a different residue selected from any of phenylalanine, tryptophan, tyrosine, leucine and isoleucine may improve performance.

(3) Balancing charge in rigid secondary structure, i.e., α-helices and β-turns may improve stability. For example, neutralizing partial positive charges on a helix N-terminus with negative charge on aspartic acid may improve stability of the structure (see, e.g., Eriksson, et al., *Science* 255:178-183 (1992)). Similarly, neutralizing partial negative charges on helix C-terminus with positive charge may improve stability. Removing positive charge from interacting with peptide N-terminus in β-turns should be effective in conferring tertiary structure stability. Substitution with a non-positively charged residue could remove an unfavorable positive charge from interacting with an amide nitrogen present in a turn.

(4) Introducing salt bridges and hydrogen bonds to stabilize tertiary structures may be effective. For example, ion pair interactions, e.g., between aspartic acid or glutamic acid and lysine, arginine or histidine, may introduce strong stabilizing effects and may be used to attach different tertiary structure elements with a resultant improvement in thermostability. Additionally, increases in the number of charged residue/non-charged residue hydrogen bonds, and the number of hydrogen-bonds generally, may improve thermostability (see, e.g., Tanner, et al., *Biochemistry* 35:2597-2609 (1996)). Substitution with aspartic acid, asparagine, glutamic acid or glutamine may introduce a hydrogen bond with a backbone amide. Substitution with arginine may improve a salt bridge and introduce an H-bond into a backbone carbonyl.

(5) Avoiding thermolabile residues in general may increase thermal stability. For example, asparagine and glutamine are susceptible to deamidation and cysteine is susceptible to oxidation at high temperatures. Reducing the number of these residues in sensitive positions may result in improved thermostability (Russell, et al., supra). Substitution or deletion by any residue other than glutamine or cysteine may increase stability by avoidance of a thermolabile residue.

(6) Stabilization or destabilization of binding of a ligand that confers modified stability to CBH1 variants. For example, a component of the matrix in which the CBH1 variants of this invention are used may bind to a specific surfactant/thermal sensitivity site of the CBH1 variant. By modifying the site through substitution, binding of the component to the variant may be strengthened or diminished. For example, a non-aromatic residue in the binding crevice of CBH1 may be substituted with phenylalanine or tyrosine to introduce aromatic side-chain stabilization where interaction of the cellulose substrate may interact favorably with the benzyl rings, increasing the stability of the CBH1 variant.

(7) Increasing the electronegatvity of any of the surfactant thermal sensitivity ligands may improve stability under surfactant or thermal stress. For example, substitution with phenylalanine or tyrosine may increase the electronegativity of D (aspartate) residues by improving shielding from solvent, thereby improving stability.

C. Homologous CBH1 Nucleic Acids and Polypeptides

Genomic DNA from microbial organisms is fixed to a membrane. The genomic DNA is hybridized with the gene specific probes and screened using PCR. The PCR product(s) are isolated using techniques well known in the art and sequenced.

VI. EXPRESSION OF RECOMBINANT CBH1 HOMOLOGS AND VARIANTS

The methods of the invention rely on the use cells to express a desired cellulase, with no particular method of expression required.

The invention provides host cells that have been transduced, transformed or transfected with an expression vector comprising a desired cellulase-encoding nucleic acid sequence. The culture conditions, such as temperature, pH and the like, are those previously used for the parental host cell prior to transduction, transformation or transfection and will be apparent to those skilled in the art.

In one approach, a filamentous fungal cell or yeast cell is transfected with an expression vector having a promoter or biologically active promoter fragment or one or more (e.g., a series) of enhancers which functions in the host cell line, operably linked to a DNA segment encoding a desired cellulase, such that desired cellulase is expressed in the cell line.

A. Nucleic Acid Constructs/Expression Vectors.

Natural or synthetic polynucleotide fragments encoding a desired cellulase ("desired cellulase-encoding nucleic acid sequences") may be incorporated into heterologous nucleic acid constructs or vectors, capable of introduction into, and replication in, a filamentous fungal or yeast cell. The vectors and methods disclosed herein are suitable for use in host cells for the expression of a desired cellulase. Any vector may be used as long as it is replicable and viable in the cells into which it is introduced. Large numbers of suitable vectors and promoters are known to those of skill in the art, and are commercially available. Cloning and expression vectors are also described in Sambrook et al., 1989, Ausubel F M et al., 1989, and Strathern et al., 1981, each of which is expressly incorporated by reference herein. Appropriate expression vectors for fungi are described in van den Hondel, C. A. M. J. et al. (1991) In: Bennett, J. W. and Lasure, L. L. (eds.) More Gene Manipulations in Fungi. Academic Press, pp. 396428. The appropriate DNA sequence may be inserted into a plasmid or vector (collectively referred to herein as "vectors") by a variety of procedures. In general, the DNA sequence is inserted into an appropriate restriction endonuclease site(s) by standard procedures. Such procedures and related subcloning procedures are deemed to be within the scope of knowledge of those skilled in the art.

Recombinant filamentous fungi comprising the coding sequence for a desired cellulase may be produced by introducing a heterologous nucleic acid construct comprising the desired cellulase coding sequence into the cells of a selected strain of the filamentous fungi.

Once the desired form of a desired cellulase nucleic acid sequence is obtained, it may be modified in a variety of ways. Where the sequence involves non-coding flanking regions, the flanking regions may be subjected to resection, mutagenesis, etc. Thus, transitions, transversions, deletions, and insertions may be performed on the naturally occurring sequence.

A selected desired cellulase coding sequence may be inserted into a suitable vector according to well-known recombinant techniques and used to transform filamentous fungi capable of cellulase expression. Due to the inherent degeneracy of the genetic code, other nucleic acid sequences which encode substantially the same or a functionally equivalent amino acid sequence may be used to clone and express a desired cellulase. Therefore it is appreciated that such substitutions in the coding region fall within the sequence variants covered by the present invention.

The present invention also includes recombinant nucleic acid constructs comprising one or more of the desired cellulase-encoding nucleic acid sequences as described above. The constructs comprise a vector, such as a plasmid or viral vector, into which a sequence of the invention has been inserted, in a forward or reverse orientation.

Heterologous nucleic acid constructs may include the coding sequence for a desired cellulase: (I) in isolation; (ii) in combination with additional coding sequences; such as fusion protein or signal peptide coding sequences, where the desired cellulase coding sequence is the dominant coding sequence; (iii) in combination with non-coding sequences, such as introns and control elements, such as promoter and terminator elements or 5 and/or 3' untranslated regions, effective for expression of the coding sequence in a suitable host; and/or (iv) in a vector or host environment in which the desired cellulase coding sequence is a heterologous gene.

In one aspect of the present invention, a heterologous nucleic acid construct is employed to transfer a desired cellulase-encoding nucleic acid sequence into a cell in vitro, with established filamentous fungal and yeast lines preferred. For long-term, production of a desired cellulase, stable expression is preferred. It follows that any method effective to generate stable transformants may be used in practicing the invention.

Appropriate vectors are typically equipped with a selectable marker-encoding nucleic acid sequence, insertion sites, and suitable control elements, such as promoter and termination sequences. The vector may comprise regulatory sequences, including, for example, non-coding sequences, such as introns and control elements, i.e., promoter and terminator elements or 5' and/or 3' untranslated regions, effective for expression of the coding sequence in host cells (and/or in a vector or host cell environment in which a modified soluble protein antigen coding sequence is not normally expressed), operably linked to the coding sequence. Large numbers of suitable vectors and promoters are known to those of skill in the art, many of which are commercially available and/or are described in Sambrook, et al., (supra).

Exemplary promoters include both constitutive promoters and inducible promoters, examples of which include a CMV promoter, an SV40 early promoter, an RSV promoter, an EF-1α promoter, a promoter containing the tet responsive element (TRE) in the tet-on or tet-off system as described (ClonTech and BASF), the beta actin promoter and the met-allothionine promoter that can upregulated by addition of certain metal salts. A promoter sequence is a DNA sequence which is recognized by the particular filamentous fungus for expression purposes. It is operably linked to DNA sequence encoding a variant CBH1 polypeptide. Such linkage comprises positioning of the promoter with respect to the initiation codon of the DNA sequence encoding the variant CBH1 polypeptide in the disclosed expression vectors. The promoter sequence contains transcription and translation control sequence which mediate the expression of the variant CBH1 polypeptide. Examples include the promoters from the *Aspergillus niger*, *A. awamori* or *A. oryzae* glucoamylase, alpha-amylase, or alpha-glucosidase encoding genes; the *A. nidulans* gpdA or trpC Genes; the *Neurospora crassa* cbh1 or trp1 genes; the *A. niger* or *Rhizomucor miehei* aspartic proteinase encoding genes; the *H. jecorina* cbh1, cbh2, egl1, egl2, or other cellulase encoding genes.

The choice of the proper selectable marker will depend on the host cell, and appropriate markers for different hosts are well known in the art. Typical selectable marker genes include argB from *A. nidulans* or *H. jecorina*, amdS from *A. nidulans*, pyr4 from *Neurospora crassa* or *H. jecorina*, pyrG from *Aspergillus niger* or *A. nidulans*. Additional exemplary selectable markers include, but are not limited to trpc, trp1, oliC31, niaD or leu2, which are included in heterologous nucleic acid constructs used to transform a mutant strain such as trp-, pyr-, leu- and the like.

Such selectable markers confer to transformants the ability to utilize a metabolite that is usually not metabolized by the filamentous fungi. For example, the amdS gene from *H. jecorina* which encodes the enzyme acetamidase that allows transformant cells to grow on acetamide as a nitrogen source. The selectable marker (e.g. pyrG) may restore the ability of an auxotrophic mutant strain to grow on a selective minimal medium or the selectable marker (e.g. olic31) may confer to transformants the ability to grow in the presence of an inhibitory drug or antibiotic.

The selectable marker coding sequence is cloned into any suitable plasmid using methods generally employed in the art. Exemplary plasmids include pUC18, pBR322, pRAX and pUC100. The pRAX plasmid contains AMA1 sequences from *A. nidulans*, which make it possible to replicate in *A. niger*.

The practice of the present invention will employ, unless otherwise indicated, conventional techniques of molecular biology, microbiology, recombinant DNA, and immunology, which are within the skill of the art. Such techniques are explained fully in the literature. See, for example, Sambrook et al., 1989; Freshney, 1987; Ausubel, et al., 1993; and Coligan et al., 1991. All patents, patent applications, articles and publications mentioned herein, are hereby expressly incorporated herein by reference.

B. Host Cells and Culture Conditions for CBH1 Production (i) Filamentous Fungi

Thus, the present invention provides filamentous fungi comprising cells which have been modified, selected and cultured in a manner effective to result in desired cellulase production or expression relative to the corresponding non-transformed parental fungi.

Examples of species of parental filamentous fungi that may be treated and/or modified for desired cellulase expression include, but are not limited to *Trichoderma*, *Penicillium* sp., *Humicola* sp., including *Humicola insolens*; *Aspergillus* sp., including *Aspergillus niger*, *Chrysosporium* sp., *Fusarium* sp., *Hypocrea* sp., and *Emericella* sp.

Cells expressing a desired cellulase are cultured under conditions typically employed to culture the parental fungal line. Generally, cells are cultured in a standard medium containing physiological salts and nutrients, such as described in Pourquie, J. et al., Biochemistry and Genetics of Cellulose Degradation, eds. Aubert, J. P. et al., Academic Press, pp. 71-86, 1988 and Ilmen, M. et al., Appl. Environ. Microbiol. 63:1298-1306, 1997. Culture conditions are also standard, e.g., cultures are incubated at 28° C. in shaker cultures or fermenters until desired levels of desired cellulase expression are achieved.

Preferred culture conditions for a given filamentous fungus may be found in the scientific literature and/or from the source of the fungi such as the American Type Culture Collection (ATCC). After fungal growth has been established, the cells are exposed to conditions effective to cause or permit the expression of a desired cellulase.

In cases where a desired cellulase coding sequence is under the control of an inducible promoter, the inducing agent, e.g., a sugar, metal salt or antibiotics, is added to the medium at a concentration effective to induce desired cellulase expression.

In one embodiment, the strain comprises *Aspergillus niger*, which is a useful strain for obtaining overexpressed protein. For example *A. niger* var *awamori* dgr246 is known to secrete elevated amounts of secreted cellulases (Goedegebuur et al, Curr. Genet (2002) 41: 89-98). Other strains of *Aspergillus niger* var *awamori* such as GCDAP3, GCDAP4 and GAP3-4 are known Ward et al (Ward, M, Wilson, L. J. and Kodama, K. H., 1993, Appl. Microbiol. Biotechnol. 39:738-743).

In another embodiment, the strain comprises *Trichoderma reesei*, which is a useful strain for obtaining overexpressed protein. For example, RL-P37, described by Sheir-Neiss, et al., *Appl. Microbiol. Biotechnol.* 20:46-53 (1984) is known to secrete elevated amounts of cellulase enzymes. Functional equivalents of RL-P37 include *Trichoderma reesei* strain RUT-C30 (ATCC No. 56765) and strain QM9414 (ATCC No. 26921). It is contemplated that these strains would also be useful in overexpressing variant CBH1.

Where it is desired to obtain the desired cellulase in the absence of potentially detrimental native cellulolytic activity, it is useful to obtain a host cell strain which has had one or more cellulase genes deleted prior to introduction of a DNA construct or plasmid containing the DNA fragment encoding the desired cellulase. Such strains may be prepared by the method disclosed in U.S. Pat. No. 5,246,853 and WO 92/06209, which disclosures are hereby incorporated by reference. By expressing a desired cellulase in a host microorganism that is missing one or more cellulase genes, the identification and subsequent purification procedures are simplified.

Gene deletion may be accomplished by inserting a form of the desired gene to be deleted or disrupted into a plasmid by methods known in the art. The deletion plasmid is then cut at an appropriate restriction enzyme site(s), internal to the desired gene coding region, and the gene coding sequence or part thereof replaced with a selectable marker. Flanking DNA sequences from the locus of the gene to be deleted or disrupted, preferably between about 0.5 to 2.0 kb, remain on either side of the selectable marker gene. An appropriate deletion plasmid will generally have unique restriction enzyme sites present therein to enable the fragment containing the deleted gene, including flanking DNA sequences, and the selectable marker gene to be removed as a single linear piece.

A selectable marker must be chosen so as to enable detection of the transformed microorganism. Any selectable marker gene that is expressed in the selected microorganism will be suitable. For example, with *Aspergillus* sp., the selectable marker is chosen so that the presence of the selectable marker in the transformants will not significantly affect the properties thereof. Such a selectable marker may be a gene that encodes an assayable product. For example, a functional copy of a *Aspergillus* sp. gene may be used which if lacking in the host strain results in the host strain displaying an auxotrophic phenotype.

In a preferred embodiment, a pyrG-derivative strain of *Aspergillus* sp. is transformed with a functional pyrG gene, which thus provides a selectable marker for transformation. A pyrG-derivative strain may be obtained by selection of *Aspergillus* sp. strains that are resistant to fluoroorotic acid (FOA). The pyrG gene encodes orotidine-5'-monophosphate decarboxylase, an enzyme required for the biosynthesis of uridine. Strains with an intact pyrG gene grow in a medium lacking uridine but are sensitive to fluoroorotic acid. It is possible to select pyrG-derivative strains that lack a functional orotidine monophosphate decarboxylase enzyme and require uridine for growth by selecting for FOA resistance. Using the FOA selection technique it is also possible to obtain uridine-requiring strains which lack a functional orotate pyrophosphoribosyl transferase. It is possible to transform these cells with a functional copy of the gene encoding this enzyme (Berges & Barreau, *Curr. Genet.* 19:359-365 (1991), and van Hartingsveldt et al., (1987) Development of a homologous transformation system for *Aspergillus niger* based on the pyrG gene. Mol. Gen. Genet. 206:71-75). Selection of derivative strains is easily performed using the FOA resistance technique referred to above, and thus, the pyrG gene is preferably employed as a selectable marker.

To transform pyrG$^-$ *Aspergillus* sp. so as to be lacking in the ability to express one or more cellulase genes, a single DNA fragment comprising a disrupted or deleted cellulase gene is then isolated from the deletion plasmid and used to transform an appropriate pyr$^-$ *Aspergillus* host. Transformants are then identified and selected based on their ability to express the pyrG gene product and thus compliment the uridine auxotrophy of the host strain. Southern blot analysis is then carried out on the resultant transformants to identify and confirm a double crossover integration event that replaces part or all of the coding region of the genomic copy of the gene to be deleted with the pyr4 selectable markers.

Although the specific plasmid vectors described above relate to preparation of pyr$^-$ transformants, the present invention is not limited to these vectors. Various genes can be deleted and replaced in the *Aspergillus* sp. strain using the above techniques. In addition, any available selectable markers can be used, as discussed above. In fact, any *Aspergillus* sp. gene that has been cloned, and thus identified, can be deleted from the genome using the above-described strategy.

As stated above, the host strains used are derivatives of *Aspergillus* sp. that lack or have a nonfunctional gene or genes corresponding to the selectable marker chosen. For example, if the selectable marker of pyrG is chosen, then a specific pyrG$^-$ derivative strain is used as a recipient in the transformation procedure. Similarly, selectable markers comprising *Aspergillus* sp. genes equivalent to the *Aspergillus nidulans* genes amdS, argB, trpC, niaD may be used. The corresponding recipient strain must therefore be a derivative strain such as argB$^-$, trpC$^-$, niaD$^-$, respectively.

DNA encoding the desired cellulase is then prepared for insertion into an appropriate microorganism. According to the present invention, DNA encoding a desired cellulase comprises the DNA necessary to encode for a protein that has functional cellulolytic activity. The DNA fragment encoding the desired cellulase may be functionally attached to a fungal promoter sequence, for example, the promoter of the glaA gene.

It is also contemplated that more than one copy of DNA encoding a desired cellulase may be recombined into the strain to facilitate overexpression. The DNA encoding the desired cellulase may be prepared by the construction of an expression vector carrying the DNA encoding the cellulase. The expression vector carrying the inserted DNA fragment encoding the desired cellulase may be any vector which is capable of replicating autonomously in a given host organism or of integrating into the DNA of the host, typically a plasmid. In preferred embodiments two types of expression vectors for obtaining expression of genes are contemplated. The first contains DNA sequences in which the promoter, gene-coding region, and terminator sequence all originate from the gene to be expressed. Gene truncation may be obtained where desired by deleting undesired DNA sequences (e.g., coding for unwanted domains) to leave the domain to be expressed under control of its own transcriptional and translational regulatory sequences. A selectable marker is also contained on the vector allowing the selection for integration into the host of multiple copies of the novel gene sequences.

The second type of expression vector is preassembled and contains sequences required for high-level transcription and a selectable marker. It is contemplated that the coding region for a gene or part thereof can be inserted into this general-purpose expression vector such that it is under the transcriptional control of the expression cassettes promoter and terminator sequences. For example, pRAX is such a general-purpose expression vector. Genes or part thereof can be inserted downstream of the strong gleA promoter.

In the vector, the DNA sequence encoding the desired cellulase of the present invention should be operably linked to transcriptional and translational sequences, i.e., a suitable promoter sequence and signal sequence in reading frame to the structural gene. The promoter may be any DNA sequence that shows transcriptional activity in the host cell and may be derived from genes encoding proteins either homologous or heterologous to the host cell. An optional signal peptide provides for extracellular production of the desired cellulase. The DNA encoding the signal sequence is preferably that which is naturally associated with the gene to be expressed, however the signal sequence from any suitable source is contemplated in the present invention.

The procedures used to fuse the DNA sequences coding for the desired cellulase of the present invention with the promoter into suitable vectors are well known in the art.

The DNA vector or construct described above may be introduced in the host cell in accordance with known techniques such as transformation, transfection, microinjection, microporation, biolistic bombardment and the like.

The preferred method in the present invention to prepare *Aspergillus* sp. for transformation involves the preparation of protoplasts from fungal mycelium. See Campbell et al., Improved transformation efficiency of *A. niger* using homologous niaD gene for nitrate reductase. Curr. Genet. 16:53-56; 1989. The mycelium can be obtained from germinated vegetative spores. The mycelium is treated with an enzyme that digests the cell wall resulting in protoplasts. The protoplasts are then protected by the presence of an osmotic stabilizer in the suspending medium. These stabilizers include sorbitol, mannitol, potassium chloride, magnesium sulfate and the like. Usually the concentration of these stabilizers varies between 0.8 M and 1.2 M. It is preferable to use about a 1.2 M solution of sorbitol in the suspension medium.

Uptake of the DNA into the host *Aspergilius* sp. strain is dependent upon the calcium ion concentration. Generally between about 10 mM $CaCl_2$ and 50 mM $CaCl_2$ is used in an uptake solution. Besides the need for the calcium ion in the uptake solution, other items generally included are a buffering system such as TE buffer (10 Mm Tris, pH 7.4; 1 mM EDTA) or 10 mM MOPS, pH 6.0 buffer (morpholinepropanesuionic acid) and polyethylene glycol (PEG). It is believed that the polyethylene glycol acts to fuse the cell membranes thus permitting the contents of the medium to be delivered into the cytoplasm of the *Aspergillus* sp. strain and the plasmid DNA is transferred to the nucleus. This fusion frequently leaves multiple copies of the plasmid DNA tenderly integrated into the host chromosome.

Usually a suspension containing the *Aspergillus* sp. protoplasts or cells that have been subjected to a permeability treatment at a density of $10^5$ to $10^6$/mL, preferably $2 \times 10^5$/mL are used in transformation. A volume of 100 μL of these protoplasts or cells in an appropriate solution (e.g., 1.2 M sorbitol; 50 mM $CaCl_2$) are mixed with the desired DNA. Generally a high concentration of PEG is added to the uptake solution. From 0.1 to 1 volume of 25% PEG 4000 can be added to the protoplast suspension. However, it is preferable to add about 0.25 volumes to the protoplast suspension. Additives such as dimethyl sulfoxide, heparin, spermidine, potassium chloride and the like may also be added to the uptake solution and aid in transformation.

Generally, the mixture is then incubated at approximately 0° C. for a period of between 10 to 30 minutes. Additional PEG is then added to the mixture to further enhance the uptake of the desired gene or DNA sequence. The 25% PEG 4000 is generally added in volumes of 5 to 15 times the volume of the transformation mixture; however, greater and lesser volumes may be suitable. The 25% PEG 4000 is preferably about 10 times the volume of the transformation mixture. After the PEG is added, the transformation mixture is then incubated either at room temperature or on ice before the addition of a sorbitol and $CaCl_2$ solution. The protoplast suspension is then further added to molten aliquots of a growth medium. This growth medium permits the growth of transformants only. Any growth medium can be used in the present invention that is suitable to grow the desired transformants. However, if Pyr+ transformants are being selected it is preferable to use a growth medium that contains no uridine. The subsequent colonies are transferred and purified on a growth medium depleted of uridine.

At this stage, stable transformants may be distinguished from unstable transformants by their faster growth rate and the formation of circular colonies with a smooth, rather than ragged outline on solid culture medium lacking uridine. Additionally, in some cases a further test of stability may made by growing the transformants on solid non-selective medium (i.e. containing uridine), harvesting spores from this culture medium and determining the percentage of these spores which will subsequently germinate and grow on selective medium lacking uridine.

In a particular embodiment of the above method, the desired cellulase(s) are recovered in active form from the host cell after growth in liquid media either as a result of the appropriate post translational processing of the desired cellulase.

(ii) Yeast

The present invention also contemplates the use of yeast as a host cell for desired cellulase production. Several other genes encoding hydrolytic enzymes have been expressed in various strains of the yeast *S. cerevisiae*. These include sequences encoding for two endoglucanases (Penttila et al., 1987), two cellobiohydrolases (Penttila et al., 1988) and one beta-glucosidase from *Trichoderma reesei* (Cummings and Fowler, 1996), a xylanase from *Aureobasidlium pullulans* (Li and Ljungdahl, 1996), an alpha-amylase from wheat (Rothstein et al., 1987), etc. In addition, a cellulase gene cassette encoding the *Butyrivibrio fibrisolvens* endo-[beta]-1,4-glucanase (END1), *Phanerochaete chrysospodium* cellobiohydrolase (CBH1), the *Ruminococcus flavefaciens* cellodextrinase (CEL1) and the *Endomyces fibrilizer* cellobiase (Bgl1) was successfully expressed in a laboratory strain of *S. cerevisiae* (Van Rensburg et al., 1998).

C. Introduction of a Desired Cellulase-Encoding Nucleic Acid Sequence into Host Cells.

The invention further provides cells and cell compositions which have been genetically modified to comprise an exogenously provided desired cellulase-encoding nucleic acid sequence. A parental cell or cell line may be genetically modified (i.e., transduced, transformed or transfected) with a cloning vector or an expression vector. The vector may be, for example, in the form of a plasmid, a viral particle, a phage, etc, as further described above.

The methods of transformation of the present invention may result in the stable integration of all or part of the transformation vector into the genome of the filamentous fungus. However, transformation resulting in the maintenance of a self-replicating extra-chromosomal transformation vector is also contemplated.

Many standard transfection methods can be used to produce *Trichoderma reesei* cell lines that express large quantities of the heterologus protein. Some of the published methods for the introduction of DNA constructs into cellulase-producing strains of *Trichoderma* include Lorito, Hayes, DiPietro and Harman, 1993, Curr. Genet. 24: 349-356; Goldman, VanMontagu and Herrera-Estrella, 1990, Curr. Genet. 17:169-174; Penttila, Nevalainen, Ratto, Salminen and Knowles, 1987, Gene 61: 155-164, for Aspergillus Yelton, Hamer and Timberlake, 1984, Proc. Natl. Acad. Sci. USA 81: 1470-1474, for Fusarium Bajar, Podila and Kolattukudy, 1991, Proc. Natl. Acad. Sci. USA 88: 8202-8212, for Streptomyces Hopwood et al., 1986, The John Innes Foundation, Norwich, UK and for Bacillus, Brigidi, DeRossi, Bertarini, Riccardi and Matteuzzi, 1990, FEMS Microbiol. Lett. 67: 135-138, 1990.

Any of the well-known procedures for introducing foreign nucleotide sequences into host cells may be used. These include the use of calcium phosphate transfection, polybrene, protoplast fusion, electroporation, biolistics, liposomes, microinjection, plasma vectors, viral vectors and any of the other well known methods for introducing cloned genomic DNA, cDNA, synthetic DNA or other foreign genetic material into a host cell (see, e.g., Sambrook et al., supra). Also of use is the *Agrobacterium*-mediated transfection method described in U.S. Pat. No. 6,255,115. It is only necessary that the particular genetic engineering procedure used be capable of successfully introducing at least one gene into the host cell capable of expressing the heterologous gene.

In addition, heterologous nucleic acid constructs comprising a desired cellulase-encoding nucleic acid sequence can be transcribed in vitro, and the resulting RNA introduced into the host cell by well-known methods, e.g., by injection.

The invention further includes novel and useful transformants of filamentous fungi such as *H. jecorina* and *A. niger* for use in producing fungal cellulase compositions. The invention includes transformants of filamentous fungi especially fungi comprising the desired cellulase coding sequence, or deletion of the endogenous cbh coding sequence.

VII. ANALYSIS FOR CBH1 NUCLEIC ACID CODING SEQUENCES AND/OR PROTEIN EXPRESSION

In order to evaluate the expression of a desired cellulase by a cell line that has been transformed with a desired cellulase-encoding nucleic acid construct, assays can be carried out at the protein level, the RNA level or by use of functional bioassays particular to cellobiohydrolase activity and/or production.

In one exemplary application of the desired cellulase nucleic acid and protein sequences described herein, a genetically modified strain of filamentous fungi, e.g., *Trichoderma reesei*, is engineered to produce an increased amount of a desired cellulase. Such genetically modified filamentous fungi would be useful to produce a cellulase product with greater increased cellulolytic capacity. In one approach, this is accomplished by introducing the coding sequence for a desired cellulase into a suitable host, e.g., a filamentous fungi such as *Aspergillus niger.*

Accordingly, the invention includes methods for expressing a desired cellulase in a filamentous fungus or other suitable host by introducing an expression vector containing the DNA sequence encoding a desired cellulase into cells of the filamentous fungus or other suitable host.

In another aspect, the invention includes methods for modifying the expression of a desired cellulase in a filamentous fungus or other suitable host. Such modification includes a decrease or elimination in expression of the endogenous CBH.

In general, assays employed to analyze the expression of a desired cellulase include, Northern blotting, dot blotting (DNA or RNA analysis), RT-PCR (reverse transcriptase polymerase chain reaction), or in situ hybridization, using an appropriately labeled probe (based on the nucleic acid coding sequence) and conventional Southern blotting and autoradiography.

In addition, the production and/or expression of a desired cellulase may be measured in a sample directly, for example, by assays for cellobiohydrolase activity, expression and/or production. Such assays are described, for example, in Becker et al., Biochem J. (2001) 356:19-30 and Mitsuishi et al., FEBS (1990) 275:135-138, each of which is expressly incorporated by reference herein. The ability of CBH1 to hydrolyze isolated soluble and insoluble substrates can be measured using assays described in Srisodsuk et al., J. Biotech. (1997) 57:4957 and Nidetzky and Claeyssens Biotech. Bioeng. (1994) 44:961-966. Substrates useful for assaying cellobiohydrolase, endoglucanase or β-glucosidase activities include crystalline cellulose, filter paper, phosphoric acid swollen cellulose, cellooligosaccharides, methylumbelliferyl lactoside, methylumbelliferyl cellobioside, orthonitrophenyl lactoside, paranitrophenyl lactoside, orthonitrophenyl cellobioside, paranitrophenyl cellobioside.

In addition, protein expression, may be evaluated by immunological methods, such as immunohistochemical staining of cells, tissue sections or immunoassay of tissue culture medium, e.g., by Western blot or ELISA. Such immunoassays can be used to qualitatively and quantitatively evaluate expression of a desired cellulase. The details of such methods are known to those of skill in the art and many reagents for practicing such methods are commercially available.

A purified form of a desired cellulase may be used to produce either monoclonal or polyclonal antibodies specific to the expressed protein for use in various immunoassays. (See, e.g., Hu et al., 1991). Exemplary assays include ELISA, competitive immunoassays, radioimmunoassays, Western blot, indirect immunofluorescent assays and the like. In general, commercially available antibodies and/or kits may be used for the quantitative immunoassay of the expression level of cellobiohydrolase proteins.

VIII. ISOLATION AND PURIFICATION OF RECOMBINANT CBH1 PROTEIN

In general, a desired cellulase protein produced in cell culture is secreted into the medium and may be purified or isolated, e.g., by removing unwanted components from the cell culture medium. However, in some cases, a desired cellulase protein may be produced in a cellular form necessitating recovery from a cell lysate. In such cases the desired cellulase protein is purified from the cells in which it was produced using techniques routinely employed by those of skill in the art. Examples include, but are not limited to, affinity chromatography (Van Tilbeurgh et al., 1984), ion-exchange chromatographic methods (Goyal et al., 1991; Fliess et al., 1983; Bhikhabhai et al., 1984; Ellouz et al., 1987), including ion-exchange using materials with high resolution power (Medve et al., 1998), hydrophobic interaction chromatography (Tomaz and Queiroz, 1999), and two-phase partitioning (Brumbauer, et al., 1999).

Typically, the desired cellulase protein is fractionated to segregate proteins having selected properties, such as binding affinity to particular binding agents, e.g., antibodies or receptors; or which have a selected molecular weight range, or range of isoelectric points.

Once expression of a given desired cellulase protein is achieved, the desired cellulase protein thereby produced is purified from the cells or cell culture. Exemplary procedures suitable for such purification include the following: antibody-affinity column chromatography, ion exchange chromatography; ethanol precipitation; reverse phase HPLC; chromatography on silica or on a cation-exchange resin such as DEAE; chromatofocusing; SDS-PAGE; ammonium sulfate precipitation; and gel filtration using, e.g., Sephadex G-75. Various methods of protein purification may be employed and such methods are known in the art and described e.g. in Deutscher, 1990; Scopes, 1982. The purification step(s) selected will depend, e.g., on the nature of the production process used and the particular protein produced.

IX. UTILITY OF cbh1 And CBH1

It can be appreciated that the desired cellulase nucleic acids, the desired cellulase protein and compositions comprising desired cellulase protein activity find utility in a wide variety applications, some of which are described below.

New and improved cellulase compositions that comprise varying amounts of a desired cellulase find utility in detergent compositions that exhibit enhanced cleaning ability, function as a softening agent and/or improve the feel of cotton fabrics (e.g., "stone washing" or "biopolishing"), in compositions for degrading wood pulp into sugars (e.g., for bio-ethanol production), and/or in feed compositions. The isolation and characterization of cellulase of each type provides the ability to control the aspects of such compositions.

Desired cellulases with decreased thermostability find uses, for example, in areas where the enzyme activity is required to be neutralized at lower temperatures so that other enzymes that may be present are left unaffected. In addition, the enzymes may find utility in the limited conversion of cellulosics, for example, in controlling the degree of crystallinity or of cellulosic chain-length. After reaching the desired extent of conversion the saccharifying temperature can be raised above the survival temperature of the de-stabilized CBH1. As the CBH1 activity is essential for hydrolysis of crystalline cellulose, conversion of crystalline cellulose will cease at the elevated temperature.

In one approach, the cellulase of the invention finds utility in detergent compositions or in the treatment of fabrics to improve the feel and appearance.

Since the rate of hydrolysis of cellulosic products may be increased by using a transformant having at least one additional copy of the desired cellulase gene, either as a replicative plasmid or inserted into the genome, products that contain cellulose or heteroglycans can be degraded at a faster rate and to a greater extent. Products made from cellulose such as paper, cotton, cellulosic diapers and the like can be degraded more efficiently in a landfill. Thus, the fermentation product obtainable from the transformants or the transformants alone may be used in compositions to help degrade by liquefaction a variety of cellulose products that add to the overcrowded landfills.

Separate saccharification and fermentation is a process whereby cellulose present in biomass, e.g., corn stover, is converted to glucose and subsequently yeast strains convert glucose into ethanol. Simultaneous saccharification and fermentation is a process whereby cellulose present in biomass, e.g., corn stover, is converted to glucose and, at the same time and in the same reactor, yeast strains convert glucose into ethanol. Thus, in another approach, the desired cellulase of the invention finds utility in the degradation of biomass to ethanol. Ethanol production from readily available sources of cellulose provides a stable, renewable fuel source.

Cellulose-based feedstocks are comprised of agricultural wastes, grasses and woods and other low-value biomass such as municipal waste (e.g., recycled paper, yard clippings, etc.). Ethanol may be produced from the fermentation of any of these cellulosic feedstocks. However, the cellulose must first be converted to sugars before there can be conversion to ethanol.

A large variety of feedstocks may be used with the inventive desired cellulase(s) and the one selected for use may depend on the region where the conversion is being done. For example, in the Midwestern United States agricultural wastes such as wheat straw, corn stover and bagasse may predominate while in California rice straw may predominate. However, it should be understood that any available cellulosic biomass may be used in any region.

A cellulase composition containing an enhanced amount of cellobiohydrolase finds utility in ethanol production. Ethanol from this process can be further used as an octane enhancer or directly as a fuel in lieu of gasoline which is advantageous because ethanol as a fuel source is more environmentally friendly than petroleum derived products. It is known that the use of ethanol will improve air quality and possibly reduce local ozone levels and smog. Moreover, utilization of ethanol in lieu of gasoline can be of strategic importance in buffering the impact of sudden shifts in non-renewable energy and petro-chemical supplies.

Ethanol can be produced via saccharification and fermentation processes from cellulosic biomass such as trees, herbaceous plants, municipal solid waste and agricultural and forestry residues. However, the ratio of individual cellulase enzymes within a naturally occurring cellulase mixture produced by a microbe may not be the most efficient for rapid conversion of cellulose in biomass to glucose. It is known that endoglucanases act to produce new cellulose chain ends which themselves are substrates for the action of cellobiohydrolases and thereby improve the efficiency of hydrolysis of the entire cellulase system. Therefore, the use of increased or optimized cellobiohydrolase activity may greatly enhance the production of ethanol.

Thus, the inventive cellobiohydrolase(s) finds use in the hydrolysis of cellulose to its sugar components. In one embodiment, a desired cellulase is added to the biomass prior to the addition of a fermentative organism. In a second embodiment, a desired cellulase is added to the biomass at the same time as a fermentative organism. Optionally, there may be other cellulase components present in either embodiment.

In another embodiment the cellulosic feedstock may be pretreated. Pretreatment may be by elevated temperature and the addition of either of dilute acid, concentrated acid or dilute alkali solution. The pretreatment solution is added for a time sufficient to at least partially hydrolyze the hemicellulose components and then neutralized.

The detergent compositions of this invention may employ besides the cellulase composition (irrespective of the cellobiohydrolase content, i.e., cellobiohydrolase-free, substantially cellobiohydrolase-free, or cellobiohydrolase enhanced), a surfactant, including anionic, non-ionic and ampholytic surfactants, a hydrolase, building agents, bleaching agents, bluing agents and fluorescent dyes, caking inhibitors, solubilizers, cationic surfactants and the like. All of these components are known in the detergent art. The cellulase composition as described above can be added to the detergent composition either in a liquid diluent, in granules, in emulsions, in gels, in pastes, and the like. Such forms are well known to the skilled artisan. When a solid detergent composition is employed, the cellulase composition is preferably formulated as granules. Preferably, the granules can be formulated so as to contain a cellulase protecting agent. For a more thorough discussion, see U.S. Pat. No. 6,162,782 entitled "Detergent compositions containing cellulase compositions deficient in CBH1 type components," which is incorporated herein by reference.

Preferably the cellulase compositions are employed from about 0.00005 weight percent to about 5 weight percent relative to the total detergent composition. More preferably, the cellulase compositions are employed from about 0.0002 weight percent to about 2 weight percent relative to the total detergent composition.

In addition the desired cellulase nucleic acid sequence finds utility in the identification and characterization of related nucleic acid sequences. A number of techniques useful for determining (predicting or confirming) the function of related genes or gene products include, but are not limited to, (A) DNA/RNA analysis, such as (1) overexpression, ectopic expression, and expression in other species; (2) gene knock-out (reverse genetics, targeted knock-out, viral induced gene silencing (VIGS, see Baulcombe, 1999); (3) analysis of the methylation status of the gene, especially flanking regulatory regions; and (4) in situ hybridization; (B) gene product analysis such as (1) recombinant protein expression; (2) antisera production, (3) immunolocalization; (4) biochemical assays for catalytic or other activity; (5) phosphorylation status; and (6) interaction with other proteins via yeast two-hybrid analysis; (C) pathway analysis, such as placing a gene or gene product within a particular biochemical or signaling pathway based on its overexpression phenotype or by sequence homology with related genes; and (D) other analyses which may also be performed to determine or confirm the participation of the isolated gene and its product in a particular metabolic or signaling pathway, and help determine gene function.

EXAMPLES

The present invention is described in further detain in the following examples which are not in any way intended to limit the scope of the invention as claimed. The attached Figures are meant to be considered as integral parts of the specification and description of the invention. All references cited are herein specifically incorporated by reference for all that is described therein.

Example 1

Identification of CBH1 Homologs

This example illustrates the novel CBH1 homologs found in a variety of fungi. Genomic DNA was prepared for several different microorganisms for the purpose of undertaking a PCR reaction to determine whether homologous CBH1 cellulases are encoded by the DNA of a particular organism.
Isolation of Genomic DNA Genomic DNA may be isolated using any method known in the art. In this set of experiments we received 48 genomic DNA solutions from diverse *Hypocrea* and *Trichoderma* species from collaboration with the Technical University of Vienna (TUV), *Hypocrea schweinitzii* (CBS 243.63), *Hypocrea orientalis* (PPR13894), *Trichoderma pseudokoningii* (CBS 408.91) and *Trichoderma konilangbra* (isolate 1). However, the following protocol may be used:

Cells are grown at 30° C. in 20 ml Potato Dextrose Broth (PDB) for 24 hours. The cells are diluted 1:20 in fresh PDB medium and grown overnight. Two milliliters of cells are centrifuged and the pellet washed in 1 ml KC (60 g KCl, 2 g citric acid per liter, pH adjusted to 6.2 with 1 M KOH). The cell pellet is resuspended in 900 µl KC. 100 µl (20 mg/ml) Novozyme® is added, mixed gently and the protoplastation followed microscopically at 37° C. until greater than 95% protoplasts are formed for a maximum of 2 hours. The cells are centrifuged at 1500 rpm (460 g) for 10 minutes. 200 µl TES/SDS (10 mM Tris, 50 mM EDTA, 150 mM NaCl, 1% SDS) is added, mixed and incubated at room temperature for 5 minutes. DNA is isolated using a Qiagen mini-prep isolation kit (Qiagen). The column is eluted with 100 µl milli-Q water and the DNA collected.

An alternative method using the FastPrep® method may be desirable. The system consists of the FastPrep® Instrument as well as FastPrep® kits for nucleic acid isolation. FastPrep® is available from Obiogene.
Construction of Primers PCR was performed on a standard PCR machine such as the PCT-200 Peltier Thermal Cycler from MJ Research Inc. under the following conditions:

1) 1 minute at 96° C. for 1 cycle
2) 30 seconds at 94° C.
  90 seconds at 45° C. (+1° C. per cycle)
  2 minutes at 72° C.
3) Repeat step 2 for 10 cycles
4) 30 seconds at 94° C.
  90 seconds at 55° C.
  2 minutes at 72° C.
5) Repeat step 4 for 20 cycles
6) 7 minutes at 72° C. for 1 cycle, and
7) lower temperature to 15° C. for storage and further analysis.

The following DNA primers were constructed for use in amplification of homologous CBH1 genes from genomic DNA's isolated from various microorganisms. All symbols used herein for protein and DNA sequences correspond to IUPAC IUB Biochemical Nomenclature Commission codes.

Homologous 5' (FRG192) and 3' (FRG193) primers were developed based on the sequence of CBH1 from *Trichoderma reesei*. Both primers contained Gateway cloning sequences from Invitrogen® at the 5' of the primer. Primer FRG192 contained attB1 sequence and primer FRG193 contained attB2 sequence.

Sequence of FRG192 without the attB1:
ATGTATCGGAAGTTGGCCG (signal sequence of CBH1 *H. jecorina*)

Sequence of FRG193 without the attB2:
TTACAGGCACTGAGAGTAG (cellulose binding module of CBH1 *H. jecorina*)

PCR conditions were as follows: 10 µL of 10× reaction buffer (10× reaction buffer comprising 100 mM Tris HCl, pH 8-8.5; 250 mM KCl; 50 mM (NH$_4$)SO$_4$; 20 mM MgSO$_4$); 0.2 mM each of dATP, dTTP, dGTP, dCTP (final concentration), 1 µL of 100 ng/µL genomic DNA, 0.5 µL of PWO polymerase (Boehringer Mannheim, Cat # 1644-947) at 1 unit per µL, 0.2 µM of each primer, FRG192 and FRG193, (final concentration), 4 µl DMSO and water to 100 µL.

These conditions finally resulted in 4 genes from different species:
  1. *Hypocrea schweinitzii* (CBS 243.63)
  2. *Hypocrea orientalis* (PPR13894)
  3. *Trichoderma pseudokoningii* (CBS 408.91)
  4. *Trichoderma konilangbra*
Isolation of Cel7A Gene Sequences The full length sequences were obtained directly by using the N terminal (FRG192) and C terminal (FRG193) primers. The full length DNA sequences were translated into three open reading frames using Vector NTI software. Comparison of DNA and protein sequences to *H. jecorina* Cel7A were performed to identify the putative intron sequences. Translation of the genomic DNA sequence without the intron sequences revealed the protein sequence of homologous CBH1's. Full length genes have been obtained and are provided in FIGS. 3, 5, 7 and 9.

Example 2

Expression and Thermostability of CBH1 Homologs

The full-length genes from Example 1 were transferred to the *A. niger* Gateway compatible destination vector, which was developed by Genencor. This vector was built by using the pRAX1 as a backbone, shown in FIG. 11, according to the manual given in Gateway™ Cloning Technology: version 1 page 34-38.

The newly developed expression vector is shown in FIG. 12; this is a product of transferring the new genes into the destination vector pRAXdes2. This resulted in the final expression vectors called pRAXdesCBH1(specified with the species name)

The constructs has been transformed into *A. niger* var. *awamori* according to the method described by Cao et al (Cao Q-N, Stubbs M, Ngo K Q P, Ward M, Cunningham A, Pai E F, Tu G-C and Hofmann T (2000) Penicillopepsin-JT2 a recombinant enzyme from *Penicillium janthinellum* and contribution of a hydrogen bond in subsite S3 to kcat *Protein Science* 9:991-1001).

Transformants were streaked on minimal medium plates (Ballance D J, Buxton F P, and Turner G (1983) Transformation of *Aspergillus nidulans* by the orotidine-5'-phosphate decarboxylase gene of *Neurospora crassa* Biochem Biophys Res Commun 112:284-289) and grown for 4 days at 30° C. Spores were collected using methods well known in the art. *A. nidulans* conidia are harvested in water (by rubbing the surface of a conidiating culture with a sterile bent glass rod to dislodge the spores) and can be stored for weeks to months at 4° C. without a serious loss of viability. However, freshly harvested spores germinate more reproducibly. For long-term storage, spores can be stored in 50% glycerol at −20° C., or in 15-20% glycerol at −80° C. Glycerol is more easily pipetted as an 80% solution in water. 800 μl of aqueous conidial suspension (as made for 4° C. storage) added to 200 μl 80% glycerol is used for a −80° C. stock; 400 μl suspension added to 600 μl 80% glycerol is used for a −20° C. stock. Vortex before freezing. For mutant collections, small pieces of conidiating cultures can be excised and placed in 20% glycerol, vortexed, and frozen as −80° C. stocks. In our case we store them in 50% glycerol at −80° C.

*A. niger* var *awamori* transformants were grown on minimal medium lacking uridine (Ballance et al. 1983). Transformants were screened for cellulase activity by inoculating 1 cm² of spore suspension from the sporulated grown agar plate into 100 ml shake flasks for 3 days at 37° C. as described by Cao et al. (2000).

The CBH1 activity assay is based on the hydrolysis of the nonfluorescent 4-methylumbelliferyl-β-lactoside to the products lactose and 7-hydroxy-4-methylcoumarin, the latter product is responsible for the fluorescent signal. Pipette 170 μl 50 mM NaAc buffer pH 4.5 in a 96-well microtiter plate (MTP) (Greiner, Fluotrac 200, art. nr. 655076) suitable for fluorescence. Add 10 μl of supernatant and then add 10 μl of MUL (1 mM 4-methylumbelliferyl-β-lactoside (MUL) in milliQ water) and put the MTP in the Fluostar Galaxy (BMG Labtechnologies; D-77656 Offenburg). Measure the kinetics for 16 min. (8 cycles of 120 s each) using $\lambda_{320\ nm}$ (excitation) and $\lambda_{460\ nm}$ (emission) at 50° C. Supernatents having CBH activity were then subjected to Hydrophobic Interaction Chromatography as described in Example 5 below.

The amino acid sequences were deduced as stated above in Example 1. The amino acid sequences for the CBH1 homologs are shown in FIGS. 4 (*Hypocrea orientalis*), 6 (*Hypocrea schweinitzii*), 8 (*Trichoderma konilangbra*) and 10 (*Trichoderma pseudokoningii*).

Thermostability of the homologs was determined as described in Example 5 below.

TABLE 1

Tm measurements and comparison between the different CBH1 homologous sequences.

| CBH1 homolog | % identity | Tm | ΔTm |
|---|---|---|---|
| *Hypocrea jecorina* | | 62.5 | |
| *Hypocrea schweinitzii* (CBS 243.63) | 96.5 | 61.4 | −1.1 |
| *Hypocrea orientalis* (PPRI 3894) | 97.1 | 62.8 | 0.3 |
| *Trichoderma pseudokoningii* (CBS 408.91) | 94.9 | 57.5 | −5.0 |
| *Trichoderma konilangbra* | 93.0 | 59.4 | −3.1 |

As can be seen, the CBH I cellulase homologs had a slight or negative effect on the thermal stability of the variant CBH I cellulases compared to wild type. The homologs are closely related to *H. jecorina* CBH1; the thermal stability differences between *H. jecorina* and the homologs may indicate that sites with amino acid residues different from those found in *H. jecorina* CBH1 may be involved in thermostability.

Example 3

Identification of Sites Important for Stability

The amino acid sequences of the CBH1 homologs characterized in Example 2, above, were aligned with the *H. jecorina* sequence with Vector NTI using the Clustal W algorithm with (Nucleic Acid Research, 22 (22): 4673-4680, 1994). The alignment is shown in FIG. 2.

Possible sites involved in the stability of the CBH1 enzyme were determined three different ways based on alignment of the sequences of the homologs with CBH1. In the first method, sites that differed between the *H. jecorina* CBH1 catalytic domain and the catalytic domain of at least one of the homologs of lower stability (i.e., excluding only *H. orientalis*) were identified as possible sites involved in the thermostability of CBH1. The sites identified were L6, P13, T24, Q27, S47, T59, T66, G88, N89, T160, Q186, S195, T232, E236, E239, G242, D249, N250, T281, E295, F311, E325, N327, D329, T332, A336, K354, V407, P412, T417 and/or F418 in CBH1 from *Hypocrea jecorina*.

In the second method, sites where the residue in *H. jecoina* OR *H. orientalis* is the same as that found in all of the decreased stability enzyme homologs resulted in the identification of sites that lacked correlation with Tm. The sites identified as retaining relevance with stability were L6, T24, Q27, S47, T59, T66, T160, Q186, S195, T232, E236, G242, D249, T281, E295, E325, N327, D329, T332, K354, and/or P412 in CBH1 from *Hypocrea jecorina*.

In the final method, sites where *H. jecorina* AND *H. orientalis* are the same, with the corresponding residue in *H. schweinitzii* being either the same or different as in either of these two, but a different amino acid in the corresponding site of either *T. konilangbra* or *T. pseudokoningii* were considered as possible sites involved in thermostability of the enzyme. These sites, which empirically showed the best correlation with Tm stability, were identified as Q186, S195, E325, T332 and P412.

Identification of the sites with amino acid residues different from those found in *H. jecorina* CBH1 were therefore subjected to site saturated mutagenesis.

Example 4

Expression of CBH1 Variants

The PCR fragments were obtained using the primers and protocols described in Example 1. The fragments were purified from an agarose gel using the Qiagen Gel extraction KIT. The purified fragments were used to perform a clonase reaction with the pDONR™201 vector from Invitrogen® using the Gateway™ Technology instruction manual (version C) from Invitrogen®, hereby incorporated by reference herein. Genes were then transferred from this ENTRY vector to the destination vector (pRAXdes2) to obtain the expression vector pRAXCBH1.

Cells were transformed with an expression vector comprising a desired cellulase encoding nucleic acid. The host cells, *A. niger*, were then grown under conditions permitting expression of the desired cellulase as described in Example 2.

The sites different to *H. jecorina* CBH1, as identified in Example 3, may be involved in the thermostability of the variants and were therefore subjected to site saturated mutagenesis.

Example 5

Thermostability of CBH1 Variants

CBH I cellulase variants are cloned and expressed as above (see Example 4). Cel7A wild type and variants are then purified from cell-free supernatants of these cultures by column chromatography. Proteins are purified using hydrophobic interaction chromatography (HIC). Columns were run on a BioCAD® Sprint Perfusion Chromatography System using Poros® 20 HP2 resin both made by Applied Biosystems.

HIC columns are equilibrated with 5 column volumes of 0.020 M sodium phosphate, 0.5 M ammonium sulfate at pH 6.8. Ammonium sulfate is added to the supernatants to a final concentration of approximately 0.5 M and the pH is adjusted to 6.8. After filtration, the supernatant is loaded onto the column. After loading, the column is washed with 10 column volumes of equilibration buffer and then eluted with a 10 column volume gradient from 0.5 M ammonium sulfate to zero ammonium sulfate in 0.02 M sodium phosphate pH 6.8. Cel7A is eluted approximately mid-gradient Fractions are collected and pooled on the basis of reduced, SDS-PAGE gel analysis.

The melting points are determined according to the methods of Luo, et al., *Biochemistry* 34:10669 and Gloss, et al., *Biochemistry* 36:5612.

Data is collected on the Aviv 215 circular dichroism spectrophotometer. Spectra of the variants between 210 and 260 nanometers are taken at 25° C. Buffer conditions are 50 mM Bis Tris Propane/50 mM ammonium acetate/glacial acetic acid at pH 5.5. The protein concentration is kept between 0.25 and 0.5 mgs/mL. After determining the optimal wavelength to monitor unfolding, the samples are thermally denatured by ramping the temperature from 25° C. to 75° C. under the same buffer conditions. Data is collected for 5 seconds every 2 degrees. Partially reversible unfolding is monitored at 230 nanometers in an 0.1 centimeter path length cell.

The mutations introduced into the CBH I cellulase variants have a positive effect on the thermal stability of the variant CBH I cellulases compared to wild type.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. A cell culture composition comprising a CBH1 cellulase polypeptide, wherein said polypeptide comprises a substitution or deletion at a position corresponding to one or more of residues L6, P13, T24, Q27, S47, T59, T66, G88, T160, Q186, S195, T232, E236, E239, G242, N250, T281, F311, N327, D329, A336, K354, V407, P412, T417 or F418 of SEQ ID NO:2 and wherein the full length of said polypeptide has at least 97% sequence identity to SEQ ID NO:2.

2. The cell culture composition according to claim 1, wherein said polypeptide comprises a substitution selected from the group consisting of Q186(E), S195(A/F), E239S, G242(H/Y/N/S/T/D/A) and P412(T/S/A).

3. The cell culture composition according to claim 1, wherein said cells in said culture are filamentous fungus cells.

4. The cell culture composition according to claim 3, wherein said filamentous fungus cells are selected from the group consisting of *Trichoderma reesei, Trichoderma longibrachiatum, Trichoderma viride, Trichoderma koningii, Trichoderma harzianum, Penicillium, Humicola, Humicola insolens, Humicola grisea, Chrysosporium, Chrysosporium lucknowense, Gliocladium, Aspergillus, Fusarium, Neurospora, Hypocrea, Emericella, Aspergillus niger, Aspergillus awamori, Aspergillus aculeatus,* and *Aspergillus nidulans.*

* * * * *

UNITED STATES PATENT AND TRADEMARK OFFICE
CERTIFICATE OF CORRECTION

| | | |
|---|---|---|
| PATENT NO. | : 7,951,570 B2 | Page 1 of 1 |
| APPLICATION NO. | : 12/250227 | |
| DATED | : May 31, 2011 | |
| INVENTOR(S) | : Frits Goedegebuur et al. | |

It is certified that error appears in the above-identified patent and that said Letters Patent is hereby corrected as shown below:

At column 65, line 31:

Delete "5195," and insert --S195--

Signed and Sealed this
Third Day of April, 2012

David J. Kappos
*Director of the United States Patent and Trademark Office*